United States Patent

Doherty et al.

[11] Patent Number: 5,952,321
[45] Date of Patent: Sep. 14, 1999

[54] SUBSTITUTED AZETIDINONES AS ANTI-INFLAMMATORY AND ANTIDEGENERATIVE AGENTS

[75] Inventors: James Doherty, Montvale; Conrad Dorn, Plainfield; Philippe Durette, New Providence; Paul Finke, Milltown; Malcolm Maccoss, Freehold; Sander Mills, Woodbridge; Shrenik Shah, Metuchen; Soumya Sahoo, Old Bridge; William Hagmann, Westfield, all of N.J.; Scott Polo, Yardley, Pa.

[73] Assignee: Merck & Co., Inc., Rahway, N.J.

[21] Appl. No.: 08/764,775

[22] Filed: Dec. 12, 1996

Related U.S. Application Data

[63] Continuation of application No. 08/411,599, filed as application No. PCT/US93/10269, Oct. 26, 1993, abandoned, which is a continuation-in-part of application No. 07/992,193, Dec. 17, 1992, abandoned, which is a continuation-in-part of application No. 07/966,799, Oct. 27, 1992, abandoned.

[51] Int. Cl.⁶ .................. C07D 205/08; A61K 31/395
[52] U.S. Cl. .......................... 514/210; 540/360
[58] Field of Search .............. 540/360; 514/210

[56] References Cited

U.S. PATENT DOCUMENTS

| | | | |
|---|---|---|---|
| 4,064,120 | 12/1977 | Krapcho et al. | 540/361 |
| 4,115,382 | 9/1978 | Krapcho et al. | 540/361 |
| 4,166,907 | 9/1979 | Krapcho et al. | 540/361 |
| 4,174,317 | 11/1979 | Krapcho | 540/361 |
| 4,260,743 | 4/1981 | Bose | 540/364 |
| 4,510,086 | 4/1985 | Ross et al. | 540/360 |
| 4,534,896 | 8/1985 | Treuner et al. | 540/364 |
| 4,559,335 | 12/1985 | Zahler | 540/364 |
| 4,576,749 | 3/1986 | Zahler et al. | 540/364 |
| 4,680,391 | 7/1987 | Firestone et al. | 540/200 |
| 5,104,862 | 4/1992 | Durette et al. | 540/360 |
| 5,229,381 | 7/1993 | Doherty et al. | 540/360 |
| 5,348,953 | 9/1994 | Doherty et al. | 540/360 |

FOREIGN PATENT DOCUMENTS

| | | |
|---|---|---|
| Nr 295 547 | 2/1970 | Austria . |
| Nr 375 640 | 9/1981 | Austria . |
| 0 023 097 | 1/1981 | European Pat. Off. . |
| 0 042 026 | 12/1981 | European Pat. Off. . |
| 0 076 621 | 4/1983 | European Pat. Off. . |
| 0 199 630 | 10/1986 | European Pat. Off. . |
| 0 267 723 | 5/1988 | European Pat. Off. . |
| 0 337 549 | 9/1989 | European Pat. Off. . |
| 0 481 671 | 4/1992 | European Pat. Off. . |
| 1 945 542 | 3/1971 | Germany . |
| 2 046 822 | 3/1972 | Germany . |
| 2 046 823 | 3/1972 | Germany . |
| 27 48 827 | 3/1978 | Germany . |
| 28 24 554 | 12/1978 | Germany . |
| 28 42 466 | 4/1979 | Germany . |
| 29 11 589 | 9/1979 | Germany . |
| 30 07 298 | 3/1981 | Germany . |
| 1192952 | 5/1970 | United Kingdom . |
| 1604752 | 12/1981 | United Kingdom . |
| 2093839 | 9/1982 | United Kingdom . |
| WO 93/00332 | 1/1993 | WIPO . |

OTHER PUBLICATIONS

Firestone Chem. Abstracts, vol. 115, No. 5 (Aug. 5, 1991) 41275e.
Firestone Tetrahedron, vol. 46 No. 7, pp. 2255–2262 (1990).
Yosifugi Chem. Abstracts, vol. 105 Abs. 97895t (1986).
Peitsch. Hartmut, Tetrahedron Letters No. 45 pp. 4053–4056 (1976).
Tanaka, et al Heterocycles vol. 24, No. 9, pp. 2539–2543 (1986).
Bories, et al, Cell vol. 59 pp. 959–968 (1989).
D. Campanelli, et al, J. Exp. Med., vol. 172, 1709–1714 (1990).
G. Jenne, et al., Nature 346, 570 (1990).
Kao, et al., J. Clin. Invest. 82: 1962–1973 (1988).
Labbaye, et al., Proc. Natl. Acad. Sci. USA. vol. 88, 9253–9256 (1991).
D. Rees, et al., Ped. Pulmon. Suppl. 9: 250, No. 178 (1993) "A Systemic Elastase Inhibitor Protects Rats Against Lung Injury from Instilled CF Sputum Sol".
J. B. Doherty, et al., Proc. Natl. Acad. Sci. USA, 90:8727–8731 (Sep. 93).
W.A. Hanlon, et al., Journ. of Leukocyte Biology, 50: 43–48 (1991).
J. Stolk, et al., Am. J. Respir. Cell Mol. Biol, 6:521–526 (1992).
D.S. Fletcher, et al., Am. Rev. Respir Dis, 141:672–677 (1990).
P. Birrer, et al., Am. J. Respir. Crit, Care Med. 150: 207–213 (1994).
G. M. Turino, Anals of the New York Academy of Sciences, 624: 18–29 (1991).

Primary Examiner—Mark L. Berch
Attorney, Agent, or Firm—J. Antonio Garcia-Rivas; Valerie J. Camara; Mark R. Daniel

[57] ABSTRACT

New substituted azetidinones of the general Formula (I) which have been found to be potent elastase inhibitors and thereby useful anti-inflammatory and antidegenerative agents are described,

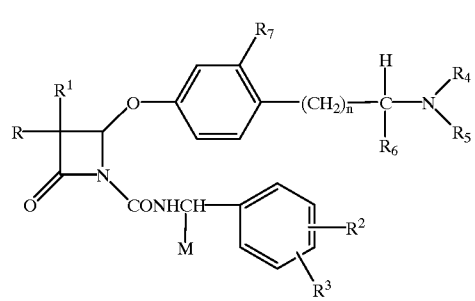

wherein n is 0

19 Claims, No Drawings

4,952,321

SUBSTITUTED AZETIDINONES AS ANTI-INFLAMMATORY AND ANTIDEGENERATIVE AGENTS

RELATED APPLICATION

This is a continuation of U.S. Pat. No. 08/411,599 filed on Apr. 11, 1995 (abandoned) which is a National Filing of PCT/US93/10269 filed Oct. 26, 1993, which is a Continuation-In-Part of U.S. Pat. No. 07/992,193 filed Dec. 17, 1992 (abandoned) which is a Continuation-In-Part of U.S. Pat. No. 07/966,799 filed Oct. 27, 1992 (abandoned).

BACKGROUND OF THE INVENTION

We have found that a group of new substituted azetidinones are potent elastase inhibitors and therefore are useful anti-inflammatory and antidegenerative agents.

Proteases from granulocytes and macrophages have been reported to be responsible for the chronic tissue destruction mechanisms associated with inflammation, including rheumatoid arthritis and emphysema. Accordingly, specific and selective inhibitors of these proteases are candidates for potent anti-inflammatory agents useful in the treatment of inflammatory conditions resulting in connective tissue destruction, e.g. rheumatoid arthritis, emphysema, bronchial inflammation, chronic bronchitis, glomerulonephritis, osteoarthritis, spondylitis, lupus, psoriasis, atherosclerosis, sepsis, septicemia, shock, myocardial infarction, reperfusion injury, periodontitis, cystic fibrosis and acute respiratory distress syndrome.

The role of proteases from granulocytes, leukocytes or macrophages are related to a rapid series of events which occurs during the progression of an inflammatory condition:

(1) There is a rapid production of prostaglandins (PG) and related compounds synthesized from arachidonic acid. This PG synthesis has been shown to be inhibited by aspirin-related nonsteroidal anti-inflammatory agents including indomethacin and phenylbutazone. There is some evidence that protease inhibitors prevent PG production;

(2) There is also a change in vascular permeability which causes a leakage of fluid into the inflamed site and the resulting edema is generally used as a marker for measuring the degree of inflammation. This process has been found to be induced by the proteolytic or peptide cleaving activity of proteases, especially those contained in the granulocyte, and thereby can be inhibited by various synthetic protease inhibitors, for example, N-acyl benzisothiazolones and the respective 1,1-dioxides. Morris Zimmerman et al., *J. Biol. Chem.*, 255, 9848 (1980); and (3) There is an appearance and/or presence of lymphoid cells, especially macrophages and polymorphonuclear leukocytes (PMN). It has been known that a variety of proteases are released from the macrophages and PMN, further indicating that the proteases do play an important role in inflammation.

In general, proteases are an important family of enzymes within the peptide bond cleaving enzymes whose members are essential to a variety of normal biological activities, such as digestion, formation and dissolution of blood clots, the formation of active forms of hormones, the immune reaction to foreign cells and organisms, etc., and in pathological conditions such as the degradation of structural proteins at the articular cartilage/pannus junction in rheumatoid arthritis etc.

Elastase is one of the proteases. It is an enzyme capable of hydrolyzing the connective tissue component elastin, a property not contained by the bulk of the proteases present in mammals. It acts on a protein's nonterminal bonds which are adjacent to an aliphatic amino acid. Neutrophil elastase is of particular interest because it has the broadest spectrum of activity against natural connective tissue substrates. In particular, the elastase of the granulocyte is important because, as described above, granulocytes participate in acute inflammation and in acute exacerbation of chronic forms of inflammation which characterize many clinically important inflammatory diseases.

Proteases may be inactivated by inhibitors which block the active site of the enzyme by binding tightly thereto. Naturally occurring protease inhibitors form part of the control or defense mechanisms that are crucial to the well-being of an organism. Without these control mechanisms, the proteases would destroy any protein within reach. The naturally occurring enzyme inhibitors have been shown to have appropriate configurations which allow them to bind tightly to the enzyme. This configuration is part of the reason that inhibitors bind to the enzyme so tightly (see Stroud, "A Family of Protein-Cutting Proteins" *Sci. Am*. July 1974, pp. 74–88). For example, one of the natural inhibitors, $\alpha_1$-Antitrypsin, is a glycoprotein contained in human serum that has a wide inhibitory spectrum covering, among other enzymes, elastase both from the pancreas and the PMN. This inhibitor is hydrolyzed by the proteases to form a stable acyl enzyme in which the active site is no longer available. Marked reduction in serum $\alpha_1$-antitrypsin, either genetic or due to oxidants, has been associated with pulmonary emphysema which is a disease characterized by a progressive loss of lung elasticity and resulting respiratory difficulty. It has been reported that this loss of lung elasticity is caused by the progressive, uncontrolled proteolysis or destruction of the structure of lung tissue by proteases such as elastase released from leukocytes. J. C. Powers, *TIBS*, 211 (1976).

Rheumatoid arthritis is characterized by a progressive destruction of articular cartilage both on the free surface bordering the joint space and at the erosion front built up by synovial tissue toward the cartilage. This destruction process, in turn, is attributed to the protein-cutting enzyme elastase which is a neutral protease present in human granulocytes.

This conclusion has been supported by the following observations:

(1) Recent histochemical investigations showed the accumulation of granulocytes at the cartilage/pannus junction in rheumatoid arthritis; and (2) a recent investigation of mechanical behavior of cartilage in response to attack by purified elastase demonstrated the direct participation of granulocyte enzymes, especially elastase, in rheumatoid cartilage destruction. H. Menninger et al., in *Biological Functions of Proteinases*, H. Holzer and H. Tschesche, eds. Springer-Verlag, Berlin, Heidelberg, N.Y., pp. 196–206, 1979.

In a second aspect this invention concerns the use of novel azetidinones in the treatment of certain cancers including nonlymphoblastic leukemias, acute myelogenous leukemia (FAB M1 and FAB M2), acute promyelocytic leukemia (FAB M3), acute myelomonocytic leukemia (FAB M4), acute monocytic leukemia (FAB M5), erythroleukemia, chronic myelogenous leukemia, chronic myelomonocytic leukemia, chronic monocytic leukemia and conditions associated with leukemia involving activity of PMN neutral proteases e.g. disseminated intravascular coagulation. We have found that the substituted azetidinones disclosed herein are potent inhibitors of proteinase 3 (PR-3), also known as myeloblastin.

See C. Labbaye, et al., Proc. Natl. Acad. Sci. USA, vol. 88, 9253–9256, (1991), Wegner autoantigen and myeloblastin are encoded by a single mRNA; D. Campanelli, et al., J. Exp. Med., vol. 172, 709–1714, (1990), Cloning of CDNA for proteinase 3: A serine protease, antibiotic, and autoantigen from human neutrophils; and Bories, et. al., Cell vol. 59, 959–968, (1989) Down-regulation of a serine protease, myeloblastin, causes growth arrest and differentiation of promyelocytic leukemia cells.

Recently, down regulation of PR-3 has been implicated in the proliferation and maintenance of a differentiated state of certain leukemia cells. In particular, Bories, et. al., have shown that expression of this enzyme, hereinafter designated proteinase 3/myeloblastin, can be inhibited by treatment of HL-60 human leukemia cells with an antisense oligodeoxynucleotide and that such treatment induces differentiation and inhibits proliferation of these cells. Moreover, we have now demonstrated that the treatment of the HL-60 cell human leukemia cell line, among others, with the compounds of the instant invention, likewise results in the inhibition of proliferation and induction of differentiation in such cells.

Accordingly, we believe that treatment of leukemia such as nonlymphoblastic leukemias, acute myelogenous leukemia (FAB M1 and FAB M2), acute promyelocytic leukemia (FAB M3), acute myelomonocytic leukemia (FAB M4), acute monocytic leukemia (FAB M5), erythroleukemia, chronic myelogenous leukemia, chronic myelomonocytic leukemia, chronic monocytic leukemia and conditions associated with leukemia involving activity of PMN neutral proteases e.g. disseminated intravascular coagulation, comprising: administration of a therapeutically effective amount of compound of formula I will result in remission of the disease state. Administration may be either oral or parenteral.

BRIEF DESCRIPTION OF THE INVENTION

The instant invention is directed to specifically substituted azetidinones of Formula I

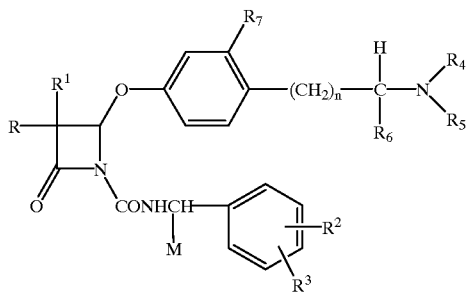

I

These substituted azetidinones have been found to be useful anti-inflammatory and antidegenerative agents. This invention is also directed to pharmaceutical compositions and methods of using these specifically substituted azetidinones. These compounds will also be useful in the treatment of certain leukemias and leukemia related conditions.

DETAILED DESCRIPTION OF THE INVENTION

This invention relates to potent elastase inhibitors of Formula (I),

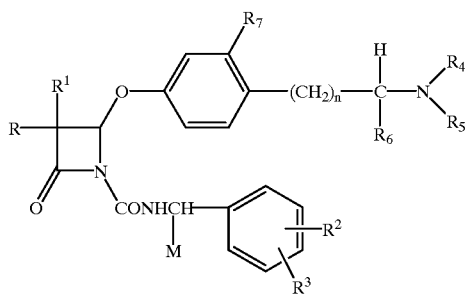

I which are useful in the prevention, control and treatment of inflammatory and degenerative conditions especially arthritis and emphysema.

More particularly, the instant invention is directed to the compounds of the Formula (I)

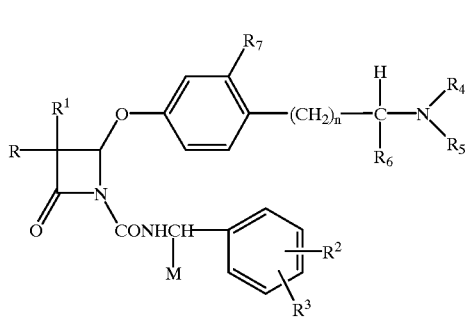

I and pharmaceutically acceptable salts thereof wherein:

R is $C_{1-6}$ alkyl;

$R^1$ is $C_{1-6}$ alkyl or $C_{1-6}$ alkoxy-$C_{1-6}$ alkyl;

M is
 (1) hydrogen,
 (2) $C_{1-6}$ alkyl,
 (3) hydroxy $C_{1-6}$ alkyl,
 (4) halo $C_{1-6}$ alkyl,
 (5) $C_{2-6}$ alkenyl, or
 (6) $C_{1-6}$ alkoxy-$C_{1-6}$ alkyl;

$R^2$ and $R^3$ are each independently
 (1) hydrogen,
 (2) $C_{1-6}$ alkyl,
 (3) halo,
 (4) carboxy,
 (5) $C_{1-6}$ alkoxy,
 (6) phenyl,
 (7) $C_{1-6}$ alkylcarbonyl,
 (8) di-($C_{1-6}$alkyl)amino, or $R^2$ and $R^3$ are joined together to form the group methylenedioxy or $R^2$ and $R^3$ together with the carbon atoms to which they are attached form a furan ring;

$R_7$ is
 (a) hydrogen,
 (b) halo,
 (c) $C_{1-3}$alkyl, (d) hydroxy, or
(e) $C_{1-3}$alkoxy; and n is 0, 1, 2, 3, 4, or 5;

$R_4$ is selected from
(a) hydrogen,
(b) $C_{1-6}$ alkyl,
(c) $C_{1-6}$ alkyloxy $C_{2-3}$ alkyl; or
(d) cyclopropyl, $R_5$ is selected from
(a) hydrogen,
(b) $C_{1-6}$ alkyl,
(c) $C_{1-6}$ alkyloxy $C_{2-3}$ alkyl, or
(d)

$$(CH)(CH_2)_m\text{—}X,$$
$$R_{11}$$

wherein m is 0, 1, 2, 3 or 4, such that when m is 1, 2 or 3, or 4

X is
(1)

$$\text{—N—C(O)—O—}C_{1-6}\text{alkyl},$$
$$R_8$$

(2) —O—C(O)—$C_{1-6}$alkyl,
(3) —O—$R_8$, wherein $R_8$ and $R_{11}$ are defined immediately below, or O—$R_8$ and $R_{11}$ may be joined together to form a saturated ring of 5–7 atoms containing 1 oxygen,
(4)

$$\text{—C(O)—NR}_{10},$$
$$R_9$$

wherein $R_8$, $R_9$ and $R_{10}$, $R_{11}$ are each independently hydrogen, $C_{1-6}$alkyl, phenyl or benzyl, or wherein $R_9$ and $R_{10}$ are joined together to form a saturated monocyclic ring of 5 to 7 atoms containing one or two heteroatoms selected from
(a) morpholinyl,
(b) thiomorpholinyl,
(c) piperidinyl
(d) pyrrolidinyl said ring optionally substituted with $C_{1-3}$ alkyl or $R_8$ and $R_4$ are joined together to form a piperazinyl or homopiperazinyl ring, said ring optionally substituted with $C_{1-3}$ alkyl, $R_9$ (5)

$$\text{—O—C(O)—NR}_{10},$$
$$R_9$$

(6)

$$\text{—N—C(O)—NR}_{10},$$
$$R_8 \quad R_9$$

(7)

$$\text{—N—C(O)—O—}C_{1-6}\text{alkyl},$$
$$R_8$$

(8) —OH,
(9) $C_{1-3}$ alkyloxy-$C_{1-3}$ alkyloxy,
(10) —C(O)OH, —C(O) O$R_8$, or —C(O) $C_{1-6}$ alkyl
(11) —S—$C_{1-6}$alkyl,
(12) —S(O)—$C_{1-6}$alkyl, or
(13) —S(O)$_2$—$C_{1-6}$alkyl;

and when m is 0,

X is —C(O)OH—C(O)O$R_8$, —C(O)$C_{1-6}$ alkyl or $$(CH_2)p\text{—N—}R_{10},$$
$$R_9$$

(e) C(O)—Y, wherein Y is
(1) hydrogen,
(2) $C_{1-6}$alkyl,
(3)

$$\text{—C(O)NR}_9$$
$$R_{10};$$

wherein p is 0, 1 or 2,
(4) pyridylmethyl,
(5) imidazolyl methyl,
(f) mono or di substituted benzyl or mono substituted pyridylmethyl, wherein the substitutent is
(1) hydrogen,
(2) halo,
(3) $C_{1-6}$ alkyl, or
(4) $C_{1-6}$ alkylcarbonylamino;

$R_6$ is selected from hydrogen, $C_{1-4}$ alkyl, and $C_{1-3}$ alkoxy $C_{1-3}$alkyl; or wherein $R_4$ and $R_5$ are joined together to form a mono or di substituted ring of 5, 6, or 7 atoms selected from
(1) piperidinyl,
(2) piperazinyl,
(3) morpholinyl,
(4) thiomorpholinyl,
(5) pyrrolidinyl,
(6) pyrryl, and
(7) imidazolyl, wherein the substituents are each selected from the group consisting of hydrogen, hydroxy, hydroxymethyl, $C_{1-3}$ alkyl, $C_{1-3}$ alkyloxy, $C_{1-3}$ alkyloxymethyl, $C_{1-6}$ alkylcarbonyl;

$R_4$ and $R_6$ are joined together to form a mono cylic ring of 5, 6, or 7 atoms including the atoms to which they are attached, said ring optionally having a second hetero atom selected from O or N or S. The ring may be either saturated or unsaturated.

As appreciated by those of skill in the art the term "alkyl" such as in $C_{1-6}$ alkyl, includes, Methyl, ethyl, propyl, butyl, pentyl, and hexyl, and where appropriate, branched chained forms including isopropyl and tert-butyl.

In one Class, the invention concerns compounds of Formula I wherein

R is $C_{1-3}$ alkyl;
$R_1$ is $C_{1-3}$ alkyl;
M is (a) $C_{1-6}$ alkyl, or
(b) $C_{2-6}$ alkenyl;

$R^2$ is
(a) hydrogen
(b) $C_{1-6}$ alkyl, or $C_{1-6}$ alkoxy, and $R^3$ is hydrogen, or $R^2$ and $R^3$ are joined together to form the group methylenedioxy or $R^2$ and $R^3$ together with the carbon atoms to which they are attached form a furan ring;

$R_4$ is selected from
(a) hydrogen,
(b) $C_{1-3}$ alkyl, and
(c) $C_{1-3}$ alkoxy $C_{2-3}$ alkyl;

$R_5$ is selected from
(a) hydrogen,
(b) $C_{1-6}$ alkyl,
(c) $C_{1-6}$ alkyloxy $C_{2-3}$ alkyl,
(d) $CH_2$—$(CH_2)$m-X, such that when m is 1 or 2;

X is
(1) —O—C(O)—$C_{1-6}$alkyl,
(2) —O—$R_8$,
(3)

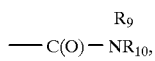

wherein $R_8$, $R_9$ and $R_{10}$ are each independently hydrogen or $C_{1-6}$alkyl, (4)

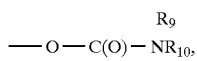

(5)

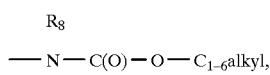

(6) —$C_{1-3}$alkyloxyethyl,
(7) —S—$C_{1-6}$alkyl,
(8) —S(O)—$C_{1-6}$alkyl, or
(9) —S(O)$_2$—$C_{1-6}$alkyl,
(10)

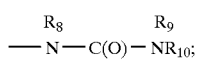

and when m is 0,
X is —C(O)OH or

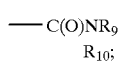

(e) mono substituted benzyl or mono substituted pyridylmethyl, wherein the substitutent is
(1) hydrogen,
(2) halo,
(3) $C_{1-6}$ alkyl, or
(4) $C_{1-6}$ alkylcarbonylamino;

n is 0, 1, 2 or 3, and $R_6$ is selected from hydrogen, $C_{1-4}$ alkyl, and $C_{1-3}$ alkoxy $C_{1-3}$alkyl; or $R_4$ and $R_5$ or $R_9$ and $R_{10}$ are joined together to form a mono or di substituted ring selected from
(a) piperidinyl,
(b) pyrrolidinyl, and
(c) morpholinyl;

or $R_4$ and $R_8$ are joined together to form a piperazine ring, optionally substituted with $C_{1-3}$ alkyl, or $R_4$ and $R_6$ are joined together to form a saturated monocyclic ring of 5 to 6 atoms including the atoms to which they are attached, said ring optionally having a second hetero atom selected from O or N.

Within this class are the compounds wherein

R is methyl or ethyl;

$R_1$ is methyl or ethyl;

M is
(a) $C_{1-4}$ alkyl, or
(b) $C_{2-3}$ alkenyl;

$R^2$ is
(a) hydrogen,
(b) $C_{1-3}$ alkyl, or $C_{1-3}$ alkoxy, and $R^3$ is hydrogen, or $R^2$ and $R^3$ are joined together to form the group methylenedioxy or $R_2$ and $R_3$ together with the carbon atom to which they are attached form a furan ring;

$R_4$ is selected from
(a) hydrogen,
(b) $C_{1-3}$ alkyl, and
(c) $C_{1-3}$ alkoxy $C_{2-3}$ alkyl;

$R_5$ is selected from
(a) hydrogen,
(b) $C_{1-3}$ alkyl,
(c) $C_{1-3}$ alkyloxy $C_{2-3}$ alkyl,
(d) $CH_2$—$(CH_2)_m$-X, wherein m is 1;

X is
(1)

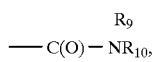

wherein $R_8$, $R_9$ and $R_{10}$ are each independently hydrogen or $C_{1-6}$alkyl, (2)

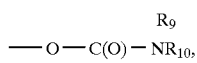

(3)

(4)

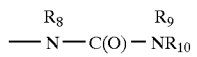

(e) mono substituted benzyl or mono substituted pyridylmethyl, wherein the substitutent is
(1) hydrogen,
(2) halo,
(3) $C_{1-3}$ alkyl, or
(4) $C_{1-3}$ alkylcarbonylamino;

n is 0 or 1,

R$_6$ is selected from hydrogen, methyl and methoxymethyl; or

R$_4$ and R$_5$ or R$_9$ and R$_{10}$ are joined together to form a mono or disubstituted ring selected from
(a) piperidinyl,
(b) pyrrolidinyl, and
(c) morpholinyl; or R$_4$ and R$_6$ are joined together to form a pyrrolidinyl ring or R$_4$ and R$_8$ are joined together to form a piperazinyl ring.

In another aspect the present invention is directed to the treatment of leukemia, such as nonlymphoblastic leukemias, acute myelogenous leukemia (FAB M1 and FAB M2), acute promyelocytic leukemia (FAB M3), acute myelomonocytic leukemia (FAB M4), acute monocytic leukemia (FAB M5), erythroleukemia, chronic myelogenous leukemia, chronic myelomonocytic leukemia, chronic monocytic leukemia and conditions associated with leukemia involving activity of PMN neutral proteases e.g. disseminated intravascular coagulation with compounds of Formula I.

I

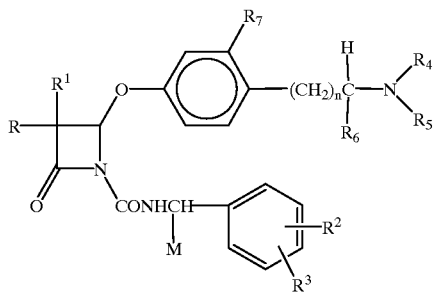

or a pharmaceutically acceptable salt thereof as defined in any of the alternative definitions provided above.

Treatment of leukemia cells comprises: administration of a therapeutically effective amount of a compound of Formula I results in the inhibition of proteinase 3/myeloblastin, inhibition of elastase, inhibition of proliferation of the leukemia cells, induction of differentiation of the leukemia cells, and remission of the disease state.

In one alternative embodiment the invention concerns a method of treating leukemia comprising: administration to a patient in need of such treatment of a therapeutically effective amount of compound of Formula I.

In a second alternative embodiment the invention concerns a method of inhibiting proteinase 3/myeloblastin, comprising: administration to a patient in need of such inhibition of a therapeutically effective amount of compound of Formula I as defined above.

In a third alternative embodiment the invention concerns a method of inhibiting proteinase 3/myeloblastin and elastase, comprising: administration to a patient in need of such inhibition of a therapeutically effective amount of compound of Formula I as or a pharmaceutically acceptable salt thereof as defined above.

In a fourth embodiment the invention concerns a method of inducing cellular differentiation in leukemia cells comprising: administration to a patient in need of such inhibition of a therapeutically effective amount of compound of formula I or a pharmaceutically acceptable salt thereof as defined above.

Each of the above alternative embodiments (i.e., those relating to PR3 or cancer), also concerns co-administration of a compound of Formula I as defined above, with an agent or agents known in the art for treatment of leukemia, including, but not limited to epsilon-aminocaproic acid, heparin, trasylol (aprotinin); prednisolone; cytosine arabinoside; b-mercaptopurine; cytarabine; an anthracycline (see Young et. al. (1981) N. Engl. J. Med. 305:139) such as dauorubicin, doxorubicin and epidoxorubicin; Vitamin A derivatives including retinoids and all-trans-retinoic acid (See Ellison R. R. et.al. (1968) *Blood* 32:507, Arabinosyl Cytosine: A useful agent in the treatment of leukemia in adults; Cytarabine: Therapeutic new dimensions, Semin. Oncol. 12:1 (1985, supp 3); Weinstein H. J. et. al. (1983) *Blood* 62:315, Chemotherapy for acute myelogenous leukemia in children and adults results in an enhanced therapeutic response.

Accordingly, in a fifth alternative embodiment the invention concerns a pharmaceutical composition comprising:
a pharmaceutical carrier, a therapeutically effective amount of compound selected from the group consisting of epsilon-aminocaproic acid, heparin, trasylol, prednisolone, cytosine arabinoside, b-mercaptopurine, cytarabine, an anthracycline and a vitamin A derivative (which includes vitamin A); and a therapeutically effective amount of compound of Formula I as defined above.

In a sixth alternative embodiment the invention concerns a method of treating leukemia comprising:
co-administration to a patient in need of such treatment of a therapeutically effective amount of compound selected from the group consisting of epsilon-aminocaproic acid, heparin, trasylol, prednisolone, cytosine arabinoside, b-mercaptopurine, cytarabine, an anthracycline, and a vitamin A derivative; and a therapeutically effective amount of compound of Formula I as defined above.

In a seventh alternative embodiment the invention concerns a method of inhibiting proteinase 3/myeloblastin, comprising:
co-administration to a patient in need of such inhibition of a therapeutically effective amount of compound selected from the group consisting of epsilon-aminocaproic acid, heparin, trasylol, prednisolone, cytosine arabinoside, b-mercaptopurine, cytarabine, an anthracycline, and a vitamin A derivative;and a therapeutically effective amount of compound of Formula I as defined above.

In an eighth alternative embodiment the invention concerns a method of inhibiting proteinase 3/myeloblastin and elastase, comprising:
administration to a patient in need of such inhibition of a therapeutically effective amount of compound selected from the group consisting of epsilon-aminocaproic acid, heparin, trasylol, prednisolone, cytosine arabinoside, b-mercaptopurine, cytarabine, an anthracycline, and a vitamin A derivative; and a therapeutically effective amount of compound of Formula I as defined above.

In a ninth alternative embodiment the invention concerns a method of inducing cell differentiation in leukemia cells comprising:
administration to a patient in need of such inducing of a therapeutically effective amount of compound selected from the group consisting of epsilon-aminocaproic acid, heparin, trasylol, prednisolone, cytosine arabinoside, b-mercaptopurine, cytarabine, an anthracycline and a vitamin A derivative; and a therapeutically effective amount of compound of Formula I as defined above.

This invention also relates to a method of treating inflammation in patients using a compound of Formula (I), particularly a preferred compound as the active constituent.

It has been found that the compounds of Formula (I), and in particular, compounds of Tables I to IV, Schemes 1 to 13 and the Examples 1 to 44, are effective inhibitors of the proteolytic function of human neutrophil elastase as shown below in Table 1. They are also potent inhibitors of PR3 as shown in Table IV.

TABLE I

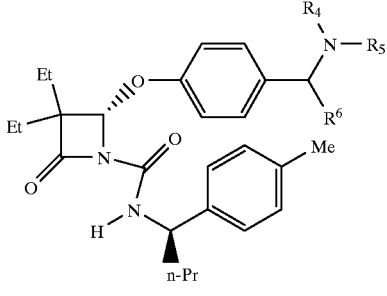

| $R_4$ | $R_5$ | $R_6$ | $K_{obs}/[I]$ |
|---|---|---|---|
| Me | Bn | H | 400,000 |
| —CH$_2$CH$_2$OCH$_2$CH$_2$— | | H | 820,000 |
| Me | Me | H | 560,000 |
| —CH$_2$CH$_2$N(i-Pr)CH$_2$CH$_2$— | | H | 1,200,000 |
| —CH$_2$CH$_2$N(Ac)CH$_2$CH$_2$— | | H | 950,000 |
| —CH$_2$CH$_2$N(Bz)CH$_2$CH$_2$— | | H | 1,700,000 |
| Me | CH$_2$CH$_2$CO$_2$H—TFA | H | 440,000 |
| Me | CH$_2$CH$_2$OH | H | 560,000 |
| —CH$_2$CHMeNCHMeCH$_2$— | | H | 980,000 |
| —CHMeCH$_2$CH$_2$CHMe— | | H | 670,000 |
| Me | CH$_2$CH$_2$NMe$_2$ | H | 850,000 |
| Me | CH$_2$CH$_2$N(Me)Bn | H | 1,250,000 |
| —CHCHNCH— | | H | 1,600,000 |
| Me | CH$_2$CH$_2$OCONMe$_2$ | H | 610,000 |
| Me | CH$_2$CH$_2$CONMe$_2$ | H | 870,000 |
| —CH$_2$CH$_2$N(CO$_2$Me)CH$_2$CH$_2$— | | H | 730,000 |
| Me | CH$_2$CH$_2$OMe | H | 440,000 |
| —CH$_2$CH$_2$N(CONMe$_2$)CH$_2$CH$_2$— | | H | 1,550,000 |
| Me | CH$_2$CH$_2$OCONHMe | H | 700,000 |
| —CHCHNCMe— | | H | 1,400,000 |
| —CH$_2$CH$_2$N(CONEt$_2$)CH$_2$CH$_2$— | | H | 1,400,000 |
| Me | CH$_2$CH$_2$N(Me)CONMe$_2$ | H | 850,000 |
| Me | i-Pr | H | 850,000 |
| i-Pr | CH$_2$CH$_2$OMe | H | 500,000 |
| Me | CH$_2$CH$_2$N(Me)Ac | H | 650,000 |
| Et | CH$_2$CH$_2$OMe | H | 565,000 |
| Me | CH$_2$CH$_2$N(Me)COOMe | H | 1,100,000 |
| —CHMeCH$_2$CH$_2$CHMe— | | H | 1,150,000 |
| Me | CH$_2$CH$_2$OEt | H | 600,000 |
| Me | CH$_2$CH$_2$OCOCMe$_3$ | H | 230,000 |
| Me | CH$_2$CH$_2$OCOCHMe$_2$ | H | 630,000 |
| Me | CH$_2$CH$_2$OPh | H | 750,000 |
| Me | CH$_2$CH$_2$OCONEt$_2$ | H | 1,230,000 |
| —CHCHNCEt— | | H | 2,250,000 |
| —CH$_2$CMeNCH$_2$CHMe— | | H | 2,500,000 |
| Me | CH$_2$CH$_2$OCONH(i-Pr) | H | 1,850,000 |
| Me | CH$_2$CH$_2$OCON(CH$_2$CH$_2$—OCH$_2$CH$_2$) | H | 1,400,000 |
| Me | CH$_2$CH$_2$OCON(Me)n-Bu | H | 1,300,000 |
| Me | CH$_2$CON(n-Pr)$_2$ | H | 910,000 |
| Me | CH$_2$CH$_2$SEt | H | 1,050,000 |
| CH$_2$CH$_2$OMe | CH$_2$CH$_2$OMe | H | 820,000 |
| Me | CH$_2$CH(CH$_2$CH$_2$CH$_2$O) | H | 900,000 |
| Me | CH$_2$CH$_2$SMe | H | 675,000 |
| Et | CH$_2$CH$_2$NHAc | H | 850,000 |
| Me | CH$_2$CH(CH$_2$CH$_2$CH$_2$O) | H | 1,000,000 |
| Me | CH$_2$CH$_2$OCONMe$_2$ | Me | 925,000 |
| Et | CH$_2$CH$_2$OMe | Me | 600,000 |
| Me | CH$_2$CH$_2$OMe | Me | 600,000 |
| —CH$_2$CH$_2$SCH$_2$— | | H | 940,000 |
| —CH$_2$CH$_2$SCH$_2$CH$_2$— | | H | 915,000 |
| —CH$_2$CH$_2$CH$_2$CH($\underline{S}$—CH$_2$OH) | | H | 950,000 |
| —CH$_2$CH$_2$CH$_2$CH($\underline{S}$—CH$_2$OMe)— | | H | 1,550,000 |
| —CH$_2$CH$_2$CH(OH)CH$_2$— | | H | 1,200,000 |
| —CH$_2$CH$_2$CH(OH)CH$_2$CH$_2$— | | H | 1,150,000 |
| Me | Me | CH$_2$OMe | 1,275,000 |
| Me | CH(Me)CH$_2$OMe | H | 1,225,000 |
| Et | CH$_2$CH$_2$OCONMe$_2$ | H | 1,400,000 |
| Me | CH$_2$CH$_2$SOEt | H | 1,400,000 |
| Me | CH$_2$CH$_2$SO$_2$Et | H | 1,500,000 |
| Me | CH$_2$CH$_2$CH$_2$OMe | H | 1,500,000 |
| Me | CH$_2$CH$_2$CH$_2$OCONMe$_2$ | H | 2,100,000 |
| Me | CH$_2$CH$_2$OCH$_2$CH$_2$OMe | H | 1,900,000 |
| Et | CH$_2$CH$_2$OCH$_2$CH$_2$OMe | H | 1,300,000 |
| Et | CH(Me)CH$_2$OMe | H | 670,000 |
| —CH$_2$CH$_2$N(COCHMe$_2$)CH$_2$CH$_2$— | | H | 1,600,000 |
| Et | Et | CH$_2$OMe | 1,100,000 |
| n-Pr | n-Pr | CH$_2$OMe | 1,000,000 |
| —CH$_2$CH$_2$CH$_2$— | | CH$_2$OMe | 1,700,000 |
| Me | n-Pr | CH$_2$OMe | 1,500,000 |
| —CH$_2$CH$_2$OCH$_2$CH$_2$— | | Me | 460,000 |
| Me | CH$_2$CH$_2$OMe | Et | 550,000 |
| —CH$_2$CH$_2$CH(OMe)CH$_2$— | | H | 765,000 |
| —CH$_2$CH$_2$CH$_2$CH($\underline{S}$—CH$_2$OMe)— (isomer A) | | Me | 960,000 |
| —CH$_2$CH$_2$CH$_2$CH($\underline{S}$—CH$_2$OMe)— (isomer B) | | Me | 1,000,000 |
| Me | CH(Me)CH$_2$OMe | Me | |
| Me | CH$_2$CH$_2$OCH$_2$CH$_2$OMe | Me | 825,000 |
| Me | Et | CH$_2$OMe | 1,000,000 |
| —CH$_2$CH$_2$CH(OMe)CH$_2$— | | Me | 1,000,000 |
| —CH$_2$CH$_2$CH$_2$CH($\underline{R}$—CH$_2$OH)— | | H | 725,000 |
| —CH$_2$CH$_2$N(—CNCHCHCHN)CH$_2$CH$_2$— | | H | 715,000 |
| Et | CH$_2$CH$_2$SMe | H | 690,000 |
| CH$_2$CH$_2$OMe | —CH$_2$CH$_2$CH$_2$— | | 940,000 |
| Me | CH$_2$CH$_2$OMe | (S)—Me | 515,000 |
| Me | CH$_2$CH$_2$OMe | (R)—Me | 525,000 |
| H | Me | (R)—Me | |
| H | Me | (S)—Me | |
| Me | CH$_2$CH$_2$OH | Me | 770,000 |
| H | CH$_2$CH$_2$OMe | Me | 680,000 |
| H | CH$_2$CH$_2$OH | Me | 660,000 |
| Me | i-Pr | CH$_2$OMe | 800,000 |
| CH$_2$CH$_2$OEt | —CH$_2$CH$_2$CH$_2$— | | 1,100,000 |
| H | H | H | 325,000 |
| H | Me | H | |
| H | Ac | H | 750,000 |
| H | CONH isoPr | H | 1,100,000 |
| H | CONHMe | H | 1,100,000 |
| H | CONHnPr | H | 1,200,000 |
| H | CONH Bn | H | 1,600,000 |
| H | COCH$_2$ NMe$_2$ | H | 800,000 |
| H | COCH$_2$ CH$_2$ N Et$_2$ | H | 850,000 |
| H | COCH$_2$-3-pyridyl | H | 1,250,000 |
| H | COCH$_2$-4-pyridyl | H | 1,700,000 |
| H | COCH$_2$-4-imidazolyl | H | 850,000 |
| H | COCH$_2$ N(Me)Bn | H | 1,400,000 |

TABLE II

| R₄ | R₅ | n | K_obs/[I] |
|---|---|---|---|
| Me | Me | 4 | 525,000 |
| Et | Et | 3 | 540,000 |
| Me | Me | 2 | 1,130,000 |
| Me | Bn | 2 | 1,325,000 |
| —CH₂CH₂OCH₂CH₂— | | 2 | 600,000 |
| Me | Bn | 4 | 640,000 |
| Me | CH₂CH₂NMe₂ | 2 | 1,200,000 |

TABLE III

| R₂ | R₃ | R₄ | R₅ | R₆ | R₇ | K_obs/[I] |
|---|---|---|---|---|---|---|
| OMe | H | Me | CH₂CH₂OMe | H | H | 900,000 |
| OEt | H | Me | CH₂CH₂OMe | H | H | 1,300,000 |
| OEt | H | Et | CH₂CH₂OMe | H | H | 1,120,000 |
| OMe | H | Et | CH₂CH₂OMe | H | H | 1,000,000 |
| Me | H | Et | CH₂CH₂OMe | H | Cl | 550,000 |
| Me | H | Me | CH(Me)CH₂OMe | H | OMe | 1,650,000 |
| —OCH₂O— | | Et | CH(Me)CH₂OMe | H | H | 1,600,000 |
| —OCH₂O— | | Et | CH₂CH₂OMe | H | H | 1,900,000 |
| Me | H | Et | CH₂CH₂OCH₂CH₂OMe | H | OMe | 1,700,000 |
| Me | H | Et | CH(Me)CH₂OMe | H | OMe | 1,300,000 |
| Me | H | CH₂ CH₂OMe | CH₂CH₂OMe | H | Cl | 1,000,000 |
| Me | H | Me | CH₂CH₂OMe | H | Cl | 1,000,000 |
| Me | H | Me | CH(Me)CH₂OMe | H | Cl | 650,000 |
| Me | H | Me | CH₂CH₂OMe | H | 3,5-Me₂ | 300,000 |
| Me | H | Me | CH₂CH₂OMe | H | Me | 540,000 |
| Me | H | Et | CH₂CH₂OMe | H | Me | 450,000 |
| Me | H | Et | CH(Me)CH₂OMe | H | Me | 400,000 |
| —OCH₂O— | | Et | CH₂CH₂OCONMe₂ | H | H | |
| —OCH₂O— | | Me | n-Pr | CH₂OMe | H | 1,800,000 |
| —OCH₂O— | | Me | Et | CH₂OMe | H | 1,650,000 |
| —OCHCH— | | Et | CH(Me)CH₂OMe | H | H | 1,050,000 |
| —OCHCH— | | Et | CH₂CH₂OMe | H | H | 1,100,000 |
| —OCH₂O— | | Et | CH₂CH₂OMe | H | H | 1,300,000 |
| —OCH₂O— | | Me | CH₂CH₂OMe | Me | H | 1,300,000 |
| —OCH₂O— | | Me | Me | CH₂OMe | H | 1,900,000 |
| —OCH₂O— | | H | cyclopropyl | H | H | 1,600,000 |
| —OCH₂O— | | —CH₂CH₂N(COMe₂)CH₂CH₂ | | H | H | 4,000,000 |

The method of analysis and further assay results are shown hereinunder.

Enzyme Assays for the Inhibition of Human Polymorphonuclear Leukocyte Elastase Via Hydrolysis of N-t-Boc-alanyl-alanyl-prolylalanine-p-nitroanilide (Boc-AAPAN) or N-t-Boc-alanyl-prolylvaline-p-nitroanilide (Boc-AAPVN) Reagent:

0.05M TES (N-tris[hydroxymethyl]methyl-2-aminoethanesulfonic acid) Buffer, pH 7.5.

0.2 mM Boc-AAPAN or Boc-AAPVN.

To prepare substrate, the solid was first dissolved in 10.0 ml DMSO. Buffer at pH 7.5 was then added to a final volume of 100 ml.

Crude extract of human polymorphonuclear leukocytes (PMN) containing elastase activity.

Inhibitors (azetidinones) to be tested dissolved in DMSO just before use.

To 1.0 ml of 0.2 mM Boc-AAPAN in a cuvette, 0.01–0.1 ml of DMSO with or without inhibitor was added. After mixing, a measurement was taken at 410 mµ to detect any spontaneous hydrolysis due to presence of test compound. 0.05 Milliliters of PMN extract was then added and the ΔOD/min at 410 mµ was measured and recorded. Beckman model 35 spectrophotometer was used.

Results in Tables I to III were reported as ID₅₀, effective dosage in micrograms per milliliter (µg/ml) for 50% inhibition of the enzyme activity 2 minutes after zero time.

Results were also expressed as Ki, the micromolar concentration of the inhibitor (µM) giving 50% of the control enzyme activity; or as $^k$obs/I which is the second order rate constant in per mole per second for inactivation of the enzyme.

The elastase activity in the crude PMN extract may vary from one preparation to another. A control of each new batch is run, and the volume added in the assay procedure is adjusted according to activity.

TABLE IV

SECOND ORDER RATE CONSTANTS FOR THE INHIBITION OF HUMAN PROTEINASE 3

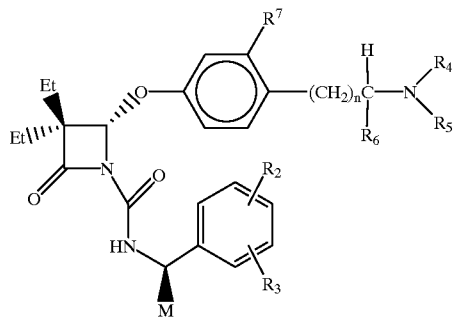

wherein M is n-propyl; and $R_7$ is H; n = 0

| R2 | R3 | R4 | R5 | R6 | SORC [M$^{-1}$, Sec$^{-1}$] |
|---|---|---|---|---|---|
| —O—CH$_2$O— | | Me | —CH$_2$CH$_2$—OMe | Me | 31,000 |

ASSAY

The PR3 catalyzed hydrolysis of MeO-Succ-AAPV-pNA was measured in a spectrophotometer monitoring absorbance at 410 nm. The enzymatic activity was determined in 45 mM TES at pH 7.5, 450 mM NaCl and 10% DMSO. The data were fit by non-linear regression to equation 1 to obtain the initial rates. The nonlinear progress curves observed with time dependent inhibitors were fit to equation 2 to obtain the first order rate constant $K_{obs}$. Results were expressed as $k_{obs}/I$ which is the second order rate constant (SORC) in per mole per second for inactivation of the enzyme.

$$Y = v_s X + B \qquad \text{EQN 1}$$

$$Y = v_s^* x + [(v_o - v_s)(1 - e^{(-K^o \cdot x)})/K_o] + A_o \qquad \text{EQN 2}$$

Kinetic constants for the inhibition of PR3 catalyzed hydrolysis of 0.2 mM MeO-succ-AAPV-pNA were determined by varying the concentration of inhibitor present in the reaction vessel.

Accordingly, the compounds of Formula (I), can be used to reduce inflammation and/or relieve pain in diseases such as emphysema, rheumatoid arthritis, osteoarthritis, gout, bronchial inflammation, chronic or acute bronchitis, cystic fibrosis, adult respiratory distress syndrome, atherosclerosis, sepsis, septicemia, shock, periodontitis, glomerular nephritis or nephosis, myocardial infarction, reperfusion injury, infectious arthritis, rheumatic fever and the like, and may reduce hemorrhage in acute promyelocytic leukemia and the like.

In this capacity, and as appreciated by those of skill in the art, therapy comprising administration of compounds of Formula I may actually include co-administration of one or more additional active agents. Classes of active agents include, but are not limited to β$_2$-adrenergic agonists; anti-cholinergic agents; steroids; non-steroidal anti-inflammatory agents (NSAID's); mucolytic agents; most all stabilizers; and antibacterials.

For purposes of this specification, β$_2$-adrenergic agonists are intended to include, but are not limited to, metaproterenol, terbutaline, isoetharine, albuterol, and ritodrine, carbuterol, fenoterol, quinterenol, rimiterol, salmefamol, soterenol, and tretoquinol.

For purposes of this specification, anti-cholinergic agents are intended to include, but are not limited to, atropine, and iptratropium-bromide.

For purposes of this specification, mucolytic agents are intened to include, but are not limited to acetylcysteine and guattenesin.

For purposes of this specification, steroids are intended to include, but are not limited to, prednisone, beclomethasone, budesonide, solumedrol, triamcinolone, and methylprednisolone.

For purposes of this specification most cell stabilizers are intended to include, but are not limited to cromolyn and ketotafin.

For purposes of this specification, non-steroidal anti-inflammatory agents are intended to include, but are not limited to aspirin, diflunisal, naphthylsalicylate, phenylbutazolone, oxyphenbutazolone, indomethacin, sulindac, mefenamic acid, meclofenamate sodium, tolmetin, ibuprofen, naproxen, fenoprofen and piroxicam.

For the purposes of this specification, antibacterial agents are intended to include the broad classes of penicillins, cephalosporins and other beta-lactams, aminoglycosides, quinolones, macrolides, tetracyclines, sulfonamides, lincosamides and polymyxins. The penicillins, in turn, are intended to include, but are not limited to penicillin G, penicillin V, methicillin, nafcillin, oxacillin, cloxacillin, dicloxacillin, floxacillin, ampicillin, ampicillin/sulbactam, amoxicillin, amoxicillin/clavulanate, hetacillin, cyclacillin, bacampicillin, carbenicillin, carbenicillin indanyl, ticarcillin, ticarcillin/clavulanate, azlocillin, mezlocillin, peperacillin, and mecillinam. The cephalosporins and other beta-lactams are intended to include, but are not limited to cephalothin, cephapirin, cephalexin, cephradine, cefazolin, cefadroxil, cefaclor, cefamandole, cefotetan, cefoxitin, ceruroxime, cefonicid, ceforadine, cefixime, cefotaxime, moxalactam, ceftizoxime, cetriaxome, ceftizoxime, cetriaxone, cephoperazone, ceftazidime, imipenem and aztreonam. The aminoglycosides are intended to include, but are not limited to streptomycin, gentamicin, tobramycin, amikacin, netilmicin, kanamycin and neomycin. The quinolones are intended to include, but are not limited to nalidixic acid, norfloxacin, enoxacin, ciprofloxacin, ofloxacin, sparfloxacin and temafloxacin. The macrolides are intended to include, but are not limited to erythomycin, spiramycin and azithromycin. The tetracyclines are intended to include, but are not limited to doxycycline, minocycline and tetracycline. The sulfonamides are intended to include, but are not limited to sulfanilamide, sulfamethoxazole, sulfacetamide, sulfadiazine, sulfisoxazole and co-trimoxazole (trimethoprim/sulfamethoxazole). The lincosamides are intended to include, but are not limited to clindamycin and lincomycin. The polymyxins (polypeptides) are intended to include, but are not limited to polymyxin B and colistin.

Alternatively, compounds of Formula I are useful in the treatment of certain cancers including nonlymphoblastic leukemias, acute myelogenous leukemia (FAB M1 and FAB M2), acute promyelocytic leukemia (FAB M3), acute myelomonocytic leukemia (FAB M4), acute monocyte leukemia (FAB M5), erythroleukemia, chronic myelogenous leukemia, chronic myelomonocytic leukemia, chronic monocytic leukemia and conditions associated with leukemia involving activity of PMN neutral proteases e.g. disseminated intravascular coagulation.

Similarly, compounds of Formula I are useful for the inhibition of proteinase 3/myeloblastin, inhibition of elastase, inhibition of proliferation of leukemia cells, inducing differentiation of leukemia cells and remission of the disease state of leukemia.

Moreover, as described above, such treatment may optionally comprise the co-administration of an agent such as a compound selected from the group consisting of epsilon-aminocaproic acid, heparin, trasylol, prednisolone, cytosine arabinoside, b-mercaptopurine, cytarabine, an anthracycline and a vitamin A derivative such as retinoic acid.

For each of the uses, the compounds of Formula (I) and optional treatment agents, may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition.to the treatment of warm-blooded animals such as mice, rats, horses, dogs, cats, etc., the compounds of the invention are effective in the treatment of humans.

For treatment as described above the compounds of Formula (I) may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example polyoxyethylene sorbitan monooleate. The said aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution glucose in water and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula (I) may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the anti-inflammatory agents are employed.

The amount of active ingredient(s) that may be combined with the carrier materials to produce a single dosage form will vary depending upon the host treated and the particular mode of administration. For example, a formulation intended for the oral administration of humans may contain from 5 mg to 2000 mg or 5000 mg of each active agent(s) compounded with an appropriate and convenient amount of carrier material which may vary from about 5 to about 95 percent of the total composition. For purposes of this specification, this broad dosage range is specifically intended to include, but is not limited to, range of 5 mg to 2000 mg; 25 mg to 2000 mg; 5 mg to 1000 mg; 25 mg to 1000 mg; 5 mg to 500 mg; and 25 mg to 500 mg. Dosage unit forms will generally contain between from about 25 mg to about 500 mg of active ingredient(s).

Furthermore, it is also possible that most effective treatment may warrent administration of an initial dosage of one range (e.g. 1–5 mg of active agent per kg of patient weight) followed by administration of a second range (e.g. 0.1 to 1 mg of active agent per kg of pateint weight).

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The compounds of the present invention can be prepared by, but are not limited to, the general routes as outlined in Schemes 1–9. The starting carboxylic acids (5, Scheme 2) can be prepared as described in EPO 337 549 using racemic (4S,4R)-3,3-diethyl-4-[(4-substituted)phenoxy]azetidin-2-one and a chiral, substituted (R)-α-allyl- or alkyl-benzyl isocyanate, separation of the urea diastereomers by chromatography, hydrogenation to reduce the allyl if required, and/or desterification. As also described in EPO 337 549, chiral (4S)-3,3-diethyl-4-[(4-benzyloxycarbonylmethyl)phenoxy]-azetidin-2-one can be prepared by resolution of its corresponding acid and reesterification. This can be used either with a chiral isocyanate, so as to avoid the chromatographic separation of the urea diastereomers, or with racemic isocyanates followed by separation of the diastereomers. Alternatively, chiral (4S)-3,3-diethyl-4-[(4-benzyloxycarbonyl)phenoxy]azetidin-2-onecan be prepared as shown in Scheme 1 starting with (4S,4R)-3,3-diethyl-4-acetyloxy-azetidin-2-one (1) and benzyl 4-hydroxybenzoate. In the presence of sodium carbonate and a catalytic amount of (+)-cinchonine as base and in toluene solvent, the resulting chiral induction affords a 4.5:1 ratio of the 4S:4R enantiomers of 3,3-diethyl-4-[(4-benzyloxycarbonyl)phenoxy]azetidin-2-one (2). This mixture can be used directly to afford a better yield of the desired (4S) product 3 with chiral isocyanates or can be further enriched by crystallization to give pure (4S)-2. Subsequent use of this material with (R)-α-allylbenzyl isocyanates affords pure 3. Hydrogenation of the allyl and benzyl ester gives the intermediate acids 4.

The acids 5 (Scheme 2) can be readily reduced to the primary alcohols 6 using borane-dimethyl sulfide. The alcohols 6 were then converted to the intermediate bromides 7 which, without isolation, were routinely reacted with an appropriate amine to afford the desired products 8. Depending upon the desired substitutions on the amine, in some instances additional reactions may be needed to further functionalize the $R_4$ and $R_5$ groups (see Scheme 4, 5, 7, 8 and 9).

In the cases where the desired product was substituted at the benzylic position with $R_6$ as in 12 (Scheme 3), the azetidinone 1 was reacted with an appropriate 4-hydroxyphenylketone to afford racemic 9. Urea formation with a chiral isocyanate and separation of the diastereomers gave the (4S) products 10. Sodium borohydride reduction of the ketone gave the secondary alcohols 11, which again on conversion to the bromides and reaction with an appropriate amine afforded the desired products 12.

Since the above Scheme 3 afforded diastereomeric mixtures at the substituted benzyl position ($R_6$), the chiral synthesis of each methyl derivative (12, $R_6$=Me) was accomplished as shown in Scheme 4 for the (S) derivative. (S)- or (R)-(−)-α-Methylbenzylamine were used as starting materials and were nitrated according to the procedure of C. W. Perry, et. al., *Synthesis* 1977, 492. Protection of the amine as the CBZ derivative gave 13 which was then alkylated with methyl iodide/sodium hydride to afford 14. Reduction of the 4-nitro group with stannous chloride afforded the aniline 15 which was directly diazotized with sodium nitrite and converted to the phenol 16. Reaction with azetidinone 1 as above afforded 17 which was acylated with (R)-α-allyl-(4-methyl)benzyl isocyanate to give the urea 18 as the higher $R_f$ diastereomer. Reduction of the allyl and removal of the CBZ was done by hydrogenation and acylation with methoxyacetyl chloride gave the amide 19. This was reduced to the desired product 20 with borane-dimethyl sulfide.

As shown in Scheme 5, when $R_5$ contains a sulfide moiety as in structure 21, this could be selectively oxidized to both sulfoxide or sulfone derivatives 22.

Compounds wherein the $R_6$ group was substituted with an α-methoxy group were prepared as in Scheme 6. Starting with 4-hydroxy-α-methoxyacetophenone (prepared according to Shetty, H. U.; Nelson, W. L. *J. Ned. Chem.* 1988, 31, 55–58) and using the above methods, the urea 23 was prepared. Hydrogenation with 5% Ru/C reduced the allyl as well as the ketone to give the secondary alcohol 24. Conversion to the bromide and displacement with an appropriate amine afforded the desired products 25.

Compounds in which the $R_6$ and $R_5$ groups are connected in a pyrrolidine ring were prepared as in Scheme 7. The phenol 26 was prepared starting with 4-benzyloxymethylbenzaldehyde. Reaction with potassium cyanide and morpholine gave the aminonitrile which was then alkylated with acrylonitrile, hydrolyzed back to the ketone and debenzylated to give 26. This phenol was converted to the urea 27 as described above. Hydrogenation of 27 in the presence of Raney nickel reduced the allyl and nitrile and, through an internal reductive amination, gave the pyrrolidine product 28 all in one step. Alkylation with 2-methoxyethyl bromide afforded the desired product 29.

Schemes 8 and 9 show alternate routes to certain substituted amine derivatives after the formation of the benzyl amine. Thus, the bromide 7 (n=1, $R_7$=H) was reacted with methylamine to give the secondary amine 30. This could be alkylated, for example with 2-methoxyethyl bromide, to afford the desired tertiary amines, such as 31. Similarly, reaction of 7 with 2-hydroxyethylmethylamine gave the amino-alcohol 32 which could be reaced with a variety of acylating agents, such as with dimethylcarbamyl chloride, to give 33.

As shown in Scheme 10 bromide 7 can also be reacted with sodium azide, which upon hydrogenation yields the primary amine 34 (Scheme 10). This amine can be used to produce a series of secondary amides through reaction with a variety of activated acylating agents. For example, acylation with acetic anhydride gave the acetamide 35 (Scheme 11), while acylation with various isocyanates yeilded ureas such as 36 (Scheme 12). Similarly, coupling to activated amino acids gave compounds such as 37 (Scheme 13).

SCHEME 1

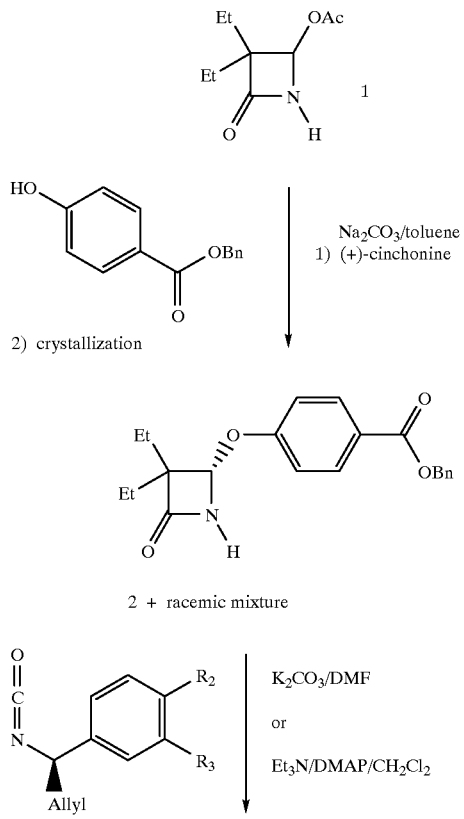

SCHEME 2

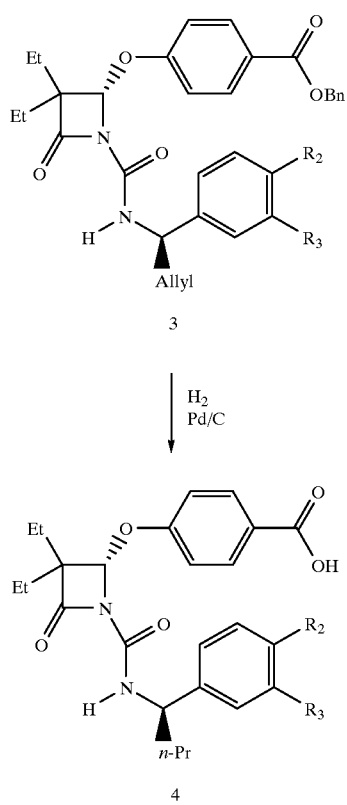

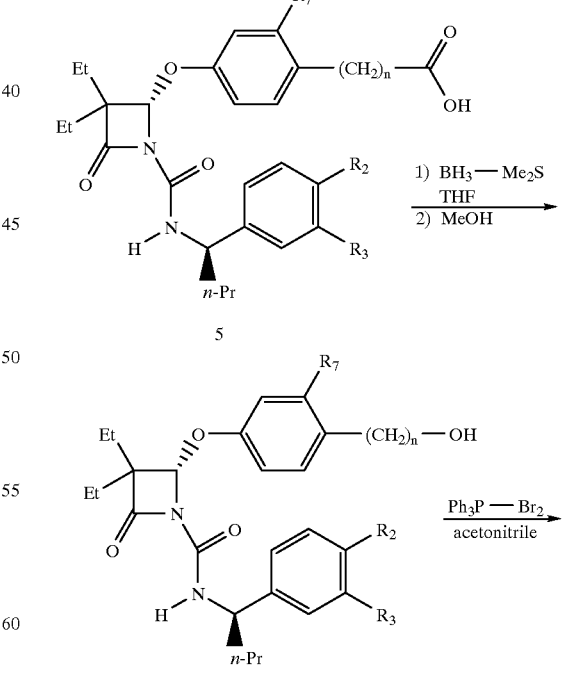

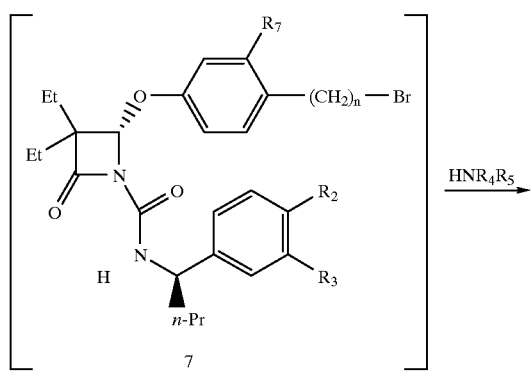
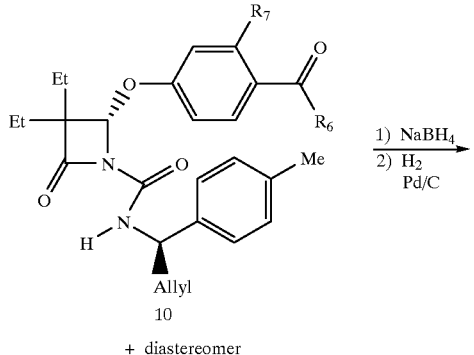
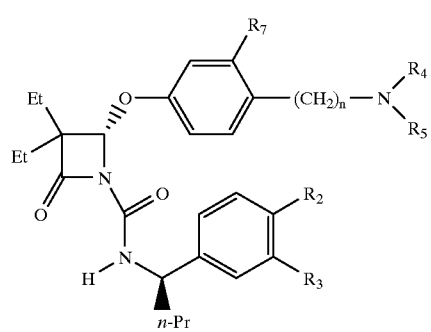
n = 0-5
R_7 = H, Me, Cl, OMe
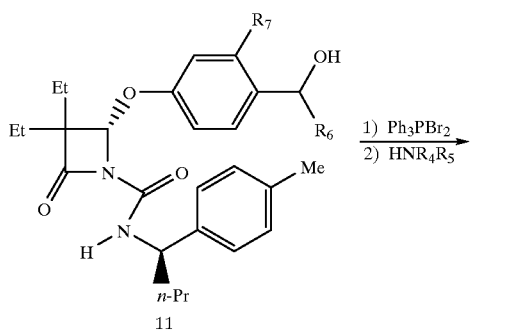
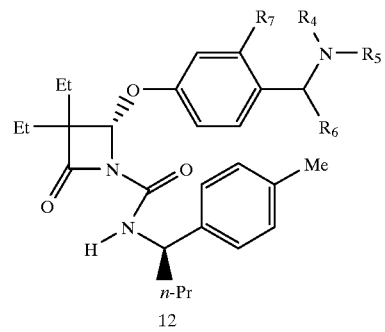
SCHEME 3
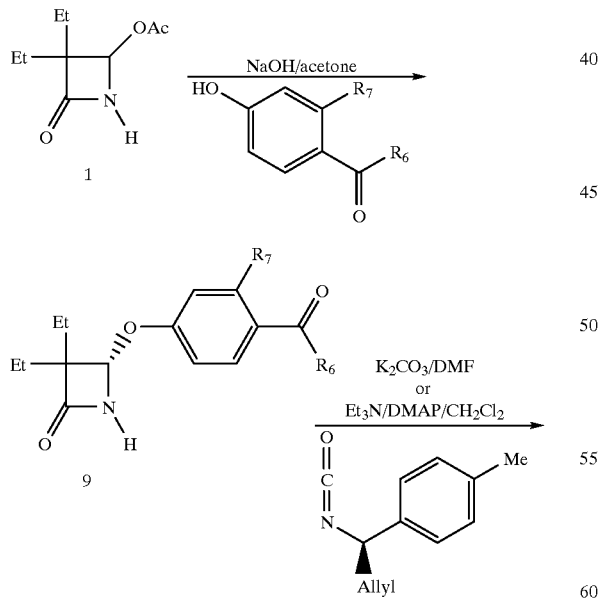

SCHEME 4
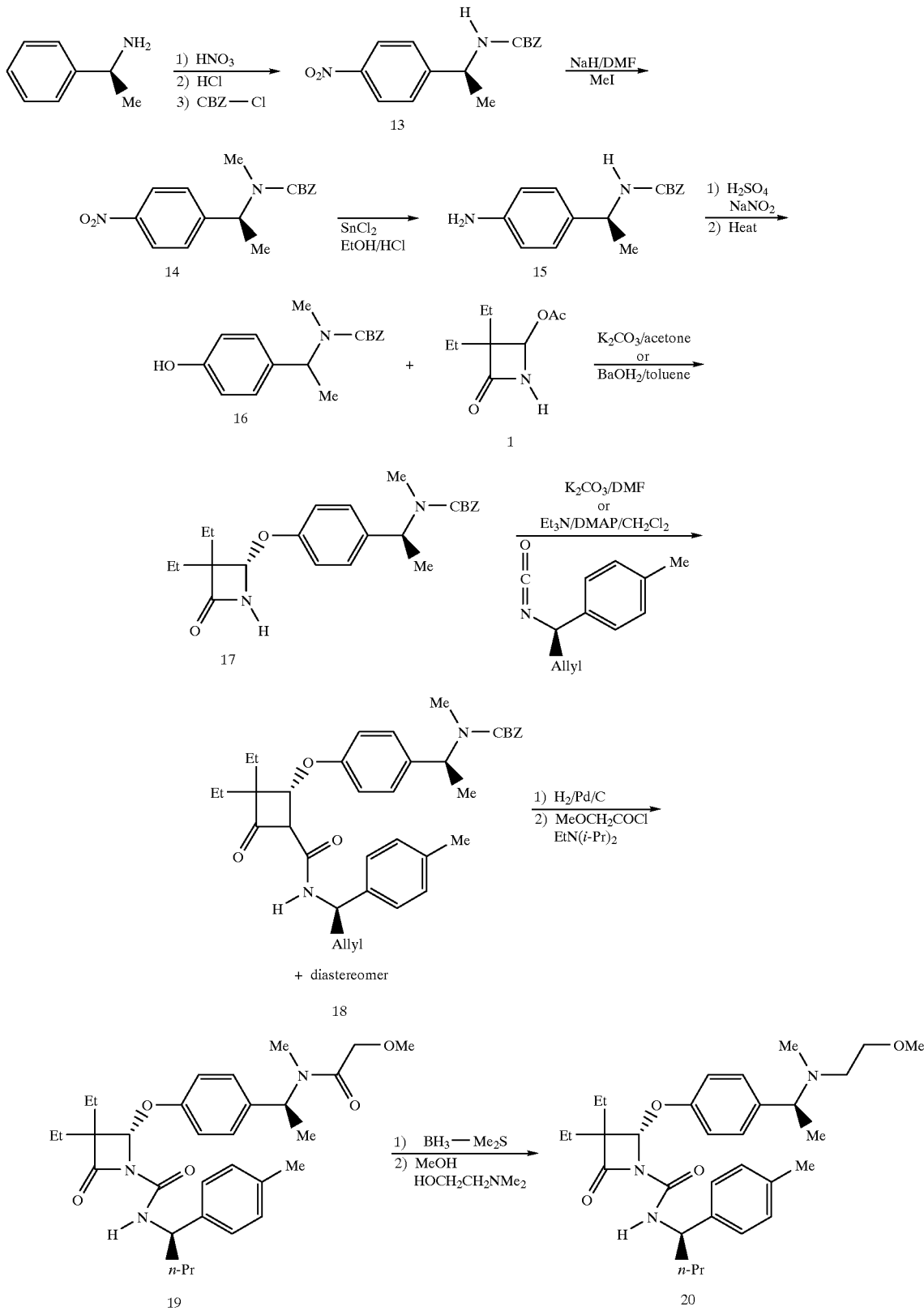

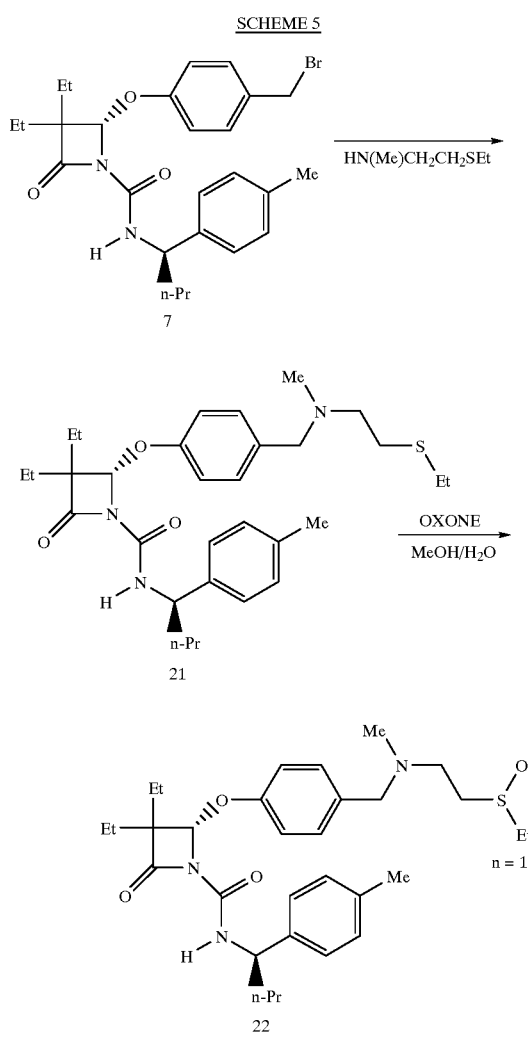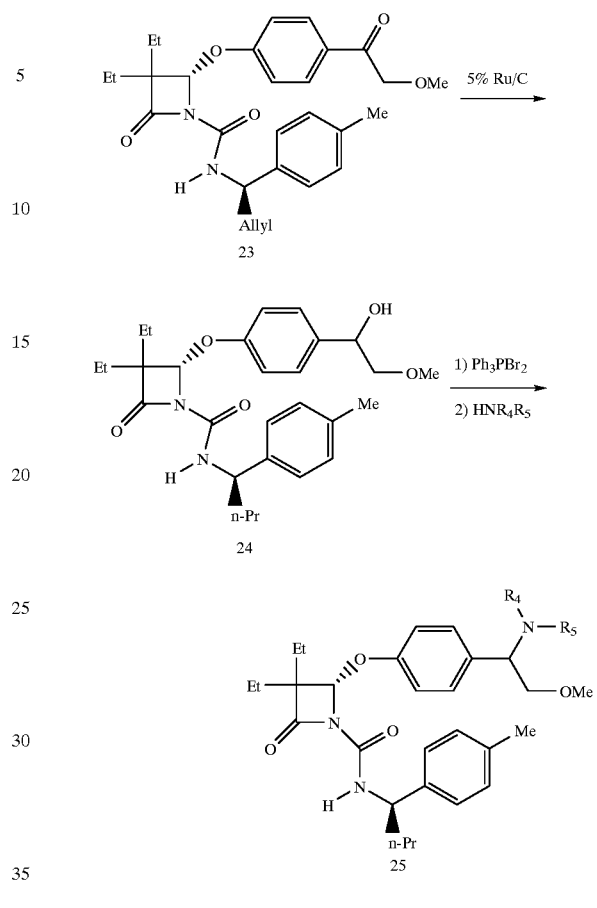

29
-continued
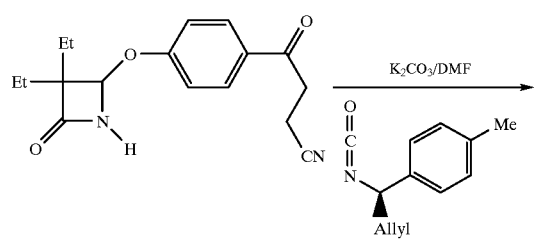
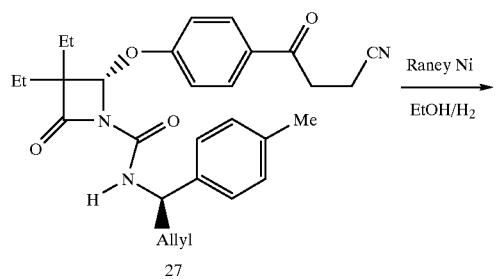
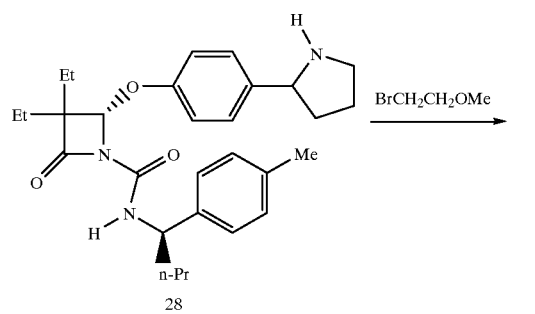
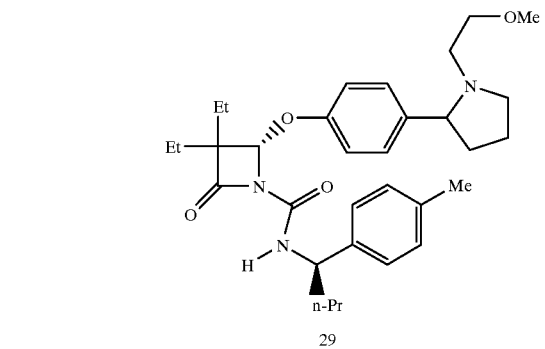
SCHEME 8
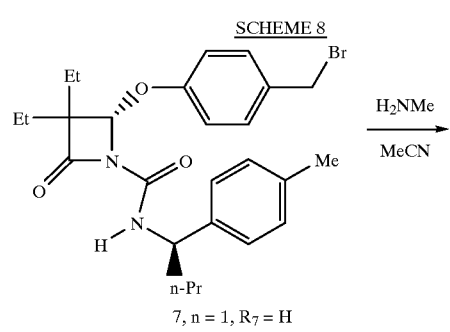
30
-continued
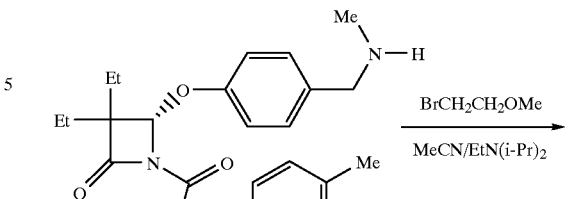
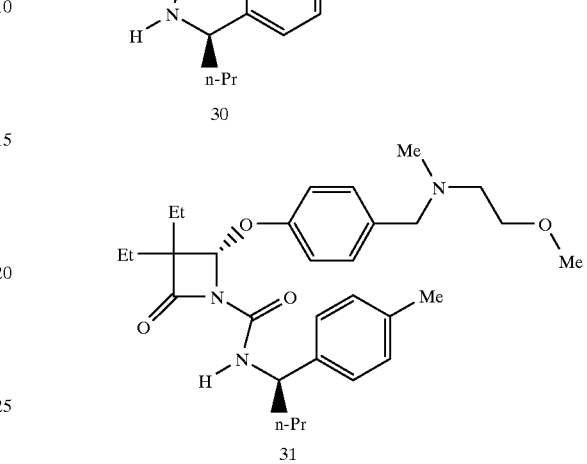
SCHEME 9
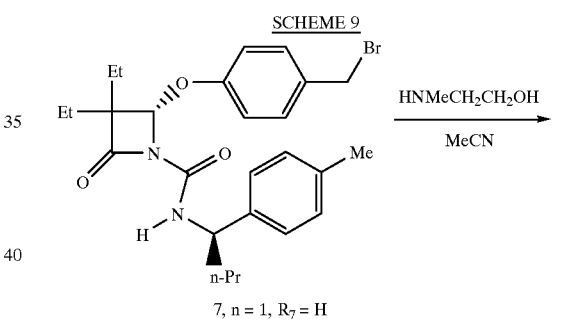
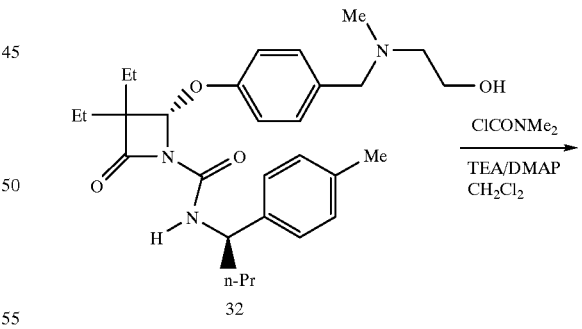

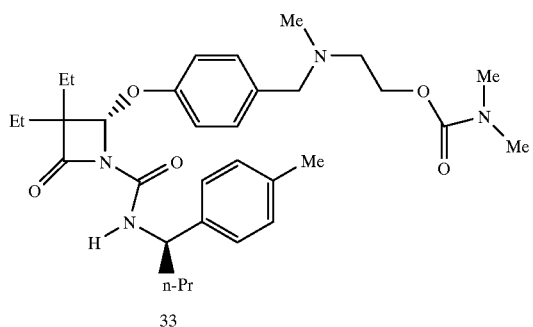
33
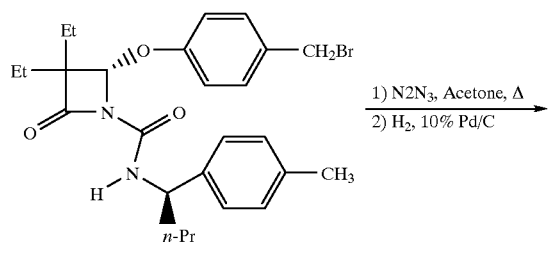
7, n = 1, R7 = H
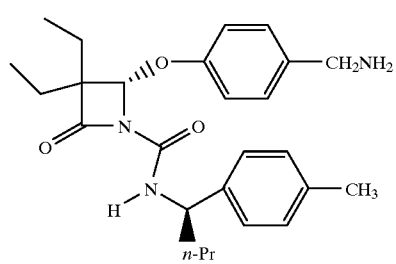
34
SCHEME 11
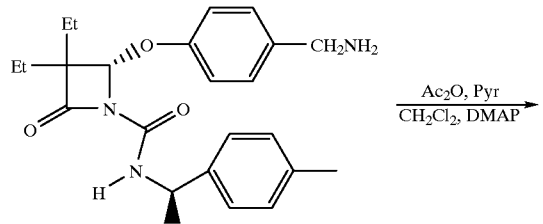
34
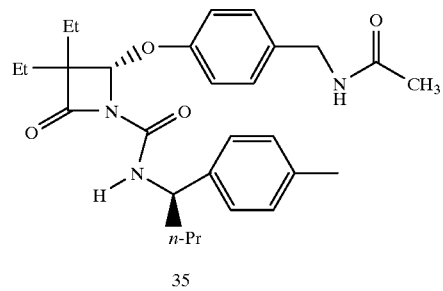
35
SCHEME 12
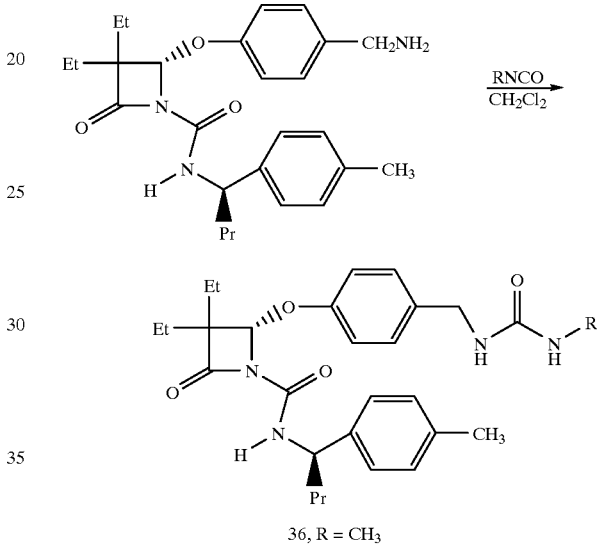
36, R = CH3
SCHEME 13
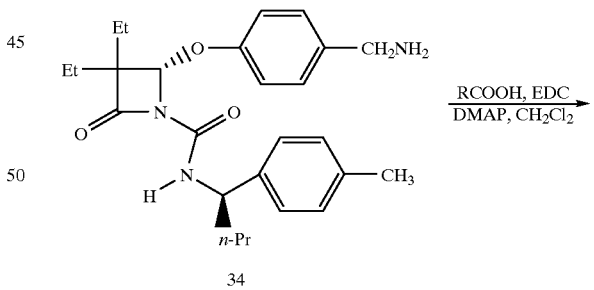
34

-continued

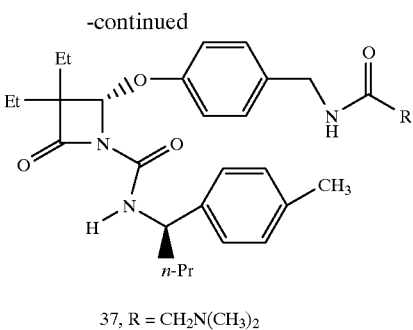

37, R = CH$_2$N(CH$_3$)$_2$

EXAMPLE 1

(4S)-3,3-Diethyl-1-[(R)-α-n-propyl-(4-methyl) benzylamincarbonyl]-4-[(4-carboxy)phenoxy] azetidin-2-one Method A:

The title compound can be prepared as previously described (see EPO 337 549) using racemic (4S,4R)-3,3-diethyl-4-[(4-t-butoxycarbonyl)phenoxy]-azetidin-2-one and (R)-α-allyl-4-methylbenzyl isocyanate, separation of the diastereomers by chromatography, hydrogenation to reduce the allyl, and removal of the t-butyl ester with triflouroacetic acid (TFA).

Method B:

Step A: Preparation of (4S)-3,3-diethyl-4-[(4-benzyloxycarbonyl)phenoxy]azetidin-2-one A suspension of benzyl 4-hydroxybenzoate (27.7 gm, 0.12 mol), 3,3-diethyl-4-acetyloxy-azetidin-2-one (30 gm, 0.16 mol), sodium carbonate (17 gm, 0.16 mol), and (+)-cinchonine (4.7 gm, 0.016 mol) in toluene (750 mL) was stirred at 55° C. for 3 days. At this time additional aliquots of azetidinone (4 gm), sodium carbonate (5 gm) and (+)-cinchonine (4.7 gm) were added and the reaction was stirred for another 2 days. The reaction was then cooled and filtered through Celite, and the filter cake washed with ether. The filtrate was diluted with ether, poured into ice water and acidified with 2N HCl. The ether layer was washed with brine and the aqueous layers back-extracted with another 2 portions of ether. The pooled ether layers were dried over sodium sulfate and concentrated. The residue solidified on standing and was then recrystallized from 1:1 ether:hexanes (200 mL) to give 26 gm (61%) of the title compound as a white solid, [α]$_D$=−65 (EtOH). This material was a 4.5:1 mixture of 4S:4R enantiomers and could be used directly in Step B. Further enrichment in the 4S enantiomer could be achieved by recrystallization from ethyl acetate (100 mL) to afford 12.0 gm (28%) of material containing only 2–3% of the 4R enantiomer, [α]$_D$=−96 (EtOH).

Step B: Preparation of (4S)-3,3-diethyl-1-[(R)-α-allyl-(4-methyl)benzylaminocarbonyl]-4-[(4-benzyloxycarbonyl)phenoxy]azetidin-2-one A solution of (4S)-3,3-diethyl-4-[(4-benzy-loxycarbonyl)phenoxy]azetidin-2-one (39 gm, 0.11 mol), (R)-α-allyl-4-methylbenzyl isocyanate (31 gm, 0.165 mol), DMAP (1.34 gm, cat), and triethylamine (TEA) in methylene chloride (100 mL) was heated under N$_2$ at 45° C. for 16 hrs. The reaction was diluted with methylene chloride and poured into ice water containing 1.2N HCl and the layers were separated. The aqueous layer was reextracted with methylene chloride and the combined methylene chloride layers were washed with water, then brine, dried over sodium sulfate and evaporated. The residue was crystallized from methylene chloride/hexanes to afford 39.3 gm (66%) of the title compound. Chromatography of the mother liquor or material derived from less enantiomerically pure starting material affords the pure title compound as the higher R$_f$ isomer.

NMR (CDCl$_3$; δ from TMS): 0.96, 1.05 (2 t, J=8 Hz, 6H), 1.8–2.1 (m, 4H), 2.33 (s, 3H), 2.57 (t, J=7 Hz, 2H), 4.84 (q, J=8 Hz, 1H), 5.0–5.2 (m, 2H), 5.37 (s, 2H), 5.60 (s, 1H), 5.6–5.8 (m, 1H), 7.01 (d, J=8 Hz, 1H), 7.18 (br s, 5H), 7.2–7.5 (m, 4H), 8.04 (d, J=9 Hz, 2H).

Step C: Preparation of (4S)-3,3-diethyl-1-[(R)-α-n-propyl-(4-methyl)benzylaminocarbonyl]-4-[(4-carboxy)-phenoxy] azetidin-2-one Material from Step B (31.9 gm) was dissolved in methanol (300 mL) and was hydrogenated over 10% Pd/C (1.5 gm) at 40 p.s.i. for 2 hrs. The reaction was filtered, concentrated in vacuo and crystallized from ethanol/water to give 27.8 gm (100%) of the title compound.

NMR (CDCl$_3$; δ from TMS): 0.91, 0.96, 1.07 (3 t, J=8 Hz, 9H),1.2–1.5 (m, 2H), 1.8–2.1 (m, 6H), 2.34 (s, 3H), 4.84 (q, J=8 Hz, 1H), 5.72 (s, 1H), 6.94 (d, J=8 Hz, 1H), 7.17 (br s, 4H), 7.24 (d, J=9 Hz, 2H), 8.02 (d, J=9 Hz, 2H).

EXAMPLE 2

(4S)-3,3-Diethyl-1-[(R)-α-n-propyl-(4-methyl) benzyl-aminocarbonyl]-4-[(4-carboxymethyl) phenoxy]azetidin-2-one The title compound can be prepared as previously described (see EPO 337 549).

EXAMPLE 3

(4S)-3,3-Diethyl-1-[(R)-α-n-propyl-(4-methyl) benzyl-aminocarbonyl]-4-[(4-hydroxymethyl) phenoxy]azetidin-2-one A solution of (4S)-3,3-diethyl-1-[(R)-α-n-propyl(4-methyl)benzylaminocarbonyl]-4-[(4-carboxy)-phenoxy] azetidin-2-one (10 gm, 22 mmol) in THF (150 mL) was cooled in an ice bath under nitrogen and a 2M solution of borane-methyl sulfide in THF (30 mL, 60 mmol) was added over 5 min. The reaction was then stirred at rt for 16 hrs and then quenched by slow addition of methanol (50 mL). The volatiles were removed in vacuo and the residue flash chromatographed using 25% ethyl acetate/hexanes to give 8.8 gm (84%) of the title compound as a viscous oil.

NMR (CDCl$_3$; δ from TMS): 0.90, 0.93, 1.07 (3 t, J=8 Hz, 9H),1.2–1.5 (m, 2H), 1.8–2.1 (m, 6H), 2.34 (s, 3H), 4.65 (br s, 2H), 4.85 (q, J=8 Hz, 1H), 5.59 (s, 1H), 6.97 (d, J=8 Hz, 1H), 7.1–7.4 (m, 8H).

EXAMPLE 4

Starting with the appropriate substituted benzoic acid derivative (see EPO 337 549) and using the procedure of Example 3, the following substituted benzyl alcohols were prepared:

(a) (4S)-3,3-Diethyl-1-[(R)-α-n-propyl-(4-methyl)-benzylaminocarbonyl]-4-[(4-hydroxymethyl)-3-methyl-phenoxy]azetidin-2-one.

(b) (4S)-3,3-Diethyl-1-[(R)-α-n-propyl-(4-methyl)-benzylaminocarbonyl]-4-[(4-hydroxymethyl)-3-methoxy-phenoxy]azetidin-2-one.

(c) (4S)-3,3-Diethyl-1-[(R)-α-n-propyl-(4-methyl)-benzylaminocarbonyl]-4-[(4-hydroxymethyl)-3-chloro-phenoxy]azetidin-2-one.

(d) (4S)-3,3-Diethyl-1-[(R)-α-n-propyl-(4-methoxy)-benzylaminocarbonyl]-4-[(4-hydroxymethyl)phenoxy]-azetidin-2-one.

(e) (4S)-3,3-Diethyl-1-[(R)-α-n-propyl-(4-ethoxy)-benzylaminocarbonyl]-4-[(4-hydroxymethyl)-3-fluoro-phenoxy]-azetidin-2-one.
(f) (4S)-3,3-Diethyl-1-[(R)-α-n-propyl-(4-methyl)-benzylaminocarbonyl]-4-[(4-hydroxymethyl)phenoxy]-azetidin-2-one.
(g) (4S)-3,3-Diethyl-1-[(R)-α-n-propyl-(3,4-dioxomethylene)benzylaminocarbonyl]-4-[(4-hydroxymethyl)-phenoxy]azetidin-2-one.
(h) (4S)-3,3-Diethyl-1-[(R)-α-n-propyl-(4-methyl)-benzylaminocarbonyl]-4-[(4-hydroxymethyl)-3,5-dimethylphenoxy]azetidin-2-one.
(i) (4S)-3,3-Diethyl-1-[(R)-[1-(benzofuran-5-yl)-butyl]aminocarbonyl]-4-[(4-hydroxymethyl)phenoxy]-azetidin-2-one.

EXAMPLE 5

(4S)-3,3-Diethyl-1-[(R)-α-n-propyl-(4-methyl)benzyl-aminocarbonyl]-4-[(4-(2-hydroxyethyl)phenoxy]azetidin-2-one Starting with (4S)-3,3-diethyl-1-[(R)-α-n-propyl(4-methyl)benzylaminocarbonyl]-4-[(4-carboxy-methyl)phenoxy]azetidin-2-one and using the procedure of Example 3, (4S)-3,3-diethyl-1-[(R)-α-n-propyl-(4-methyl)benzylaminocarbonyl]-4-[(4-(2-hydroxyethyl)-phenoxy]azetidin-2-one was prepared.

NMR (CDCl$_3$; δ from TMS): 0.90, 0.93, 1.07 (3 t, J=8 Hz, 9H),1.2–1.5 (m, 2H), 1.6–2.1 (m, 6H), 2.34 (s, 3H), 2.82 (t, J=7 Hz, 2H), 3.84 (br t, J=7 Hz, 2H), 4.83 (q, J=8 Hz, 1H), 5.57 (s, 1H), 6.96 (d, J=8 Hz, 1H), 7.1–7.25 (br s, 8H).

EXAMPLE 6

(4S)-3,3-Diethyl-1-[(R)-α-n-propyl-(4-methyl)benzyl-aminocarbonyl]-4-[(4-(2-methoxyethyl)ethylamino-methyl)phenoxy]azetidin-2-one Step A: (4S)-3,3-Diethyl-1-[(R)-α-n-propyl-(4-methyl)benzylaminocarbonyl]-4-[(4-bromo-methyl)phenoxy]azetidin-2-one Bromine was added dropwise to a solution of triphenylphosphine (175 mg, 0.68 mmol) in THF (10 mL) until the color persisted and then just enough additional triphenyl phosphene was added to discharge the color. After 5 min (4S)-3,3-diethyl-1-[(R)-α-n-propyl-(4-methyl)benzylaminocarbonyl]-4-[(4-hydroxy-methyl)phenoxy]azetidin-2-one (250 mg, 0.57 mmol) (prepared in Example 3) in 2 mL of THF was added and the reaction was stirred at rt for 1 hr. At this time TLC (20% ethyl acetate/hexanes) indicated complete conversion to the higher $R_f$ bromide. This solution was routinely used without isolation of the reactive bromide.

Step B: (4S)-3,3-Diethyl-1-[(R)-α-n-propyl-(4-methyl)benzylaminocarbonyl]-4-[(4-(2-methoxy-ethyl)ethylaminomethyl)phenoxy]azetidin-2-one N-(2-Methoxyethyl)ethylamine (200 mg, 1.9 mmol) and triethylamine (0.016 mL, 1.1 mmol) were added to the above solution of (4S)-3,3-diethyl-1-[(R)-α-n-propyl-(4-methyl)benzylaminocarbonyl]-4-[(4-bromomethyl)phenoxy]azetidin-2-one (0.57 mmol). The reaction was stirred at rt for another 3 hrs and then diluted with ether and washed with potassium carbonate solution and brine. The aqueous layers were consecutively extracted with another portion of ether and the pooled ether layers were dried over sodium sulfate and evaporated. The residue was purified by preparative TLC eluting with 40% ethyl acetate/hexanes to give 175 mg (55%) of the title compound as an oil.

NMR (CDCl$_3$; δ from TMS): 0.91, 0.94, 1.04, 1.08 (4 t, J=8 Hz, 12H), 1.2–1.5 (m, 2H), 1.6–2.1 (m, 6H), 2.34 (s, 3H), 2.55 (q, J=8 Hz, 2H), 2.64 (t, J=6 Hz, 2H), 3.35 (s, 3H), 3.60 (t, J=6 Hz, 2H), 3.58 (s, 2H), 4.85 (q, J=8 Hz, 1H), 5.57 (s, 1H), 6.95 (d, J=8 Hz, 1H), 7.1–7.25 (m, 8H).

EXAMPLE 7

Starting with (4S)-3,3-diethyl-1-[(R)-α-n-propyl-(4-methyl)benzylaminocarbonyl]-4-[(4-hydroxymethyl)phenoxy]azetidin-2-one prepared in Example 3 and using the procedure of Example 6, but using the corresponding substituted amine, the compounds listed in the following table were prepared.

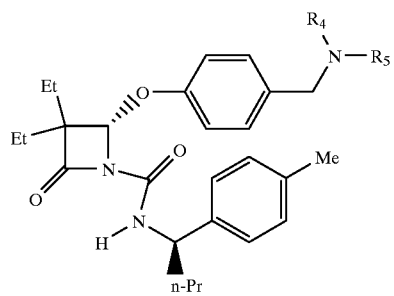

| $R_4$ | $R_5$ |
|---|---|
| Me | Bn |
| —CH$_2$CH$_2$OCH$_2$CH$_2$— | |
| Me | Me |
| —CH$_2$CH$_2$N(i-Pr)CH$_2$CH$_2$— | |
| —CH$_2$CH$_2$N(Ac)CH$_2$CH$_2$— | |
| —CH$_2$CH$_2$N(Bz)CH$_2$CH$_2$— | |
| Me | CH$_2$CH$_2$CO$_2$H—TFA |
| Me | CH$_2$CH$_2$OH |
| —CH$_2$CHMeNCHMeCH$_2$— | |
| —CHMeCH$_2$CH$_2$CHMe— | |
| Me | CH$_2$CH$_2$NMe$_2$ |
| Me | CH$_2$CH$_2$N(Me)Bn |

-continued

[Structure: azetidinone with Et, Et substituents at 3-position; 4-position bears O-linked para-substituted phenyl with CH2-N(R4)(R5); N1 bears C(=O)-NH-CH(n-Pr)-(4-methylphenyl)]

| R4 | R5 |
|---|---|
| —CHCHNCH— | |
| Me | CH$_2$CH$_2$OCONMe$_2$ |
| Me | CH$_2$CH$_2$CONMe$_2$ |
| —CH$_2$CH$_2$N(CO$_2$Me)CH$_2$CH$_2$— | |
| Me | CH$_2$CH$_2$OMe |
| —CH$_2$CH$_2$N(CONMe$_2$)CH$_2$CH$_2$— | |
| Me | CH$_2$CH$_2$OCONHMe |
| —CHCHNCMe— | |
| —CH$_2$CH$_2$N(CONEt$_2$)CH$_2$CH$_2$— | |
| Me | CH$_2$CH$_2$N(Me)CONMe$_2$ |
| Me | i-Pr |
| i-Pr | CH$_2$CH$_2$OMe |
| Me | CH$_2$CH$_2$N(Me)Ac |
| Et | CH$_2$CH$_2$OMe |
| Me | CH$_2$CH$_2$N(Me)COOMe |
| —CHMeCH$_2$CH$_2$CH$_2$CHMe— | |
| Me | CH$_2$CH$_2$OEt |
| Me | CH$_2$CH$_2$OCOCMe$_3$ |
| Me | CH$_2$CH$_2$OCOCHMe$_2$ |
| Me | CH$_2$CH$_2$OPh |
| Me | CH$_2$CH$_2$OCONEt$_2$ |
| —CHCHNCEt— | |
| —CHCMeNCMe— | |
| Me | CH$_2$CH$_2$OCONH(i-Pr) |
| Me | CH$_2$CH$_2$OCON(CH$_2$CH$_2$OCH$_2$CH$_2$) |
| Me | CH$_2$CH$_2$OCON(Me)n-Bu |
| Me | CH$_2$CON(n-Pr)$_2$ |
| Me | CH$_2$CH$_2$SEt |
| Me | CH$_2$CH(CH$_2$CH$_2$CH$_2$CH$_2$O) |
| Me | CH$_2$CH$_2$SMe |
| Et | CH$_2$CH$_2$NHAc |
| Me | CH$_2$CH(CH$_2$CH$_2$CH$_2$O) |
| —CH$_2$CH$_2$SCH$_2$— | |
| —CH$_2$CH$_2$SCH$_2$CH$_2$— | |
| —CH$_2$CH$_2$CH$_2$CH($\underline{S}$—CH$_2$OH) | |
| —CH$_2$CH$_2$CH$_2$CH($\underline{S}$—CH$_2$OMe)— | |
| —CH$_2$CH$_2$CH(OH)CH$_2$— | |
| —CH$_2$CH$_2$CH(OH)CH$_2$CH$_2$— | |
| Me | CH(Me)CH$_2$OMe |
| Et | CH$_2$CH$_2$OCONMe$_2$ |
| Me | CH$_2$CH$_2$SOEt |
| Me | CH$_2$CH$_2$SO$_2$Et |
| Me | CH$_2$CH$_2$CH$_2$OMe |
| Me | CH$_2$CH$_2$CH$_2$OCONMe$_2$ |
| Me | CH$_2$CH$_2$OCH$_2$CH$_2$OMe |
| Et | CH$_2$CH$_2$OCH$_2$CH$_2$OMe |
| Et | CH(Me)CH$_2$OMe |
| —CH$_2$CH$_2$N(COCHMe$_2$)CH$_2$CH$_2$— | |
| —CH$_2$CH$_2$CH(OMe)CH$_2$— | |
| —CH$_2$CH$_2$CH$_2$CH($\underline{R}$—CH$_2$OH)— | |
| —CH$_2$CH$_2$N(—CNCHCHCHN)CH$_2$CH$_2$— | |
| Et | CH$_2$CH$_2$SMe |

EXAMPLE 8

Starting with the appropriate benzyl alcohol prepared in Example 4 and using the procedure of Example 6, but using the corresponding substituted amine, the following compounds were prepared.

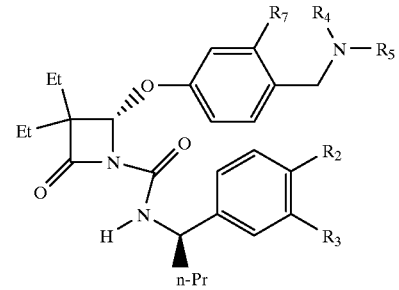

| $R_2$ | $R_3$ | $R_4$ | $R_5$ | $R_7$ |
|---|---|---|---|---|
| OMe | H | Me | $CH_2CH_2OMe$ | H |
| OEt | H | Me | $CH_2CH_2OMe$ | H |
| OEt | H | Et | $CH_2CH_2OMe$ | H |
| OMe | H | Et | $CH_2CH_2OMe$ | H |
| Me | H | Et | $CH_2CH_2OMe$ | Cl |
| Me | H | Me | $CH(Me)CH_2OMe$ | OMe |
| —$OCH_2O$— | | Et | $CH(Me)CH_2OMe$ | H |
| —$OCH_2O$— | | Et | $CH_2CH_2OMe$ | H |
| Me | H | Et | $CH_2CH_2CH_2CH_2OMe$ | OMe |
| Me | H | Et | $CH(Me)CH_2OMe$ | OMe |
| Me | H | Me | $CH_2CH_2OMeCH_2CH_2OMe$ | Cl |
| Me | H | Me | $CH_2CH_2OMe$ | Cl |
| Me | H | Me | $CH(Me)CH_2OMe$ | Cl |
| Me | H | Me | $CH_2CH_2OMe$ | 3,5-$Me_2$ |
| Me | H | Me | $CH_2CH_2OMe$ | Me |
| Me | H | Et | $CH_2CH_2OMe$ | Me |
| Me | H | Et | $CH(Me)CH_2OMe$ | Me |
| —OCHCH— | | Et | $CH(Me)CH_2OMe$ | H |
| —OCHCH— | | Et | $CH_2CH_2OMe$ | H |
| —$OCH_2O$— | | Et | $CH_2CH_2OMe$ | H |
| —$OCH_2O$— | | H | cyclopropyl | H |
| —$OCH_2O$— | | $CH_2CH_2N(COMe_2)CH_2CH_2$ | | H |

EXAMPLE 9

Starting with (4S)-3,3-diethyl-1-[(R)-α-n-propyl-(4-methyl)benzylaminocarbonyl]-4-[(4-(2-hydroxyethyl)-phenoxy]azetidin-2-one as prepared in Example 5 and using the procedure of Example 6, but using the corresponding substituted amine, the following compounds were prepared.
(a) (4S)-3,3-Diethyl-1-[(R)-α-n-propyl-(4-methyl) benzylaminocarbonyl]-4-[(4-(2-dimethylamino)ethyl) phenoxy]azetidin-2-one.
(b) (4S)-3,3-Diethyl-1-[(R)-α-n-propyl-(4-methyl) benzylaminocarbonyl]-4-[(4-(2-benzylmethylamino) ethyl)phenoxy]azetidin-2-one.
(c) (4S)-3,3-Diethyl-1-[(R)-α-n-propyl-(4-methyl) benzylaminocarbonyl]-4-[(4-(2-(4-morpholino))ethyl) phenoxy]azetidin-2-one.
(d) (4S)-3,3-Diethyl-1-[(R)-α-n-propyl-(4-methyl) benzylaminocarbonyl]-4-[(4-(2-((2-dimethylamino) ethyl)methylamino)ethyl)phenoxy]azetidin-2-one.

EXAMPLE 10

(4S)-3,3-Diethyl-1-[(R)-α-n-propyl-(4-methyl) benzylaminocarbonyl]-4-[(4-((2-thioethyl)ethyl) methylaminomethyl)phenoxy]azetidin-2-one, S-oxide A solution of (4S)-3,3-diethyl-1-[(R)-α-n-propyl-(4-methyl)benzylaminocarbonyl]-4-[(4-((2-thioethyl)ethyl) methylaminomethyl)phenoxy]azetidin-2-one (100 mg, 0.185 mmol) in methanol (4 mL) was cooled in an ice bath and a solution of Oxone® (74 mg, 0.12 mmol) in water (4 mL) was added. After 15 min, TLC (50% ethyl acetate/50% hexanes) indicated complete reaction. The reaction was diluted with water and extracted 3 times with chloroform. The combined organic layers were washed with brine, dried over sodium sulfate and evaporated. The residue was purified using flash chromatography (50% acetone/50% hexanes) to afford 73 mg (70%) of the title compound.

Mass Spectrum (FAB): m/Z 555 ($M^+$+1).

EXAMPLE 11

(4S)-3,3-Diethyl-1-[(R)-α-n-propyl-(4-methyl) benzylaminocarbonyl]-4-[(4-((2-thioethyl)ethyl) methylaminomethyl)phenoxy]azetidin-2-one. S-dioxide.

Using exactly the same procedure as in Example 10, but using more oxone (148 mg, 0.24 mmol), 43 mg (40%) of the title compound was prepared.

Mass Spectrum (FAB): m/Z 571 ($M^+$+1).

EXAMPLE 12

(4S)-3,3-Diethyl-1-[(R)-α-n-propyl-(4-methyl) benzylaminocarbonyl]-4-[(R,S)-4-((1-(2-methoxyethyl)methylamino)ethyl)phenoxy]azetidin-2-one Step A: (4R,S)-3,3-Diethyl-4-[(4-acetyl)phenoxy]azetidin-2-one To a solution of (4R,S)-3,3-diethyl-4-acetoxyazetidin-2-one (14.7 gm, 74 mmol) and 4-hydroxyacetophenone (5.0 gm, 37 mmol) in acetone (50 mL) was added a solution of potassium carbonate (10.2 gm, 74 mmol) in water (50 mL). The reaction was stirred at rt for 3 hrs and then poured into a mixture of ether, ice water and 15 mL of 2N hydrochloric acid. The layers were separated and the ether layer was washed with water and brine and the aqueous layers were consecutively extracted with a second portion of ether and the pooled ether layers were dried and evaporated. The residue was purified by preparative chromatography using 35–60% ethyl acetate/hexanes to give 9.5 gm (98%) of title compound.

NMR (CDCl$_3$; δ from TMS): 1.06, 1.07 (2 t, J=8 Hz, 6H), 1.7–2.1 (m, 4H), 2.56 (s, 3H), 5.47 (s, 1H), 6.7 (br s, 1H), 6.91 (d, J=8 Hz, 2H), 7.95 (d, J=8 Hz, 2H).

Step B: (4S)-3,3-Diethyl-1-[(R)-α-allyl-(4-methyl) benzylaminocarbonyl]-4-[(4-acetyl)phenoxy]azetidin-2-one A solution of (4R,S)-3,3-diethyl-4-[(4-acetyl)phenoxy]-azetidin-2-one (4.0 gm, 15 mmol), (R)-α-allyl-(4-methyl) benzyl isocyanate (4.3 gm, 23 mmol), triethylamine (4.2 mL, 30 mmol) and a catalytic amount of DMAP in methylene chloride (10 mL) was heated at 50° C. for 16 hrs. The reaction was diluted with methylene chloride and washed with dilute hydrochloric acid and brine. The aqueous layers were back-extracted with another portion of methylene chloride and the combine layers dried over sodium sulfate and evaporated. The residue was purified by preparative chromatography using 20% ethyl acetate/80% hexanes to give 2.5 gm (37%) of pure title compound as the higher $R_f$ isomer.

NMR (CDCl$_3$; δ from TMS): 0.98, 1.07 (2 t, J=8 Hz, 6H), 1.7–2.1 (m, 4H), 2.34 (s, 3H), 2.56 (s, 3H), 2.57 (br t, J=6–7 Hz, 2H), 4.93 (q, J=8 Hz, 1H), 4.1–4.2 (m, 2H), 5.6–5.8 (m and s, 4H), 6.98 (br d, J=8 Hz, 1H), 7.15 (s, 4H), 7.23 (d, J=8 Hz, 2H), 7.92 (d, J=8 Hz, 2H).

Step C: (4S)-3,3-Diethyl-1-[(R)-α-n-propyl-(4-methyl) benzylaminocarbonyl]-4-[(4-acetyl)phenoxy]azetidin-2-one A solution of (4S)-3,3-diethyl-1-[(R)-α-allyl-(4-methyl) benzylaminocarbonyl]-4-[(4-acetyl)phenoxy]azetidin-2-one (1.3 gm, 2.9 mmol) and 100 mg of 10% palladium on carbon in ethanol (15 mL) was hydrogenated at 40 p.s.i. for 20 min. The reaction was then filtered and evaporated to afford 1.3 gm (quantitative) of clean title compound without further purification.

NMR (CDCl$_3$; δ from TMS): 0.92, 0.97, 1.08 (t, J=8 Hz, 9H), 1.2–1.4 (m, 2H), 1.6–2.0 (m, 6H), 2.35 (s, 3H), 2.56 (s, 3H), 4.82 (q, J=8 Hz, 1H), 5.68 (s, 1H), 6.91 (d, J=8 Hz, 1H), 7.16 (s, 4H), 7.24 (d, J=8 Hz, 2H), 7.93 (d, J=8 Hz, 2H)

Step D: (4S)-3,3-Diethyl-1-[(R)-α-n-propyl-(4-methyl) benzylaminocarbonyl]-4-[(R,S)-4-((1-hydroxy)-ethyl) phenoxy]azetidin-2-one To a solution of (4S)-3,3-diethyl-1-[(R)-α-n-propyl(4-methyl)benzylaminocarbonyl]-4-[(4-acetyl)phenoxy] azetidin-2-one (1.3 gm, 2.9 mmol) in 100% ethanol (25 mL) was added sodium borohydride (0.13 gm, 3.5 mmol). The reaction was stirred at rt for 3 hrs and then quenched into a mixture of ice water, 2N hydrochloric acid (10 mL) and ether. The layers were separated and the ether layer was washed with water and brine and the aqueous layers were consecutively extracted with a second portion of ether and the pooled ether layers were dried and evaporated. The residue (1.3 gm) was clean by TLC and used without further purification.

NMR (CDCl$_3$; δ from TMS): 0.92, 0.95, 1.09 (3 t, J=8 Hz, 9H), 1.2–1.5 (m, 2H), 1.48 (d, J=8 Hz, 3H), 1.6–2.1 (m, 6H), 2.34 (s, 3H), 4.90 (m, 2H), 5.58 (s, 1H), 6.95 (d, J=8 Hz, 1H), 7.1–7.25 (m, 8H)

Step E: (4S)-3,3-Diethyl-1-[(R)-α-n-propyl-(4-methyl) benzylaminocarbonyl]-4-[(R,S)-4-((1-(2-methoxyethyl) methylamino)ethyl)phenoxy]azetidin-2-one (4S)-3,3-Diethyl-1-[(R)-α-n-propyl-(4-methyl) benzylaminocarbonyl]-4-[(R,S)-4-((1-hydroxy)ethyl) phenoxy]azetidin-2-one (250 mg, 0.55 mmol) was converted to the bromide as in Example 6, Step A and then N-(2-methoxyethyl)methyl amine (300 mg, 3.3 mmol) was added at rt and stirred for 2 hrs. The volatiles were evaporated in vacuo and the residue was taken up in ether and washed with potassium carbonate solution and brine. The aqueous layers were consecutively reextracted with another portion of ether and the pooled ether layers were dried over sodium sulfate and evaporated. The residue was purified by preparative TLC eluting with 57% methanol/30% ethyl acetate/65% hexanes to give 80 mg (28%) of the title compound as an oil, the main component being the higher R$_f$ vinyl biproduct.

NMR (CDCl$_3$; δ from TMS): 0.92, 0.95, 1.09 (3 t, J=8 Hz, 9H), 1.2–1.5 (m, 2H), 1.45 (d, J=8 Hz, 3H), 1.6–2.1 (m, 6H), 2.24 (s, 3H), 2.34 (s, 3H), 2.44 and 2.64 (2 m, 2H), 3.32 (s, 3H), 3.46 (br t, J=8 Hz, 2H), 3.59 (br q, J=8 Hz, 1H), 4.84 (q, J=8 Hz, 1H), 5.58 (s, 1H), 6.95 (d, J=8 Hz, 1H), 7.1–7.3 (m, 8H).

EXAMPLE 13

Starting with (4S)-3,3-diethyl-1-[(R)-α-n-propyl(4-methyl)-benzylaminocarbonyl]-4-[(4-(1-hydroxyethyl) phenoxy]azetidin-2-one prepared in Example 12, Step D and using the procedure of Example 12, Step E, but using the corresponding substituted amine, the compounds in the following table were prepared.

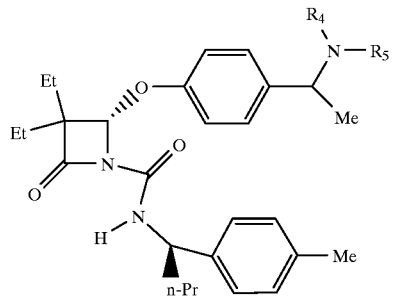

| R$_4$ | R$_5$ |
|---|---|
| Me | CH$_2$CH$_2$OCONMe$_2$ |
| Et | CH$_2$CH$_2$OMe |
| —CH$_2$CH$_2$OCH$_2$CH$_2$— | |
| —CH$_2$CH$_2$CH$_2$CH(S—CH$_2$OMe)— | (isomer A) |
| —CH$_2$CH$_2$CH$_2$CH(S—CH$_2$OMe)— | (isomer B) |
| Me | CH(Me)CH$_2$OMe |
| Me | CH$_2$CH$_2$OCH$_2$CH$_2$OMe |
| —CH$_2$CH$_2$CH(OMe)CH$_2$— | |
| H | Me |
| Me | CH$_2$CH$_2$OH |
| H | CH$_2$CH$_2$OMe |
| H | CH$_2$CH$_2$OH |

EXAMPLE 14

(S)-(−)-N-Carbobenzyloxy-N-methyl-4-hydroxy-α-methylbenzylamine

Step A: (S)-(−)-α-methyl-4-nitrobenzylamine hydrochloride (S)-(−)-α-Methylbenzylamine was nitrated according to the procedure of C. W. Perry, et. al., Synthesis 1977, 492. Thus, fuming nitric acid (750 mL) was cooled in an ice-ethanol bath to −20° C. and (S)-(−)-α-methylbenzylamine (100 gm, 830 mmol) was added over 30 min maintaining the temperature at <10° C. After another 20 min the reaction was poured over ice (2 Kg) and the pH adjusted to 11 with 50% sodium hydroxide. The product was then extracted with benzene and washed with water and brine. The aqueous layers were back-extracted with another portion of benzene and the combined layers were dried over sodium sulfate and evaporated to about 2 L. A solution of 100% ethanol containing 47 gm of anhyd. hydrochloric acid was added and the hydrochloride salt allowed to crystallize overnight to give 78 gm solid. This was recrystallized from benzene/ethanol to afford 42 gm (30%) of the title salt.

Step B: (S)-(−)-N-Carbobenzyloxy-α-methyl-4-nitrobenzylamine

To a solution of (S)-(−)-α-methyl-4-nitrobenzylamine hydrochloride (7.96 gm, 48 mmol) in acetone (20 mL) was added 5N sodium hydroxide (10 mL, 50 imol) and the solution was cooled in an ice bath. Solutions of benzylchloroformate (9.8 mL, 53 mmol) in acetone (10 mL) and 5N sodium hydroxide (11 mL, 55 mmol) were simultaneously added over 0.5 hr and the reaction was then allowed to warm to rt over 16 hrs. The reaction was poured into a mixture of ice water and ether and the layers were separated. The ether layer was washed with water and brine and the aqueous layers were consecutively extracted with a second portion of ether. The pooled ether layers were dried over sodium sulfate and evaporated to give 14.3 gm (quantitative) of clean title compound which was used without purification.

Step C: (S)-(−)-N-Carbobenzyloxy-N-methyl-α-methyl-4-nitrobenzylamine

A solution of (S)-(−)-N-carbobenzyloxy-α-methyl-4-nitrobenzylamine (8.2 gm, 28 mmol) and methyl iodide (2.6 mL, 42 mmol) in DMF (50 mL) was cooled under nitrogen in an ice bath to 5–10° C. and sodium hydride (60% suspension in mineral oil) (1.2 gm, 31 mmol) was added in portions over 15 min while maintaining the temperature at 5–10° C. The reaction was stirred for 1 hr and then slowly quenched into a mixture of ice water, 2N hydrochloric acid (20 mL) and ether and the layers were separated. The ether layer was washed with water and brine and the aqueous layers were consecutively extracted with a second portion of ether. The pooled ether layers were dried over sodium sulfate and evaporated. The residue was purified by flash chromatography using 10–30% ethyl acetate/hexanes to give 6.6 gm (77%) of the title compound. $[\alpha]_D$ (EtOH)=–97°.

NMR (CDCl$_3$; δ from TMS): 1.59 (d, J=8 Hz, 3H), 2.75 (br s, 3H), 5.20 (s, 2H), 5.6 (br m, 1H), 7.36 (br s, 5H), 7.43 (br d, J=9 Hz, 2H), 8.17 (d, J=9 Hz, 2H).

Step D: (S)-(–)-N-Carbobenzyloxy-N-methyl-4-amino-α-methylbenzylamine

α-A solution of (S)-(–)-N-carbobenzyloxy-N-methyl-methyl-4-nitrobenzylamine (6.6 gm, 21 imol) in 100% ethanol (100 mL) was cooled in an ice bath while a solution of stannous chloride dihydrate (14.2 gm, 63 mmol) in conc. hydrochloric acid (25 mL) was added. The reaction was allowed to warm to rt over 14 hrs and was then quenched into a solution of ice, 5N sodium hydroxide (100 mL) and ether and the pH adjusted to 9–10. The layers were separated and the ether layer was washed with brine. The aqueous layers were consecutively extracted with a second portion of ether and the pooled ether layers were dried over sodium sulfate and evaporated. The residue was partially purified by flash chromatography using 20–30% ethyl acetate/hexanes, then 5% methanol/30% ethyl acetate/65% hexanes to give 6.0 gm of impure title compound containing variable amounts of benzyloxycarbonylmethylamine.

Step E: (S)-(–)-N-Carbobenzyloxy-N-methyl-4-hydroxy-α-methylbenzylamine

The above (S)-(–)-N-carbobenzyloxy-N-methyl-4-amino-α-methylbenzylamine (6.0 gm, assume 21 mmol) was dissolved in 2N sulfuric acid (63 mL) and cooled in an ice salt bath. A solution of sodium nitrite (1.6 gm, 23 mmol) in water (25 mL) was added over 15 min at 0–5° C. and the reaction stirred for another 0.5 hr. Toluene (100 mL) was then added and the reaction was rapidly heated to 80–85° C. on a steam bath. The reaction turned very dark and after 10 min was poured onto ice and extracted with 2 portions of ether. The ether layers were each washed with brine, combined, dried over sodium sulfate and evaporated. The residue was purified by flash chromatography using 20–30% ethyl acetate/hexanes to give 3.5 gm (58%) of the title compound.

NMR (CDCl$_3$; δ from TMS): 1.48 (d, J=8 Hz, 3H), 2.64 (br s, 3H), 5.22 (s, 2H), 5.65 (br m, 1H), 6.80 (d, J=8 Hz, 2H), 7.14 (br d, J=8 Hz, 2H), 7.37 (br s, 5H).

EXAMPLE 15

(4R,S)-3,3-Diethyl-4-{4-[(S)-1-(N-carbobenzyloxymethylamino)ethyl]phenoxy}azetidin-2-one Method A:

To a solution of (S)-(–)-N-carbobenzyloxy-N-methyl-4-hydroxy-α-methylbenzylamine (3.5 gm, 12.2 mmol) and 4-acetyloxy-3,3-diethylazetindin-2-one (5.0 gm, 24.4 mmol) in acetone (100 mL) was added a solution of potassium carbonate (1.9 gm, 18.3 mmol) in water (25 mL). The reaction was stirred at rt for 16 hrs and was then poured into water and extracted with two portions of ethyl acetate. The ethyl acetate layers were each washed with water and brine, then combined, dried over sodium sulfate and evaporated. The residue was purified by flash chromatography using 30–40% ethyl acetate/hexanes to give 3.0 gm (60%) of the title compound.

NMR (CDCl$_3$; δ from TMS): 1.04, 1.07 (2 t, J=8 Hz, 6H), 1.51 (d, J=6 Hz, 3H), 1.7–2.0 (m, 4H), 2.64 (s, 3H), 5.22 (s, 2H), 5.37 (s, 1H), 5.55 (v br m, 1H), 6.55 (br s, 1H), 6.84 (d, J=8 Hz, 2H), 7.24 (br d, J=8 Hz, 2H), 7.38 (br s, 5H).

Method B:

To a solution of (S)-(–)-N-carbobenzyloxy-N-methyl-4-hydroxy-α-methylbenzylamine (33 gm, 115 mmol) and 4-acetoxy-3,3-diethylazetindin-2-one (44 gm, 230 mmol) in toluene (1 L) was added barium hydroxide octahydrate (39 gm, 180 mmol). The reaction was heated to 40–45° C. for 3 hrs and then poured into ice water containing 2N hydrochloric acid (200 mL) and extracted twice with ether. The ether layers were each washed with sodium bicarbonate solution and brine, combined, dried over sodium sulfate and evaporated. The residue was purified by preparative chromatography using 35–5070 ethyl acetate/hexanes to give 38 gm (80%) of the title compound.

EXAMPLE 16

(4S)-3,3-Diethyl-4-{(S)-4-[1-((2-methoxyethyl) methylamino)ethyl]phenoxy}-1-[(R)-α-n-propyl-(4-methyl)benzylaminocarbonyl]azetidin-2-one Step A: (4S)-3,3-Diethyl-4-{(S)-4-[1-(N-carbobenzy-loxymethylamino) ethyl]phenoxy}-1-[(R)-α-allyl-(4-methyl)benzylaminocarbonyl]azetidin-2-one A solution of (4R,S)-3,3-diethyl-4-{(S)-4-[1-(N-carbobenzyloxy-methylamino)ethyl]phenoxy}-azeti-din-2-one (38 gm, 93 mmol) and (R)-α-allyl-(4-methyl)-benzyl isocyanate (21 gm, 112 mmol) in DMF (600 mL) was stirred under nitrogen for 4 hrs and then poured into ice water and extracted twice with ether. The ether layers were each washed with water and brine, combined, dried over sodium sulfate and evaporated. The residue was purified by preparative chromatography using 5% methylene chloride/10% ethyl acetate/85% hexanes to give 19 gm (35%) of the title compound as the higher R$_f$ isomer.

NMR (CDCl$_3$; δ from TMS): 0.96, 1.07 (2 t, J=8 Hz, 6H), 1.51 (d, J=6 Hz, 3H), 1.7–2.1 (m, 4H), 2.34 (s, 3H), 2.56 (t, J=7 Hz, 2H), 2.62 (s, 3H), 4.95 (q, J=8 Hz, 1H), 5.1–5.2 (m, 2H), 5.20 (s, 2H), 5.58 (s, 1H), 5.55 (v br m, 1H), 5.6–5.8 (m, 1H), 7.01 (br d, J=8 Hz, 1H), 7.1–7.3 (m, 8H), 7.38 (br s, 5H).

Step B: (4S)-3,3-Diethyl-4-{(S)-4-[1-methylaminoethyl]phenoxy}-1-[(R)-α-n-propyl-(4-methyl)benzylaminocarbonyl]azetidin-2-one A solution of (4S)-3,3-diethyl-4-{(S)-4-[1-(N-carbobenzyloxy-methylamino)ethyl]phenoxy}-1-[(R)-1-α-allyl-(4-methyl)benzylaminocarbonyl]azetidin-2-one (32 gm, 54 mmol) in 100% ethanol (250 mL) was hydrogenated with 1.0 gm of 10% palladium/carbon at 40 p.s.i. for 2 hrs and then filtered and evaporated to give 16 gm (100%) of crude title compound which was used directly in the following step.

NMR (CDCl$_3$; δ from TMS): 0.90, 0.95, 1.06 (3 t, J=8 Hz, 9H), 1.2–1.5 (m, 2H), 1.35 (d, J=7 Hz, 3H), 1.7–2.1 (m, 6H), 2.34 (s, 3H), 2.42 (s, 3H), 4.13 (br q, J=7 Hz, 1H), 4.82 (q, J=8 Hz, 1H), 5.58 (s, 1H), 6.91 (br d, J=8 Hz, 1H), 7.16 (s, 4H), 7.24 (d, J=9 Hz, 2H), 7.52 (d, J=9 Hz, 2H).

Step C: (4S)-3,3-Diethyl-4-{(S)-4-[1-(N-methoxyacetyl-methylamino)ethyl]phenoxy}-1-[(R)-α-n-propyl(4-methyl) benzylaminocarbonyl]azetidin-2-one The residue from Step B was taken up in methylene chloride (150 mL) and cooled in an ice bath and diisopropylethylamine (7.0 mL, 40 mmol) was added. A solution of methoxyacetyl chloride (3.5 gm, 32 mmol) in methylene chloride (20 mL) was added over 10 min. The reaction was stirred another 15 min before it was quenched into a mixture of ice water, 2N hydrochloric acid (40 mL) and methylene chloride. The layers were separated and the aqueous layer was extracted with another portion of methylene chloride. The methylene chloride layers were each washed with brine, combined, dried over sodium sulfate and evaporated. The residue was purified by preparative chromatography with 5% methanol/25% ethyl acetate/70% hexanes to give 28 gm (97%) of the title compound.

NMR (CDCl$_3$; δ from TMS): 0.92, 0.96, 1.08 (3 t, J=8 Hz, 9H), 1.2–1.5 (m, 2H), 1.48 and 1.58 (2 d, J=8 Hz, 3H), 1.7–2.1 (m, 6H), 2.34 (s, 3H), 2.62 and 2.64 (2 s, 3H), 3.48 (s, 3H), 4.14 and 4.25 (2 s, 2H), 4.84 (q, J=8 Hz, 1H), 5.15 and 6.03 (m and br q, J=8 Hz, 1H), 5.58 (s, 1H), 6.96 (br d, J=8 Hz, 1H), 7.16 (br s, 4H), 7.21 (br s, 4H).

Step D: (4S)-3,3-diethyl-4-{(S)-4-[1-((2-methoxyethyl) methylamino)ethyl]phenoxy}-1-[(R)-α-n-propyl-(4-methyl)benzylaminocarbonyl]azeti-din-2-one To a solution of (4S)-3,3-diethyl-4-{(S)-4-[1-(N-methoxyacetyl-methylamino)ethyl]phenoxy}-1-[(R)-α-n-propyl-(4-methyl)benzylaminocarbonyl]azetidin-2-one (13 gm, 24 mmol) in THF (150 mL) was added a 2M solution of borane-methyl sulfide in THF (36 mL, 72 nmmol) and the reaction stirred at rt for 7 hrs. The reaction was then quenched with methanol (20 mL) and then dimethylamino-ethanol (17 mL) added to decompose the borate complex. After stirring at rt for 16 hrs most of the THF was evaporated in vacuo and the residue was taken up in ether, washed twice with potassium carbonate solution and brine. The aqueous layers were reextracted with another portion of ether and the pooled ether layers were then dried over sodium sulfate and evaporated. The residue was purified by preparative chromatography using 1.5–4% methanol/methylene chloride to afford 11 gm (86%) of the title compound as a viscous oil.

NMR (CDCl$_3$; δ from TMS): 0.92, 0.95, 1.08 (3 t, J=8 Hz, 9H), 1.2–1.5 (m, 2H), 1.34 (d, J=7 Hz, 3H), 1.6–2.0 (m, 6H), 2.23 (s, 3H), 2.34 (s, 3H), 2.42 and 2.60 (2 m, 2H), 3.32 (s, 3H), 3.44 and 3.45 (2 t, J=7 Hz, 2H), 3.58 (q, J=7 Hz, 1H), 4.85 (q, J=8 Hz, 1H), 5.58 (s, 1H), 6.97 (d, J=8 Hz, 1H), 7.1–7.3 (m, 8H).

EXAMPLE 17

(4S)-3,3-diethyl-4-{(R)-4-[1-((2-methoxyethyl) methylamino)ethyl]phenoxy}-1-[(R)-α-n-propyl-(4-methyl)benzylaminocarbonyl]azetidin-2-one Starting with (R)-(+)-α-methylbenzylamine and proceeding essentially the same as in Example 13–17 gave the title compound.

NMR (CDCl$_3$; δ from TMS): 0.91, 0.94, 1.08 (3 t, J=8 Hz, 9H), 1.2–1.5 (m, 2H), 1.34 (d, J=7 Hz, 3H), 1.6–2.0 (m, 6H), 2.24 (s, 3H), 2.35 (s, 3H), 2.42 and 2.60 (2 m, 2H), 3.32 (s, 3H), 3.44 (br t, J=7 Hz, 2H), 3.58 (br q, J=7 Hz, 1H), 4.84 (q, J=8 Hz, 1H), 5.58 (s, 1H), 6.95 (d, J=8 Hz, 1H), 7.1–7.3 (m, 8H).

EXAMPLE 18

(4S)-3,3-Diethyl-1-[(R)-α-n-propyl-(4-methyl) benzylaminocarbonyl]-4-[(4-((2-dimethylaminocarbonyloxy)ethyl) methylaminomethyl)phenoxy]azetidin-2-one Method A:

A solution of (4S)-3,3-diethyl-1-[(R)-α-n-propyl-(4-methyl)benzylaminocarbonyl]-4-[(4-bromomethyl) phenoxy]azetidin-2-one (2.3 mmol) in THF (50 mL) was prepared as in Example 6, Step A. To this solution was added (N-(2-dimethylaminocarbonyloxy)ethyl) methylamine (670 mg, 4.6 mmol) and triethylamine (0.325 mL, 2.3 mmol) and the reaction was stirred for 3 hrs at rt. The volatiles were evaporated in vacuo and the residue taken up in ether and washed with potassium carbonate solution and brine. The aqueous layers were consecutively extracted with another portion of ether and the pooled ether layers were dried over sodium sulfate and evaporated. The residue was purified by preparative TLC eluting with 50% ethyl acetate/hexanes to give 750 mg (58%) of the title compound as an oil.

NMR (CDCl$_3$; δ from TMS): 0.90, 0.94, 1.07 (3 t, J=8 Hz, 9H), 1.2–1.5 (m, 2H), 1.6–2.0 (m, 6H), 2.33 (s, 3H), 2.34 (s, 3H), 2.73 (br t, J=6 Hz, 2H), 2.92 (br s, 6H), 3.60 (br s, 2H), 4.27 (t, J=6 Hz, 2H), 4.85 (q, J=8 Hz, 1H), 5.58 (s, 1H), 6.97 (d, J=8 Hz, 1H), 7.1–7.3 (m, 8H).

Method B:

Step A: Preparation of (4S)-3,3-diethyl-1-[(R)-α-n-propyl-(4-methyl)benzylaminocarbonyl]-4-[(4-2-hydroxyethyl)) methylaminomethyl)phenoxy]-azetidin-2-one To a solution of (4S)-3,3-diethyl-1-[(R)-α-n-propyl(4-methyl)benzylaminocarbonyl]-4-[(4-bromomethyl) phenoxy]azetidin-2-one, prepared as in Example 6, Step A, (4.5 mmol) was added (2-hydroxyethyl)methylamine (0.10 gm,1.36 mmol). After 1 hr the reaction was complete and the product (170 mg, 75%) was isolated as in Example 6, Step B using 25% ethyl acetate/75% hexanes for the purification.

NMR (CDCl$_3$; δ from TMS): 0.92, 0.96, 1.08 (3 t, J=8 Hz, 9H), 1.2–1.5 (m, 2H), 1.6–2.0 (m, 6H), 2.24 (s, 3H), 2.34 (s, 3H), 2.60 (t, J=6 Hz, 2H), 3.0 (br s, 1H), 3.56 (s, 3H), 3.64 (t, J=6 Hz, 2H), 4.85 (q, J=8 Hz, 1H), 5.60 (s, 1H), 6.97 (d, J=8 Hz, 1H), 7.1–7.3 (m, 8H).

Step B: Preparation of (4S)-3,3-Diethyl-1-[(R)-α-n-propyl-(4-methyl)benzylaminocarbonyl]-4-[(4-2-(dimethylaminocarbonyloxy)ethyl) methylaminomethyl)-phenoxy]azetidin-2-one To a solution of material prepared in Step A (100 mg, 0.20 mmol) and TEA (0.15 mL) in methylene chloride (1 mL) was added N,N-dimethylcarbamyl chloride (0.20 mL) and a trace of DMAP. The reaction was heated in a sealed vial at 45° C. for 14 days. The reaction was concentrated and purified by flash chromatography (50% ethyl acetate/50% hexanes) to give 25 mg (20%) of the title compound identical with that prepared in Example 18, Method A.

EXAMPLE 19

(4S)-3,3-Diethyl-1-[(R)-α-n-propyl-(4-methyl) benzylaminocarbonyl]-4-[(4-(2-methoxyethyl) methylaminomethyl)phenoxyl]azetidin-2-one Step A: (4S)-3,3-Diethyl-1-[(R)-α-n-propyl-(4-methyl) benzylaminocarbonyl]-4-[(4-methyl-aminomethyl)-phenoxy]azetidin-2-one (4S)-3,3-Diethyl-1-[(R)-α-n-propyl-(4-methyl) benzylaminocarbonyl]-4-[(4-hydroxymethyl) phenoxy] azetidin-2-one (1.0 gm, 23 mmol) was converted to a solution of the bromide as in Example 6, Step A and was then added over 10 min to a solution of 40% aqueous methylamine (0.90 mL, 11.5 mmol) in acetonitrile (20 mL). The reaction was stirred at rt for 3 hrs and then diluted with ether and washed with potassium carbonate solution and brine. The aqueous layers were consecutively extracted with another portion of ether and the pooled ether layers were dried over sodium sulfate and evaporated. The residue was purified by flash chromatography eluting with ethyl acetate then 30% methanol/ethyl acetate to give 400 mg (39%) of the title compound as an oil.

NMR (CDCl$_3$; δ from TMS): 0.91, 0.94, 1.08 (3 t, J=8 Hz, 9H), 1.2–1.5 (m, 2H), 1.6–2.0 (m, 6H), 2.34 (br s, 6H), 3.45 (br s, 2H), 3.70 (br s, 1H), 4.85 (q, J=8 Hz, 1H), 5.58 (s, 1H), 6.97 (d, J=8 Hz, 1H), 7.1–7.3 (m, 8H).

Step B: (4S)-3,3-Diethyl-1-[(R)-α-n-propyl-(4-methyl) benzylaminocarbonyl]-4-[(4-(2-methoxyethyl) methylaminomethyl)phenoxy]azetidin-2-one A solution of (4S)-3,3-diethyl-1-[(R)-α-n-propyl (4-methyl)benzylaminocarbonyl]-4-[(4-(methyl-aminomethyl) phenoxy]azetidin-2-one (200 mg, 0.44 mmol), triethylamine (0.080 mL, 0.58 mmol) and (2-methoxy)ethyl bromide (80 mg, 0.58 mmol) in acetonitrile (1 mL) was stirred at rt for 16 hrs, then at 50° C. for 24 hrs. The reaction was then diluted with ethyl acetate and washed with sodium carbonate solution, water and brine. The aqueous layers were back-extracted with more ethyl acetate and the pooled layers dried over sodium sulfate and evaporated. The residue was purified by flash chromatography using 60% ethyl acetate/hexanes to give 50 mg (22%) of the title as an oil.

NMR (CDCl$_3$; δ from TMS): 0.91, 0.94, 1.04, 1.08 (4 t, J=8 Hz, 12H), 1.2–1.5 (m, 2H), 1.6–2.1 (m, 6H), 2.26 (s, 3H), 2.34 (s, 3H), 2.58 (t, J=6 Hz, 2H), 3.35 (s, 3H), 3.50 (s, 2H), 3.4–3.6 (m, 2H), 4.85 (q, J=8 Hz, 1H), 5.57 (s, 1H), 6.96 (d, J=8 Hz, 1H), 7.1–7.3 (m, 8H).

EXAMPLE 20

(4S)-3,3-Diethyl-1-[(R)-α-n-propyl-(4-methyl) benzylaminocarbonyl]-4-[(4-(2-ethoxyethyl) methylaminomethyl)phenoxy]azetidin-2-one Using the procedure as described in Example 19, Step B, but using (2-ethoxy)ethyl bromide, (4S)-3,3-diethyl-1-[(R)-α-n-propyl-(4-methyl)benzyl-aminocarbonyl]-4-[(4-(2-ethoxyethyl)methylamino-methyl) phenoxy]azetidin-2-one was prepared.

NMR (CDCl$_3$; δ from TMS): 0.91, 0.94, 1.04, 1.08 (4 t, J=8 Hz, 12H), 1.2–1.5 (m, 2H), 1.6–2.1 (m, 6H), 2.25 (s, 3H), 2.34 (s, 3H), 2.60 (t, J=6 Hz, 2H), 3.4–3.6 (m,6H), 4.85 (q, J=8 Hz, 1H), 5.58 (s, 1H), 6.95 (d, J=8 Hz, 1H), 7.1–7.25 (m, 8H).

EXAMPLE 21

3,3-Diethyl-1-[(R)-α-(n-propyl)-4-(methyl) benzylaminocarbonyl]-4-(S)-[4-{1-(RS)-(N-(n-propyl)-N-(methyl)amino)-2-methoxyethyl}phenoxy]azetidin-2-one Step A: 3,3-Diethyl-4-(RS)-[4-(1-(oxo)-2-(methoxy)ethyl) phenoxy]azetidin-2-one To a solution of 2.00 gm (12 mmol) of 4-hydroxy-α-methoxyacetophenone (prepared according to Shetty, H. U.; Nelson, W. L. *J. Med. Chem.* 1988, 31, 55–58) and 3.34 gm (18 mmol) of 3,3-diethyl-4-acetoxyazetidin-2-one (see EPO 337 549) in 34 mL of acetone was added a solution of 2.50 gm (18 mmol) of potassium carbonate in 10 mL of water. After one hr, 50 mL of water was added and the mixture extracted with 4×60 mL of ether. The organic extracts were dried over sodium sulfate, filtered and concentrated in vacuo. The residue was purified by flash chromatography on 166 gm of silica eluting with 2.5 L of 60:40 hexanes: ethyl acetate then 2.5 L of 50:50 hexanes: ethyl acetate to provide 2.49 gm (71%) of an oil which was homogeneous by TLC (60:40 hexanes: ethyl acetate) and mixed fractions weighing 1.24 gm.

NMR (CDCl$_3$; δ from TMS): 1.14 (t, 6H), 1.8–2.2 (m, 4H), 3.58 (s, 3H), 4.75 (s, 2H), 5.55 (s, 1H), 6.60 (br s, 1H), 7.00 (app d, 2H), 8.04 (app d, 2H).

Step B: 3,3-Diethyl-1-[(R)-α-(allyl)-4-(methyl) benzylaminocarbonyl]-4-(S)-[4-(1-oxo-2-methoxyethyl) phenoxy]azetidin-2-one To a solution of 1.64 gm (5.6 mmol) of 3,3-diethyl-4-(RS)-[4-(1-oxo-2-methoxyethyl) phenoxy]azetidin-2-one in 23 mL of dry DMF was added 78 mg (0.56 mmol) of powdered potassium carbonate and then 1.27 gm (6.8 mmol) of (R)-α-allyl-4-methyl-benzyl isocyanate, and the mixture was stirred for one hour. The solution was treated with 50 mL of water and was extracted with 100 mL of 50:50 hexanes: ethyl acetate, 80 mL of ethyl acetate and then 100 mL of hexanes: ethyl acetate. Each extract was washed with 10 mL of water and 10 mL of brine. The combined extracts were dried over sodium sulfate, filtered and concentrated in vacuo. The residue was purified by flash chromatography on 240 gm of silica with 4 L of 70:30 hexanes: ethyl acetate to give a small amount of higher R$_f$ material (3,3-diethyl-1-[(R)-α-(allyl)-4-(methyl)benzylaminocarbonyl]-4-(S)-[4-(1-(oxo)-2-(methoxy) ethyl)phenoxy]azetidin-2-one) and a substantial amount of mixed fractions. The mixed fractions were purified by flash chromatography on 173 gm of silica eluting with 4 L of 75:25 hexanes:ethyl acetate, and the mixed cuts from that chromatography were fractionated again under the same conditions. The pooled fractions containing mostly desired product were subjected to a final purification by flash chromatography on 143 gm of silica eluting with 3 L of 98:2 methylene chloride: ethyl acetate to give 1.40 gm of product as an oil.

NMR (CDCl$_3$; δ from TMS): 1.05 (t, 3H), 1.15 (t, 3H), 1.8–2.2 (m, 4H), 2.40 (s, 3H), 2.62 (t, 2H), 3.55 (s, 3H), 4.70 (s, 2H), 4.99 (q, 1H), 5.1–5.3 (m, 2H), 5.65–5.9 (m, 1H), 5.77 (s, 1H), 7.05 (d, 1H), 7.35 (app d, 2H), 7.98 (app d, 2H).

Step C: 3,3-Diethyl-1-[(R)-α-(n-propyl)-4-(methyl) benzylaminocarbonyl]-4-(S)-[4-(1-(RS)-(hydroxy)-2-methoxyethyl)phenoxy]azetidin-2-one To a solution of 0.45 gm (0.94 mmol) of 3,3-diethyll-[(R)-α-(allyl)-4-(methyl) benzylaminocarbonyl]-4-(S)-[4-(1-(oxo)-2-(methoxy)ethyl) phenoxy]-azetidin-2-one in 9 mL of methanol and 1 mL of water was added 100 mg of 5% Ru/C, and the resulting slurry was agitated on a Parr shaker under 40 p.s.i. of hydrogen for 24 hr, at which point an additional 70 mg of 5% Ru/C was added and the reaction continued for an additional 4 days. The mixture was then filtered through Celite and concentrated in vacuo, and the residue was azeotroped with toluene several times to remove residual water. The residue was purified by flash chromatography on 47 gm of silica with 70:30 hexanes: ethyl acetate to give 0.29 gm of an oil.

NMR (CDCl$_3$; δ from TMS): 1.00 (app q, 6H), 1.15 (t, 3H), 1.25–1.60 (m, 3H), 1.70–2.10 (m, 5H), 2.40 (s, 3H), 2.83 (br s, 1H), 3.40–3.65 (m, 2H), 3.50 (s, 3H), 4.80–5.00 (m, 2H), 5.67 (s, 1H), 7.03 (d, 1H), 7.15–7.50 (m, 8H).

Step D: 3,3-Diethyl-1-[(R)-α-(n-propyl)-4-(methyl) benzylaminocarbonyl]-4-(S)-[4-{1-(RS)-(N-(n-propyl)-N-(methyl)amino)-2-methoxyethyl}phenoxy]azetidin-2-one A solution of 88 mg (0.18 mmol) of 3,3-diethyl-1-[(R)-α-(n-propyl)-4-(methyl) benzylaminocarbonyl]-4-(S)-[4-(1-(RS)-(hydroxy)-2-methoxyethyl)ph enoxy]azetidin-2-one in 1 mL of acetonitrile was treated with 108 mg (0.26 mmol) of triphenylphosphine dibromide under an atmosphere of nitrogen. After stirring 4 hr, ca. 0.3 mL of n-propylmethylamine was added and the mixture stirred at room temperature for 24 hr. The mixture was then concentrated and the residue partitioned between 3 mL of saturated aqueous sodium bicarbonate and 5 mL of ethyl acetate and the aqueous phase was extracted with 2×10 mL of ethyl acetate. The combined organic layers were dried over sodium sulfate, filtered and concentrated in vacuo. The residue was purified by flash chromatography on 29 gm of silica gel eluting with 500 mL of 98:2 methylene chloride: methanol then 500 mL of 97:3 methylene chloride: methanol to give 64 mg (65%) of an oil.

NMR (CDCl$_3$; δ from TMS): 0.8–1.1(overlapping t, 9H), 1.15(t, J=7, 3H), 1.2–1.7(m, 4H), 1.7–2.2(m, 6H), 2.27(s, 3H), 2.4(s, 3H), 2.2–2.5(m, 2H), 3.4(s, 3H), 3.6–3.9(m, 3H), 4.9(q, J=8, 1H), 5.65(s, 1H), 7.03(d, J=8, 1H), 7.15–7.40(m, 8H).

Mass Spectrum (FAB): m/Z 538(M+1, 100), 492(8), 315(12), 276(18), 147(21), 126(24), 105(38).

EXAMPLE 22

3,3-Diethyl-1-[(R)-α-(n-propyl)-4-(methyl) benzylaminocarbonyl]-4-(S)-[4-{1-(RS)-(N,N-dimethylamino)-2-methoxyethyl}phenoxy]azetidin-2-one Step A: 3,3-Diethyl-1-[(R)-α-(allyl)-4-(methyl) benzylaminocarbonyl]-4-(S)-[4-(1-(RS)-amino-2-methoxy-ethyl)phenoxy]azetidin-2-one A suspension of 755 mg (14.1mmol) of ammonium chloride and 213 mg (3.8 mmol) of potassium hydroxide in 5 mL of dry methanol was treated with 520 mg (1.08 mmol) of 3,3-diethyl-1-[(R)-α-(allyl)-4-(methyl) benzylaminocarbonyl]-4-(S)-[4-(1-oxo-2-methoxyethyl) phenoxy]azetidin-2-one. After 30 min, 205 mg (3.26 mmol) of sodium cyanoborohydride was added and the mixture stirred for 14 hr, at which point 1 gm of 3A molecular sieves was added. After 3 days, the mixture was diluted with methanol, filtered through Celite, concentrated in vacuo, filtered again (rinsing with ethyl acetate), concentrated in vacuo, and the residue purified by flash chromatography on 50 gm of silica eluting with 800 mL of 67:33 hexanes: ethyl acetate, then sequentially 1 L of 99:1 methylene chloride: methanol, 500 mL of 98.5: 1.5 methylene chloride: methanol, and 1 L of 97:3 methylene chloride: methanol to give 170 mg of 3,3-Diethyl-1-[(R)-α-(allyl)-4-(methyl) benzylaminocarbonyl]-4-(S)-[4-(1-(RS)-hydroxy-2-methoxyethyl)phenoxy]azetidin-2-one as well as impure product. The latter was purified by flash chromatography on 43 g of silica eluting with 97.5:2.5:0.3 methylene chloride: methanol: ammonia water to provide the product as an oil.

NMR (CDCl$_3$; δ from TMS): 1.03 (t, 3H), 1.13 (t, 3H), 1.60–2.15 (m, 6H), 2.39 (s, 3H), 2.62 (t, 2H), 3.30–3.60 (m, 2H), 3.44 (s, 3H), 4.23 (m, 1H), 5.03 (q, 1H), 5.10–5.30 (m, 2H), 5.65 (s, 1H), 5.65–5.90 (m, 1H), 7.08 (d, 1H), 7.20—7.40 (m, 8H).

Step B: 3,3-Diethyl-1-[(R)-α-(allyl)-4-(methyl) benzylaminocarbonyl]-4-(S)-[4-(1-(RS)-(dimethylamino)-2-methoxyethyl)phenoxy]-azetidin-2-one A solution of 94 mg (0.20 mmol) of 3,3-diethyl-1-[(R)-α-(allyl)-4-(methyl) benzylaminocarbonyl]-4-(S)-[4-(1-(RS)-amino-2-methoxyethyl) phenoxy]azetidin-2-one in 1 mL of acetonitrile was treated sequentially with 0.15 mL (1.96 mmol) of aqueous formaldehyde and 37 mg (0.59 mmol) of sodium cyanoborohydride. After 15 min, a dilute solution of acetic acid in acetonitrile was added until the pH of the mixture (determined by spotting onto wet pH paper) was ca. 7, and the reaction mixture was stirred for 24 hr. The mixture was then concentrated, partitioned between saturated aqueous sodium bicarbonate and ethyl acetate. The aqueous phase was extracted with 3×10 mL of ethyl acetate, the combined organic layers were dried over sodium sulfate, filtered, and concentrated in vacuo. The residue was purified by flash chromatography on 16 gm of silica eluting with 250 mL of 98:2 methylene chloride: methanol then 600 mL of 97:3 methylene chloride: methanol. The material so obtained was subjected to a final purification by flash chromatography on 15 gm of silica gel eluting with 97.5:2.5:0.2 methylene chloride: methanol: ammonia water to give 56 mg (56%) of an oil.

NMR (CDCl$_3$; δ from TMS): 1.03 (t, 3H), 1.15 (t, 3H), 1.80–2.20 (4H), 2.27 (s, 6H), 2.40 (s, 3H), 2.65 (t, 2H), 3.40 (s, 3H), 3.5 (br m, 1H), 3.60–3.90 (m, 2H), 5.03 (q, 1H), 5.10–5.35 (m, 2H), 5.68 (s, 1H), 5.65–5.90 (m, 2H), 7.10 (d, 1H), 7.10–7.40 (m, 8H).

Step C: 3,3-Diethyl-1-[(R)-α-(n-propyl)-4-(methyl) benzylaminocarbonyl]-4-(S)-[4-{1-(RS)-(N,N-dimethylamino)-2-methoxyethyl}phenoxy]azetidin-2-one A solution of 49 mg (0.096 mmol) of 3,3-diethyl-1-[(R)-α-(allyl)-4-(methyl)benzylamino carbonyl]-4-(S)-[4-(1-(RS)-(dimethylamino)-2-methoxyethyl)phenoxy] azetidin-2-one in 1 mL of ethanol was treated with one drop of acetic acid and then 14 mg of 5% Pd/C. The mixture was stirred under 1 atmosphere of hydrogen for 3.5 hr, and was then filtered through a pad of solid potassium carbonate over Celite. The filtrate was concentrated in vacuo and the residue purified by flash chromatography on 9 gm of silica eluting with 97.5:2.5:0.1 methylene chloride: methanol: ammonia water to give 46 mg (94%) of an oil.

NMR (CDCl$_3$; δ from TMS): 0.9–1.05 (overlapping t, J=7, 6H), 1.1 (t, J=7, 3H), 1.2–1.5 (m, 2H), 1.7–2.2 (m, 6H), 2.25 (s, 6H), 2.36 (s, 3H), 3.36 (s, 3H), 3.45 (m, 1H), 3.5–3.8 (m, 2H), 4.9 (q, J=8, 1H), 5.62 (s, 1H), 7.00 (d, J=8, 1H), 7.1–7.3 (m, 8H).

Mass Spectrum (FAB): m/Z 510(M+1, 100), 315(10), 276(14).

EXAMPLE 23

3,3-Diethyl-1-[(R)-α-(n-propyl)-4-(methyl) benzylaminocarbonyl]-4-(S)-[4-{1-(RS)-(N,N-diethylamino)-2-methoxyethyl}phenoxy]azetidin-2-one Step A: 3,3-Diethyl-1-[(R)-α-(allyl)-4-(methyl) benzylaminocarbonyl]-4-(S)-[4-{1-(RS)-(N,N-diethylamino)-2-methoxyethyl}phenoxy]azeti-din-2-one According to the procedure given in Example 21, Step D, 86 mg (0.18 mmol) of 3,3-diethyl-1-[(R)-α-(allyl)-4-(methyl)benzylaminocarbonyl]-4-(S)-[4-(1-(RS)-(hydroxy)-2-methoxyethyl) phenoxy]azetidin-2-one, 98 mg (0.23 mmol) of triphenylphosphine dibromide and ca. 0.3 mL of diethylamine gave after purification on 15 gm of silica eluting with 500 mL of 98:2 methylene chloride: methanol then 200 mL of 97.5:2.5 methylene chloride: methanol 44 mg (46%) of an oil.

NMR (CDCl$_3$; δ from TMS): 1.0–1.2 (m, 12H), 1.8–2.2 (m, 4H), 2.40 (s, 3H), 2.4–2.8 (m, 61), 3.38 (s, 3H), 3.65–4.00 (m, 3H), 5.05 (q, 1H), 5.1–5.3 (m, 2H), 5.67 (s, 1H), 5.65–5.9 (m, 1H), 7.10 (d, 1H), 7.2–7.4 (m, 8H).

Step B: 3,3-Diethyl-1-[(R)-α-(n-propyl)-4-(methyl) benzylaminocarbonyl]-4-(S)-[4-{1-(RS)-(N,N-diethylamino)-2-methoxyethyl}phenoxy]azeti-din-2-one According to the procedure given in Example 22, step C, 110 mg (0.11 mmol) of 3,3-diethyl-1-[(R)-α-(allyl)-4-(methyl)benzylaminocarbonyl]-4-(S)-[4-{1-(RS)-(N,N-diethylamino)-2-methoxy-ethyl}phenoxy]azetidin-2-one gave after purification by flash chromatography on 8 gm silica eluting with 97.5:2.5:0.1 methylene chloride: methanol: ammonia water 51 mg (88%) of an oil.

NMR (CDCl$_3$; δ from TMS): 0.95–1.25 (m, 15H), 1.3–1.6 (M, 2H), 1.8–2.2 (m, 6H), 2.4 (s, 3H), 10 2.45–2.8 (m, 4H), 3.4 (s, 3H), 3.65–3.9 (m, 2H), 3.95 (m, 1H), 4.9(q, J=8, 1H), 5.65 (s, 1H), 7.05 (d, J=8, 1H), 7.2–7.4 (m, 8H).

Mass Spectrum (FAB): m/Z 538(M+1, 100), 315(16), 276(24), 247(17).

EXAMPLE 24

3,3-Diethyl-1-[(R)-α-(n-propyl)-4-(methyl) benzylaminocarbonyl]-4-(S)-[4-{1-(RS)-(1-pyrrolidino)-2-methoxyethyl}phenoxy]azetidin-2-one According to the procedure given in Example 21, Step D, 111 mg (0.23 mmol) of 3,3-diethyl-1-[(R)-α-(n-propyl)-4-(methyl)benzylaminocarbonyl]-4-(S)-[4-(1-(RS)-(hydroxy)-2-methoxyethyl)phenoxy]azetid in-2-one, 135 mg (0.32 mmol) of triphenylphosphine dibromide and ca. 0.4 mL of pyrrolidine gave after purification by flash chromatography on 15 gm of silica eluting with 98:2:0.2 methylene chloride: methanol: ammonia water followed by a second column employing the same conditions 67 mg (55%) of an oil.

NMR (CDCl₃; δ from TMS): 0.9–1.05 (m, 6H), 1.10 (t, J=7, 3H), 1.2–1.6 (m, 2H), 1.6–2.2 (m, 10H), 2.38 (s, 3H), 2.4–2.7 (m, 4H), 3.3–3.4 (m, 4H), 3.6–3.8 (m, 2H), 4.9 (q, J=8, 1H), 5.63 (s, 1H), 7.00 (d, J=8, 1H), 7.1–7.4 (m, 8H).

Mass Spectrum (FAB): m/Z 536(M+1, 100), 490(6), 276(6), 176(8), 147(12), 105(24).

EXAMPLE 25

3,3-Diethyl-1-[(R)-α-(n-propyl)-4-(methyl) benzylaminocarbonyl]-4-(S)-[4-{1-(RS)-(di-n-propyl)-2-methoxyethyl}phenoxy]azetidin-2-one According to the procedure given in Example 21, Step D, 94 mg (0.19 mmol) of 3,3-diethyl-1-[(R)-α-(n-propyl)-4-(methyl)benzylaminocarbonyl]-4-(S)-[4-(1-(RS)-(hydroxy)-2-methoxyethyl)phenoxy]azetidin-2-one, 118 mg (0.28 mmol) of triphenylphosphine dibromide and ca. 0.4 mL of di-n-propylamine gave, after purification by flash chromatography on 14 gm silica eluting with 350 mL of 80:20 hexanes: ethyl acetate then 250 mL of 50:50 hexanes: ethyl acetate followed by purification on 13 gm of silica eluting with 84:16 hexanes: ethyl acetate 40 mg (36%) of an oil.

NMR (CDCl₃; δ from TMS): d 0.8–1.2 (m, 15H), 1.2–1.6 (m, 6H), 1.7–2.2 (m, 6H), 2.2–2.6 (m, 4H), 2.38 (s, 3H), 3.39 (s, 3H), 3.65–4.00 (m, 3H), 4.9 (q, J=8, 1H), 5.65 (s, 1H), 7.00 (d, J=8, 1H), 7.1–7.4 (m, 8H).

Mass Spectrum (FAB): m/Z 566(M+1, 100), 315(8), 276(15), 151(16), 147(18).

EXAMPLE 26

3,3-Diethyl-1-[(R)-α-(n-propyl)-4-(methyl) benzylaminocarbonyl]-4-(S)-[4-{1-(RS)-(N-ethyl-N-(methyl)amino)2-methoxyethyl}-phenoxy]azetidin-2-one According to the procedure given in Example 21, Step D, 106 mg (0.22 mmol) of 3,3-diethyl-1-[(R)-α-(n-propyl)-4-(methyl)benzylaminocarbonyl]-4-(S)-[4-(1-(RS)-(hydroxy)-2-methoxyethyl)phenoxy]azetid in-2-one, 130 mg (0.31 mmol) of triphenylphosphine dibromide and ca. 0.4 mL of N-methylethylamine gave, after purification by flash chromatography on 30 gm of silica eluting with 850 mL of 98:2 methylene chloride: methanol, then 400 mL of 97.5:2.5 methylene chloride: methanol, 70 mg (61%) of an oil.

NMR (CDCl₃; δ from TMS): d 0.9–1.2 (m, 121), 1.2–1.6 (m, 2H), 1.7–2.2 (m, 6H), 2.3 (s, 3H), 2.45 (s, 3H), 2.4–2.7 (m, 2H), 3.36 (s, 3H), 3.6–3.9 (m, 3H), 4.9 (q, J=8, 1H), 5.63 (s, 1H), 7.00 (d, J=8, 1H), 7.1–7.3 (m, 8H).

Mass Spectrum (FAB): m/Z 524(M+1, 100), 478(40), 276(38), 164(60), 147(42), 126(37), 105(81).

EXAMPLE 27

3,3-Diethyl-1-[(R)-α-(n-propyl)-(3,4-dioxomethylene)benzylaminocarbonyl]-4-(S)-[4-{1-(RS)-(N,N-dimethylamino)-2-methoxyethyl}phenoxy]azetidin-2-one Step A: 3,3-Diethyl-1-[(R)-α-allyl-(3,4-dioxomethylene) benzylaminocarbonyl]-4-(S)-[4-(1-oxo-2-methoxyethyl) phenoxy]azetidin-2-one According to the procedure of Example 21, Step B, 600 mg (2.05 mmol) of 3,3-diethyl-4-(RS)-[4-(1-oxo-2-methoxyethyl)phenoxy]azetidin-2-one, 490 mg (2.26 mmol) of (R)-α-allyl-3,4-(dioxomethylene)benzyl isocyanate and 29 mg (0.21 mmol) of potassium carbonate in 9 mL of DMF gave, after HPLC purification on 1 kg of silica with 70:30 hexanes: ethyl acetate, 390 mg of an oil.

NMR (CDCl₃; δ from TMS): 1.03 (t, 3H), 1.10 (t, 3H), 1.8–2.1 (m, 4H), 2.58 (t, 2H), 3.52 (s, 3H), 4.68 (s, 3H), 4.89 (q, 1H), 5.1–5.25 (m, 2H), 5.6–5.85 (m, 2H), 5.75 (s, 1H), 5.97 (s, 2H), 6.79 (s, 3H), 6.99 (d, 1H), 7.32 (app d, 2H), 7.95 (app d, 2H).

Step B: 3,3-Diethyl-1-[(R)-α-(n-propyl)-(3,4-dioxomethylene)benzylaminocarbonyl]-4-(S)-[4-(1-(RS)-hydroxy-2-methoxyethyl)phenoxy]azetidin-2-one A solution of 390 mg (0.77 mmol) of 3,3-diethyl-1-[(R)-α-allyl-(3,4-dioxomethylene)benzyl aminocarbonyl]-4-(S)-[4-(1-oxo-2-methoxyethyl)phenoxy]azetidin-2-one in 7.5 mL of methanol and 0.4 mL of water was treated with 180 mg of 5% Ru/C and the mixture placed on a Parr shaker under 40 p.s.i. of hydrogen. After 44 hours, the mixture was filtered through Celite. The filtrate was concentrated in vacuo, the residue was flushed with toluene, and the crude material was purified by flash chromatography on 45 gm of silica eluting with 1 L of 65:35 hexanes: ethyl acetate, to give 310 mg (79%) of an oil.

Step C: 3,3-Diethyl-1-[(R)-α-(n-propyl)-(3,4-dioxomethylene)benzylaminocarbonyl]-4-(S)-[4-{1-(RS)-(N,N-dimethylamino)-2-methoxyethyl}phenoxy]azetidin-2-one According to the procedure given in Example 21, Step D, 111 mg (0.22 mmol) of 3,3-diethyl-1-[(R)-α-(n-propyl)-(3,4-dioxomethylene)benzylaminocarbonyl]-4-(S)-[4-(1-(RS)-(hydroxy)-2-methoxyethyl)phenoxy]aze-tidin-2-one, 128 mg (0.30 mmol) of triphenylphosphine dibromide and ca. 0.4 mL of dimethylamine gave, after purification on 33 gm of silica eluting with 1 L of 98:2 methylene chloride: methanol then 600 mL of 97.5:2.5 methylene chloride: methanol to give 75 mg (64%) of an oil.

NMR (CDCl₃; δ from TMS): d 0.9 (app t, J=7, 6H), 1.05 (t, J=7, 3H), 1.2–1.5 (m, 2H), 1.8–2.1 (m, 6H), 2.18(s, 6H), 3.3 (s, 3H), 3.4 (m, 1H), 3.5–3.8 (m, 2H), 4.85 (q, J=8, 1H), 5.55 (s, 1H), 5.92 (s, 2H), 6.75 (br s, 3H), 6.90 (d, J=8, 1H), 7.1–7.(m, 4H)

Mass Spectrum (FAB): m/Z 540(M+1, 100), 496(19), 494(21), 276(14), 177(55), 135(30).

EXAMPLE 28

3,3-Diethyl-1-[(R)-α-(n-propyl)-(3,4-dioxomethylene)benzylaminocarbonyl]-4-(S)-[4-{1-(RS)-(N-ethyl-N-(methyl)amino)-2-methoxyethyl}phenoxy]azetidin-2-one According to the procedure given in Example 21, Step D, 123 mg (0.24 mmol) of 3,3-diethyl-1-[(R)-α-(n-propyl)-(3, 4-dioxomethylene)benzylaminocarbonyl]-4-(S)-[4-(1-(RS)-(hydroxy)-2-methoxyethyl)phenoxy]azetidin-2-one, 142 mg (0.34 mmol) of triphenyl phosphine dibromide and ca. 0.4 mL of N-methylethylamine gave, after purification by flash chromatography on 32 gm of silica eluting with 1 L of 100:1.75 methylene chloride: methanol, 82 mg (62%) of an oil.

NMR (CDCl$_3$; δ from TMS): 0.9–1.2 (12H), 1.2–1.5 (m, 2H), 1.6–2.2 (m, 6H), 2.28 (s, 3H), 2.3–2.7 (m, 2H), 3.37 (s, 3H), 3.6–3.9 (m, 3H), 4.82 (q, J=8, 1H), 5.65 (s, 1H), 5.99 (s, 2H), 6.82 (br s, 3H), 6.95 (d, J=8, 1H), 7.18–7.4 (m, 4H).

Mass Spectrum (FAB): m/Z 554(M+1, 100), 508(40), 276(22), 177(81).

EXAMPLE 29

3,3-Diethyl-1-[(R)-α-(n-propyl)-(3,4-dioxomethylene)benzylaminocarbonyl]-4-(S)-[4-{1-(RS)-(N-(n-propyl)-N-(methyl)amino)-2-methoxyethyl}phenoxy]azetidin-2-one According to the procedure given in Example 21, Step D, 112 mg. (0.22 mmol) of 3,3-diethyl-1-[(R)-α-(n-propyl)-(3, 4-dioxomethylene)benzylaminocarbonyl]-4-(S)-[4-(1-(RS)-(hydroxy)-2-methoxyethyl)phenoxy]azetidin-2-one, 129 mg (0.31 mmol) of triphenyl phosphine dibromide and ca. 0.4 mL of N-methylpropylamine gave, after purification by flash chromatography on 33 gm of silica eluting with 1 L of 100:1.5 methylene chloride: methanol, 75 mg (60%) of an oil.

NMR (CDCl$_3$; δ from TMS): d 0.8–1.2 (m, 12H), 1.2–1.7 (m, 4H), 1.7–2.2 (m, 6H), 2.25 (s, 3H), 2.2–2.5 (m, 2H), 3.35 (s, 3H), 3.6–3.9 (m, 3H), 4.82 (q, J=8, 1H), 5.64 (s, 1H), 5.95 (s, 2H), 6.80 (br s, 3H), 6.95 (d, J=8, 1H), 7.1–7.4 (m, 4H).

Mass Spectrum (FAB): m/Z 568(M+1, 72), 523(58), 178(100), 177(98), 135(78).

EXAMPLE 30

3,3-Diethyl-1-[(R)-α-(n-propyl)-4-(methyl)benzylaminocarbonyl]-4-(S)-[4-{2-(RS)-(N-(2-methoxyethyl)pyrrolidino)}phenoxy]azetidin-2-one Step A: 4-Benzyloxy-α-cyano-α-(4-morpholino)toluene (See Nate, H. et al Chem Pharm Bull. 1987, 35, 3253) A mixture of 5 gm (23.5 mmol) of 4-benzyloxybenzaldehyde, 57 mL (0.66 mol) of morpholine, 4.9 gm (26 mmol) of p-toluenesulfonic acid and 24 mL of THF was heated to 80° C. under an atmosphere of nitrogen. After 90 min, 2.3 gm (35 mmol) of potassium cyanide in 24 mL of water was added and the temperature was increased until the mixture was at reflux. After 110 min more, the mixture was allowed to cool to room temperature. After adding 30 mL of water, the mixture was extracted with 3×140 mL of ethyl acetate. Each extract was washed with 2×60 mL of water, and the combined organic layers were washed with 30 mL of brine, dried over sodium sulfate, filtered and concentrated in vacuo. The residue was purified by flash chromatography on 243 gm of silica with 4 L of 84:16 hexanes: ethyl acetate to give 6.7 gm of an oil, which was crystallized from hexanes.

NMR (CDCl$_3$; δ from TMS): 2.63 (t, 4H), 3.7–3.9 (m, 4H), 4.82 (s, 1H), 5.15 (s, 2H), 7.05 (app d, 2H), 7.3–7.6 (m, 7H).

Step B: 4-Benzyloxy-γ-cyanopropiophenone

A suspension of 6 gm (19.5 mmol) of 4-benzyloxy-α-cyano-α-(4-morpholino)toluene in 45 mL of THF was treated with 66 mg (1.2 mmol) of potassium hydroxide in 0.4 mL of methanol. To this mixture was added 1.91 mL (29.2 mmol) of acrylonitrile in 12 mL of THF. After 30 min 15 mL of ethyl acetate was added, the mixture was concentrated in vacuo, and the residue was taken up in 150 mL of ethyl acetate and was washed with 2×60 mL of water. The organic layer was washed with brine, dried over sodium sulfate, and concentrated carefully in vacuo (bath temperature less than 34° C.) to give about 12 gm of an oil. This material was taken up in 45 mL of THF, 11 mL of water and 12 mL of acetic acid and was stirred at room temperature. After 24 hr and 48 hr, 4 mL of acetic acid was added. After 4.5 days total, the volume was reduced carefully in vacuo and the residue was taken up in 100 mL of ethyl acetate and 50 mL of 10% aqueous sodium carbonate. The layers were separated and the aqueous phase extracted with 3×80 mL of ethyl acetate. The combined extracts were washed with 70 mL of water, dried over sodium sulfate and concentrated in vacuo, during which time a white solid separated from solution. The solid was taken up in 65 mL of hot ethyl acetate and the resulting solution was allowed to stand overnight. The solid was collected by filtration to give 3.62 gm (70%) of colorless needles. Reprocessing of the mother liquors provided an additional 0.62 gm (12%) of a white powder.

NMR (CDCl$_3$; δ from TMS): d 2.80 (t, 2H), 3.38 (t, 2H), 5.18 (s, 2H), 7.07(app d, 2H), 7.1–7.3 (m, 5H), 7.95 (app d, 2H).

Step C: 4-Hydroxy-γ-cyanopropiophenone

A suspension of 2 gm (7.5 mmol) of 4-benzyloxy-γ-cyanopropiophenone in 60 mL of ethyl acetate was treated with 300 mg of 5% Pd/C and was stirred under one atmosphere of hydrogen for 6.5 hr. The mixture was filtered through Celite and concentrated to give a white solid. The solid was taken up in 20 mL of hot ethyl acetate and the mixture aged first at ambient temperature and then at 5° C. overnight. The solid was collected by filtration to give 937 mg (71%) of a white solid.

NMR (CDCl$_3$; δ from TMS): d 2.82 (t, 2H), 3.39 (t, 2H), 6.95 (app d, 2H), 7.95 (app d, 2H).

Step D: 3,3-Diethyl-4-(RS)-[4-(1-oxo-3-cyanopropyl)phenoxy]azetidin-2-one

To a solution of 0.92 gm (5.25 mmol) of 4-γ-cyanopropiophenone and 1.57 gm (7.88 mmol) of 3,3-diethyl-4-acetoxyazetidin-2-one in 15 mL of acetone was added a solution of 1.09 gm (7.88 mmol) of potassium carbonate in 4.5 mL of water. After 2.5 hr, 20 mL of water was added and the mixture extracted with 3×50 mL of ether. The organic extracts were dried over sodium sulfate, filtered and concentrated in vacuo. The residue was purified by flash chromatography on 164 gm of silica eluting with 3 L of 60:40 hexanes: ethyl acetate then 2.6 L of 50:50 hexanes: ethyl acetate to provide 1.29 gm (82%) of an solid which contained trace impurities by TLC (60:40 hexanes: ethyl acetate)

Step E: 3,3-Diethyl-1-[(R)-α-(allyl)-4-(methyl)benzylaminocarbonyl]-4-(S)-[4-(1-oxo-3-cyanopropyl)phenoxy]azetidin-2-one According to the procedure of Example 21, Step B, 1.29 gm (4.3 mmol) of 3,3-diethyl-4-(RS)-[4-(1-oxo-3-cyanopropyl)phenoxy]azetidin-2-one, 0.965 gm (5.15 mmol) of (R)-α-allyl-4-methylbenzyl isocyanate, 59 mg (0.43 mmol) of potassium carbonate in 20 mL of DMF gave, after EPLC purification on 1 kg of silica eluting with 8 L of 72:28 hexanes: ethyl acetate 1.0 gm of the product as an oil.

NMR (CDCl$_3$; δ from TMS): 1.05 (t, 3H), 1.13 (t, 3H), 1.8–2.1 (m, 4H), 2.39 (s, 3H), 2.62 (t, 2H), 2.80 (t, 2H), 3.37 (t, 2H), 4.98 (q, 1H), 5.1–5.3 (m, 2H), 5.6–5.9 (m, 1H), 5.76 (s, 1H), 7.05 (d, 1H), 7.23 (app s, 4H), 7.35 (app d, 2H), 7.96 (app d, 2H).

Step F: 3,3-Diethyl-1-[(R)-α-(n-propyl)-4-(methyl) benzylaminocarbonyl]-4-(S)-[4-(2-(1-pyrrolino)phenoxy] azetidin-2-one Approximately 1.4 gm of Raney nickel was rinsed 7× with water by decantation until the pH of the supernatent was nearly neutral, and the catalyst was then rinsed 5× with ethanol. The solid so obtained was combined with 0.238 gm (0.49 mmmole) of 3,3-diethyl-1-[(R)-α-(allyl)-4-(methyl) benzylaminocarbonyl]-4-(S)-[4-(1-oxo-3-cyanopropyl) phenoxy]azetidin-2-one in 7 mL of ethanol, and the mixture was stirred under one atmosphere of hydrogen for two hours. The mixture was filtered through Celite and the filtrate was concentrated in vacuo to give ca. 0.23 gm of an oil, which contained minor byproducts by $^1$H NMR. The crude product was carried on immediately in Step G below.

NMR (CDCl$_3$; δ from TMS): 0.9–1.1 (m, 6H), 1.18 (t, 3H), 1.3–1.5 (m, 2H), 1.8–2.3 (m, 6H), 2.42 (s, 3H), 3.0 (t, 3H), 4.14 (t, 3H), 4.93 (q, 1H), 5.75 (s, 1H), 7.04 (d, 1H), 7.2–7.4 (m, 6H), 7.89 (app d, 2H).

Step G: 3,3-Diethyl-1-[(R)-α-(n-propyl)-4-(methyl) benzylaminocarbonyl]-4-(S)-[4-(2-(RS)-pyrrolidino) phenoxy]azetidin-2-one A solution of ca. 2 gm (0.42 mmol) of crude 3,3-diethyl-1-[(R)-α-(n-propyl)-4-(methyl)benzylaminocarbonyl]-4-(S)-[4-(2-(1-pyrroline)phenoxy]azetidin-2-one (from Step F above) in 1.5 mL of methanol was treated with 79 mg (1.26 mmol) of sodium cyanoborohydride and the pH of the solution (determined by spotting onto wet pH paper) was adjusted to ca. 7 by dropwise addition of a solution of acetic acid in methanol. After 22 hr, the mixture was concentrated in vacuo. The residue was treated with 10 mL of saturated aqueous sodium bicarbonate and the aqueous phase extracted with 3×25 mL of ethyl acetate. Each extract was washed with 5 mL of brine, and the combined extracts were dried over sodium sulfate, filtered and concentrated in vacuo. The residue was purified by flash chromatography on 30 gm of silica eluting with 1 L of 100:5:0.2 methylene chloride: methanol: ammonia water to give 147 mg (73%) of an oil.

IR (neat) 3340 cm$^{-1}$ (no —OH absorption). NMR (CDCl$_3$; δ from TMS): 1.03 (app q, 6H), 1.17 (t, 3H), 1.3–1.5 (m, 2H), 1.7–2.35 (m, 10H), 2.40 (s, 3H), 2.98–3.35 (m, 2H), 4.17 (t, 1H), 4.82 (q, 1H), 5.66 (s, 1H), 7.05 (d, 1H), 7.2–7.45 (m, 8H).

Step E: 3,3-Diethyl-1-[(R)-α-(n-propyl)-4-(methyl) benzylaminocarbonyl]-4-(S)-[4-{2-(RS)-(N-(2-methoxyethyl)pyrrolidino)}phenoxy]azetidin-2-one A solution of 147 mg (0.31 mmol) of 3,3-diethyl-1-[(R)-α-(n-propyl)-4-(methyl)benzyl aminocarbonyl]-4-(S)-[4-(2-(RS)-pyrrolidine)phenoxy]azetidin-2-one and 0.054 mL (0.31 mmol) of DIEA in 1 mL of ethanol was treated with 0.029 mL (0.31 mmol) of 2-methoxyethyl bromide. After stirring at room temperature for 17 hours, the solution was placed in an oil bath and the temperature raised to 90° C. over 1 day. The mixture was then cooled, the volatiles removed with a stream of nitrogen and the flask was charged with 1.5 mL of acetonitrile and the same quantities of DIEA and the bromide as given above, and the resulting solution stirred for 15 hr at 50° C. The solution was concentrated in vacuo, the residue was treated with 5 mL of saturated aqueous sodium bicarbonate and the aqueous phase extracted with 3×10 mL of ethyl acetate. The combined organic extracts were dried over sodium sulfate, filtered and concentrated in vacuo. The residue was purified by flash chromatography on 35 gm of silica eluting with 98:2 methylene chloride: methanol to provide 88 mg (53%) of an oil.

NMR (CDCl$_3$; δ from TMS): 0.98 (app q, 6H), 1.14 (t, 3H), 1.2–1.4 (m, 2H), 1.6–2.4 (m, 12H), 2.38 (s, 3H), 2.75–2.9 (m, 1H), 3.26 (t, 1H), 3.35, 3.36 (two s, 3H), 3.38–3.6 (m, 3H), 4.92 (q, 1H), 5.65 (s, 1H), 7.03 (d, 1H), 7.15–7.3 (m, 6H), 7.36 (app d, 2H).

Mass Spectrum (FAB): m/Z 536(M+H), 490(25), 220 (44), 147(27), 105(61).

EXAMPLE 31

(4S)-3,3-Diethyl-1-[(R)-α-(n-propyl)-4-(methyl) benzylaminocarbonyl]-4-[(4-aminomethyl)phenoxy] azetidin-2-one (4S)-3,3-Diethyl-1-[(R)-α-(n-propyl)-4-(methyl)benzyl-aminocarbonyl]-4-[(4-bromomethyl)phenoxy]azetidin-2-one (1.0 g, 2.0 mmol) was dissolved in 25 ml acetone. Sodium azide (195 mg, 3.0 mmol) was added and the solution was heated to reflux for 90 minutes, cooled, filtered to remove solids, and evaporated to dryness. The residue was dissolved in 30 ml ethyl acetate, to which was added 100 mg 10% Pd/C. The mixture was placed on a Parr shaker under 40 psi of hydrogen for three hours. After filtering off the catalyst through Celite and evaporating the solvent, the residue was purified by silica gel chromatography eluting with 10% methanol/chloroform to give 705 mg (85%) of the title compound.

NMR (CDCl$_3$: δ from TMS): 0.90, 0.93, 1.07 (3t, J=8 Hz, 9H), 1.2–1.5 (m, 2H) 1.8–2.1 (m, 6H), 2.34 (s, 3H), 3.8 (br s, 2H), 4.85 (q, J=8 Hz, 1H), 5.59 (s, 1H), 6.97 (d, J=8 Hz, 1H), 7.1–7.4 (m, 8H)

EXAMPLE 32

(4S)-3,3-Diethyl-1-[(R)-α-(n-propyl)-4-(methyl) benzylaminocarbonyl]-4-[(4-(N-acetyl) aminomethyl)phenoxy]azetidin-2-one To a solution of 107 mg (0.244 mmol) of (4S)-3,3-diethyl-1-[(R)-α-(n-propyl)-4-(methyl)benzyl-aminocarbonyl]-4-[(4-aminomethyl)phenoxy]azetidin-2-one in 10 ml of methylene chloride was added 0.035 ml acetic anhydride (0.37 mmol) and 1 ml pyridine. The reaction was stirred at rt for 3 hrs and was poured onto 25 ml ice/2N HCl. The product was extracted with ethyl acetate (75 ml) and the organic phase was washed with 10 ml of brine, dried over magnesium sulfate, filtered and evaporated. The product was purified by prep TLC using 5% methanol/chloroform as eluent to yield 77 mg (67%) of the title compound.

NMR (CDCl$_3$; δ from TMS): 0.90, 0.93, 1.07 (3t, J=8 Hz, 9H), 1.2–1.5 (m, 2H), 1.8–2.1 (m, 6H), 2.0 (s, 3H), 2.3 (s, 3H), 4.35 (d, J=5.8 Hz, 2H), 4.85 (q, J=8 Hz, 1H), 5.59 (s, 1H), 5.7 (br, 1H), 6.97 (d, J=8 Hz, 1H), 7.1–7.4 (m, 8H)

EXAMPLE 33

(4S)-3,3-Diethyl-1-[(R)-α-(n-propyl)-4-(methyl) benzylaminocarbonyl]-4-[(4-((N-methyl) aminocarbonyl)aminomethyl)phenoxy]azetidin-2-one To a solution of 104 mg (0.24 mmol) of (4S)-3,3-diethyl-1-[(R)-α-(n-propyl)-4-(methyl)benzylaminocarbonyl]-4-[(4-aminomethyl)phenoxy]azetidin-2-one in 10 ml of methylene chloride was added 0.03 ml of methyl isocyanate (0.38 mmol). The reaction was stirred under nitrogen at rt for 2 hrs. Water (25 mL) was added, and the product was extracted with ethyl acetate. The organic layer was washed with saturated sodium bicarbonate, 1N HCl, and brine, and dried over magnesium sulfate. After evaporation, the residue was purified by prep TLC using 5% methanol/chloroform as eluent to yield 76 mg (64%) of the title compound.

NMR (CDCl$_3$; δ from TMS): 0.90, 0.93, 1.07 (3t, J=8 Hz, 9H), 1.2–1.5 (m, 2H), 1.8–2.1 (m, 6H), 2.3 (s, 3H), 2.75 (d, J=5 Hz, 3H), 4.29 (br, 1H), 4.30 (d, J=5 Hz, 2H), 4.6 (br, 1H), 4.85 (q, J=8 Hz, 1H), 5.59 (s, 1H), 6.97 (d, J=8 Hz, 1H), 7.1–7.4 (m, 8H)

EXAMPLE 34

(4S)-3,3-Diethyl-1-[(R)-α-(n-propyl)-4-(methyl) benzylaminocarbonyl]-4-[(4-((N-propyl) aminocarbonyl)aminomethyl)phenoxy]azetidin-2-one Following the procedure in Example 32, 165 mg (0.38 mmol) of (4S)-3,3-diethyl-1-[(R)-α-(n-propyl)-4-(methyl)benzyl-aminocarbonyl]-4-[(4-aminomethyl)phenoxy]azetidin-2-one was reacted with 0.05 ml (0.53 mmol) of n-propyl isocyanate to yield 130 mg (65%) of the title compound.

NMR (CDCl$_3$; δ from TMS): 0.90, 0.93, 1.07 (4t, J=8 Hz, 12H), 1.2–1.5 (m, 4H), 1.8–2.1 (m, 6H), 2.3 (s, 3H), 4.25 (d, J=5 Hz, 2H), 4.4 (br, t, 1H), 4.6 (br, 1H), 4.85 (q, J=8 Hz, 1H), 5.59 (s, 1H), 6.97 (d, J=8 Hz, 1H), 7.1–7.4 (m, 8H)

EXAMPLE 35

(4S)-3,3-Diethyl-1-[(R)-α-(n-propyl)-4-(methyl) benzylaminocarbonyl]-4-[(4-((N-isopropyl) aminocarbonyl)aminomethyl)phenoxy]azetidin-2-one Following the procedure in Example 32, 125 mg (0.285 mmol) of (4S)-3,3-diethyl-1-[(R)-α-(n-propyl)-4-(methyl)benzyl-aminocarbonyl]-4-[(4-aminomethyl)phenoxy]azetidin-2-one was reacted with 0.04 ml (0.41 mmol) of isopropyl isocyanate to yield 130 mg (74% of the title compound.

NMR (CDCl$_3$; δ from TMS): 0.90, 0.93, 1.07 (3t, J=8 Hz, 9H)), 1.1 (d, J=4 Hz, 6H), 1.2–1.5 (m, 2H), 1.8–2.1 (m, 6H), 2.3 (s, 3H), 3.85 (m, 1H), 4.07 (br, 1H), 4.3 (d, J=5 Hz, 2H), 4.5 (br, 1H), 4.85 (q, J=8 Hz, 1H), 5.59 (s, 1H), 6.97 (d, J=8 Hz, 1H), 7.1–7.4 (m, 8H)

EXAMPLE 36

(4S)-3,3-Diethyl-1-[(R)-α-(n-propyl)-4-(methyl) benzylaminocarbonyl]-4-[(4-((N-benzyl) aminocarbonyl)aminomethyl)phenoxy]azetidin-2-one Following the procedure in Example 32, 127 mg (0.29 mmol) of (4S)-3,3-diethyl-1-[(R)-α-(n-propyl)-4-(methyl)benzyl-aminocarbonyl]-4-[(4-aminomethyl)phenoxy]azetidin-2-one was reacted with 0.075 ml (0.6 mmol) of benzyl isocyanate to yield 120 mg (73%) of the title compound.

NMR (CDCl$_3$; δ from TMS): 0.90, 0.93, 1.07 (3t, J=8 Hz, 9H), 1.2–1.5 (m, 2H), 1.8–2.1 (m, 6H), 2.34 (s, 3H), 4.28 (d, J=5.8 Hz, 2H), 4.34 (d, J=6.2 Hz, 2H), 4.7 (br, 2H), 4.8 (q, J=8 Hz, 1H), 5.59 (s, 1H), 6.97 (d, J=8 Hz, 1H), 7.1–7.4 (m, 13H)

EXAMPLE 37

(4S)-3,3-Diethyl-1-[(R)-α-(n-propyl)-4-(methyl) benzyl-aminocarbonyl]-4-[(4-((N,N-dimethyl) aminomethylcarbonyl)aminomethyl)phenoxy] azetidin-2-one To a solution of 107 mg (0.25 mmol) (4S)-3,3-diethyl-1-[(R)-α-(n-propyl)-4-(methyl)benzyl-aminocarbonyl]-4-[(4-aminomethyl)phenoxy]azetidin-2-one in 5 ml methylene chloride was added 41 mg (0.29 mmol) of dimethyl glycine HCl salt, followed by 94 mg (0.5 mmol) 1-ethyl-3-(3-dimethylaminopropyl)carbodiimide (EDC) and catalytic (5 mg) 4-(N,N-dimethyl)aminopyridine (DMAP). The reaction was stirred at rt for 2 hrs, then diluted with 100 ml ethyl acetate, washed with 25 ml saturated sodium bicarbonate, water, and brine, and dried over magnesium sulfate. After evaporation, the residue was purified by prep TLC using 5% methanol/chloroform as eluent to yield 109 mg (85%) of the title compound.

NMR (CDCl$_3$; δ from TMS): 0.90, 0.93, 1.07 (3t, J=8 Hz, 9H), 1.2–1.5 (m, 2H), 1.8–2.1 (m, 6H), 2.25 (s, 6H), 2.34 (s, 3H), 2.97 (s, 2H), 4.39 (d, J=5.7 Hz, 2H), 4.8 (q, J=8 Hz, 1H), 5.59 (s, 1H), 6.97 (d, J=8 Hz, 1H), 7.1–7.2 (m, 8H), 7.4 (br, 1H)

EXAMPLE 38

(4S)-3,3-Diethyl-1-[(R)-α-(n-propyl)-4-(methyl) benzyl-aminocarbonyl]-4-[(4-((2((N,N-diethyl) amino)ethylcarbonyl)aminomethyl)phenoxy] azetidin-2-one Following the procedure in Example 37, 94 mg (0.22 mmol) of (4S)-3,3-diethyl-1-[(R)-α-(n-propyl)-4-(methyl)benzyl-aminocarbonyl]-4-[(4-aminomethyl)phenoxy]azetidin-2-one was reacted with 47 mg (0.26 mmol) of 3-(N,N-diethyl)aminopropionic acid HCl salt, 83 mg (0.43 mmol) EDC, and catalytic DMAP to yield 88 mg (72%) of the title compound.

NMR (CDCl$_3$; δ from TMS): 0.89, 0.90, 0.93, 1.07 (4t, J=8 Hz, 15H), 1.2–1.5 (m, 2H), 1.8–2.1 (m, 6H), 2.34 (s, 3H), 2.4 (t, J=6 Hz, 2H), 2.53 (q, J=8 Hz, 4H), 2.7 (t, J=6 Hz, 2H), 4.3 (d, J=5.3 Hz, 2H), 4.8 (q, J=8 Hz, 1H), 5.59 (s, 1H), 6.97 (d, J=8z, 1H), 7.1–7.3 (m, 8H), 8.7 (br, 1H)

EXAMPLE 39

(4S)-3,3-Diethyl-1-[(R)-α-(n-propyl)-4-(methyl) benzylaminocarbonyl]-4-[(4-((N-benzyl-N-methylcarbonyl)aminomethyl)phenoxy]azetidin-2-one Following the procedure in Example 37, 40 mg (0.09 mmol) of (4S)-3,3-diethyl-1-[(R)-α-(n-propyl)-4-(methyl)benzyl-aminocarbonyl]-4-[(4-aminomethyl)phenoxy]azetidin-2-one was reacted with 24.5 mg (0.13 mmol) of 3-(N-benzyl-N-methyl)glycine, 26.5 mg (0.14 mmol) EDC, and catalytic DMAP to yield 54 mg (99%) of the title compound.

NMR (CDCl$_3$; δ from TMS): 0.90, 0.93, 1.07 (3t, J=8 Hz, 9H), 1.2–1.5 (m, 2H), 1.8–2.1 (m, 6H), 2.25 (s, 3H), 2.34 (s, 3H) 3.1 (s, 2H), 3.5 (s, 2H), 4.4 (d, J=6 Hz, 2H), 4.8 (q, J=8 Hz, 1H), 5.59 (s, 1H), 6.97 (d, J=8 Hz, 1H), 7.1–7.4 (m, 13H), 7.4 (br, 1H)

EXAMPLE 40

(4S)-3,3-Diethyl-1-[(R)-α-(n-propyl)-4-(methyl) benzylaminocarbonyl]-4-[(4-((3-pyridyl) methylcarbonyl)aminomethyl)phenoxy]azetidin-2-one Following the procedure in Example 37, 88 mg (0.20 mmol) of (4S)-3,3-diethyl-1-[(R)-α-(n-propyl)-4-(methyl)benzyl-aminocarbonyl]-4-[(4-aminomethyl)phenoxy]azetidin-2-one was reacted with 42 mg (0.24 mmol) of 3-pyridylacetic acid HCl salt, 77 mg (0.40 mmol) EDC, and catalytic DMAP to yield 92 mg (83%) of the title compound.

NMR (CDCl₃; δ from TMS): 0.90, 0.93, 1.07 (3t, J=8 Hz, 9H), 1.2–1.5 (m, 2H), 1.8–2.1 (m, 6H), 2.34 (s, 3H), 3.55 (s, 2H), 4.35 (d, J=5.2 Hz), 4.8 (q, J=8 Hz, 1H), 5.59 (s, 1H), 5.7 (br, 1H) 6.97 (d, J=8 Hz, 1H), 7.1–7.2 (m, 8H), 7.25, 7.6, 8.5 (3 br, 4H)

EXAMPLE 41

(4S)-3,3-Diethyl-1-[(R)-α-(n-propyl)-4-(methyl) benzylaminocarbonyl]-4-[(4-((4-pyridyl) methylcarbonyl)aminomethyl)phenoxy]azetidin-2-one Following the procedure in Example 37, 104 mg (0.24 mmol) of (4S)-3,3-diethyl-1-[(R)-α-(n-propyl)-4-(methyl) benzyl-aminocarbonyl]-4-[(4-aminomethyl)phenoxy] azetidin-2-one was reacted with 63 mg (0.36 mmol) of 4-pyridylacetic acid HCl salt, 93 mg (0.48 mmol) EDC, and catalytic DMAP to yield 110 mg (82%) of the title compound.

NMR (CDCl₃; δ from TNS): 0.90, 0.93, 1.07 (3t, J=8 Hz, 9H), 1.2–1.5 (m, 2H), 1.8–2.1 (m, 6H), 2.34 (s, 3H), 3.55 (s, 2H) 4.35 (d, J=5.2 Hz), 4.8 (q, J=8 Hz, 1H), 5.59 (s, 1H), 5.7 (br, 1H), 6.97 (d, J=8 Hz, 1H), 7.1–7.2 (m, 8H), 7.2, 8.5 (2 br, 4H)

EXAMPLE 42

(4S)-3,3-Diethyl-1-[(R)-α-(n-propyl)-4-(methyl) benzylaminocarbonyl]-4-[(4-((4-imidazolyl) methylcarbonyl)aminomethyl)phenoxy]azetidin-2-one Following the procedure in Example 37, 102 mg (0.23 mmol) of (4S)-3,3-diethyl-1-[(R)-α-(n-propyl)-4-(methyl) benzyl-aminocarbonyl]-4-[(4-aminomethyl)phenoxy] azetidin-2-one was reacted with 45 mg (0.28 mmol) of 4-imidazoleacetic acid HCl salt, 90 mg (0.47 mmol) EDC, and catalytic DMAP to yield 70 mg (50%) of the title compound.

NMR (CDCl₃; δ from TMS): 0.90, 0.93, 1.07 (3t, J=8 Hz, 9H), 1.2–1.5 (m, 2H), 1.8–2.1 (m, 6H), 2.34 (s, 3H), 3.55 (s, 2H) 4.35 (d, J=5.2 Hz), 4.8 (q, J=8 Hz, 1H), 5.5 (br, 1H), 5.59 (s, 1H), 6.8 (s, 1H), 6.97 (d, J=8 Hz, 1H), 7.1–7.2 (m, 8H), 7.4 (br, 1H), 7.5 (s, 1H)

EXAMPLE 43

(4S)-3,3-Diethyl-1-[(R)-α-n-propyl-(4-methyl) benzylaminocarbonyl]-4-[(4-((4-dimethylaminocarbonyl)piperazin-1-yl)methyl) phenoxy]azetidin-2-one Step A: (4S)-3,3-Diethyl-1-[(R)-α-n-propyl-(4-methyl) benzylaminocarbonyl]-4-[(4-((4-benzyloxycarbonyl) piperazin-1-yl)methyl)phenoxy]azetidin-2-one To a solution of (4S)-3,3-diethyl-1-[(R)-α-n-propyl-(4-methyl)benzylaminocarbonyl]-4-[(4-bromomethyl) phenoxy]azetidin-2-one (1.9 gm, 3.8 mmol) in THF (20 mL) and MeCN (20 mL) was added N-benzyloxycarbonylpiperazine (1.0 gm, 4.6 mmol) and diisopropylethylamine (740 mg, 5.7 mmol) and the reaction was stirred for 2.5 hrs at room temperature. The volatiles were evaporated in vacuo and the residue taken up in CH₂Cl₂ and washed with potassium carbonate solution and brine. The aqueous layers were consecutively extracted with another portion of CH₂Cl₂ and the pooled CH₂Cl₂ layers were dried over sodium sulfate and evaporated. The residue was purified by preparative TLC eluting with 50% ethyl acetate/hexanes to give 2.4 gm (98%) of the title compound as an oil.

NMR (CDCl₃; δ from TMS): 0.90, 0.94, 1.07 (3 t, J =8 Hz, 9H), 1.2–1.5 (m, 2H), 1.6–2.0 (m, 6H), 2.33 (s, 3H), 2.38 (m, 4H), 3.45 (s, 2H), 3.50 (br t, J=6 Hz, 4H), 4.82 (q, J=8 Hz, 1H), 5.12 (s, 2H), 5.55 (s, 1H), 6.95 (d, J=8 Hz, 1H), 7.1–7.3 (m, 8H).

Step B: (4S)-3,3-Diethyl-1-[(R)-α-n-propyl-(4-methyl) benzylaminocarbonyl]-4-[(4-piperazin-1-yl)methyl) phenoxy]azetidin-2-one A solution of (4S)-3,3-diethyl-1-[(R)-α-n-propyl-(4-methyl)benzylaminocarbonyl]-4-[(4-((4-benzyloxycarbonyl)piperazin-1-yl)methyl)phenoxy] azetidin-2-one (2.4 gm, 3.7 mmol) in ethanol (30 mL) and ethyl acetate (15 mL) was hydrogenated at 40 p.s.i. over 10% Pd/C (200 mg) for 4 hrs. The reaction was then filtered and evaporated to give 2.1 gm of crude product as an oil which was used directly in the next step.

Step C: (4S)-3,3-Diethyl-1-[(R)-α-n-propyl-(4-methyl) benzylaminocarbonyl]-4-[(4-((4-dimethylaminocarbonyl) piperazin-1-yl) methyl)phenoxy]azetidin-2-one The product from Step B (1.1 gm, 2.17 mmol) was taken up in CH₂Cl₂ and diisopropylethylamine (420 mg, 3.3 mmol), dimethylcarbamoyl chloride (350 mg, 3.3 mmol) and a trace of DMAP were added and the reaction was heated at 45° C. for 16 hrs. The reaction was then poured into ice water and extracted twice with CH₂Cl₂. The CH₂Cl₂ layers were washed with brine, dried over Na₂SO₄ and evaporated. The residue as purified by flash chromatography eluting with ethyl acetate, then 10% methanol/90% ethyl acetate to afford 920 mg (60%) of the title compound.

NMR (CDCl₃; δ from TMS): 0.91, 0.95, 1.08 (3 t, J=8 Hz, 9H), 1.2–1.5 (m, 2H), 1.6–2.0 (m, 6H), 2.33 (s, 3H), 2.42 (m, 4H), 2.81 (s, 6H), 3.25 (br t, J=6 Hz, 4H), 3.47 (s, 2H), 4.82 (q, J=8 Hz, 1H), 5.57 (s, 1H), 6.95 (d, J=8 Hz, 1H), 7.1–7.3 (m, 8H).

EXAMPLE 44

(4S)-3,3-Diethyl-1-[(R)-α-n-propyl-3,4-methylenedioxy)benzylaminocarbonyl]-4-[(4-((4-diemthylaminocarbonyl)piperazin-1-yl)methyl) phenoxy]azetidin-2-one Following essentially the same procedure as in Example 43, Steps A–C, except starting with (4S)-3,3-diethyl-1-[(R)-α-n-propyl-3(3,4-methylenedioxy)benzylaminocarbonyl]-4-[(4-bromomethyl)phenoxy]-azetidin-2-one, the title compound was prepared.

NMR (CDCl₃; δ from TMS): 0.91, 0.96, 1.08 (3 t, J=8 Hz, 9H), 1.2–1.5 (m, 2H), 1.6–2.0 (m, 6H), 2.42 (m, 4H), 2.81 (s, 6H), 3.25 (br t, J=6 Hz, 4H), 3.47 (s, 2H), 4.76 (q, J=8 Hz, 1H), 5.57 (s, 1H), 5.93 (s, 2H), 6.77 (s, 3H), 6.91 (d, J=8 Hz, 1H), 7.1–7.3 (m, 4H).

What is claimed is:

1. A compound of the Formula (I)

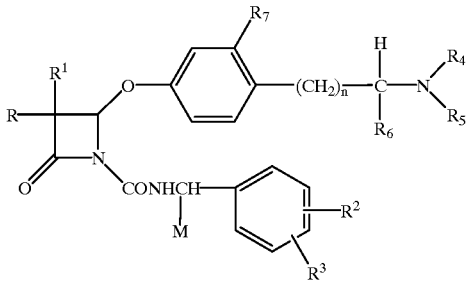

or a pharmaceutically acceptable salt thereof wherein

R is $C_{1-6}$ alkyl;
$R^1$ is $C_{1-6}$ alkyl or $C_{1-6}$ alkoxy-$C_{1-6}$ alkyl;
M is
(1) $C_{1-6}$ alkyl,
(2) hydroxy $C_{1-6}$ alkyl,
(3) halo $C_{1-6}$ alkyl,
(4) $C_{2-6}$ alkenyl, or
(5) $C_{1-6}$ alkoxy-$C_{1-6}$ alkyl;
$R^2$ and $R^3$ are each independently
(1) hydrogen,
(2) $C_{1-6}$ alkyl,
(3) halo,
(4) carboxy,
(5) $C_{1-6}$ alkoxy,
(6) phenyl,
(7) $C_{1-6}$ alkylcarbonyl,
(8) di-($C_{1-6}$alkyl)amino, or
$R^2$ and $R^3$ are joined together to form the group methylenedioxy or $R^2$ and $R^3$ together with the carbon atoms to which they are attached form a furan ring;
$R_7$ is
(a) hydrogen,
(b) halo,
(c) $C_{1-3}$alkyl,
(d) hydroxy, or
(e) $C_{1-3}$alkoxy; and
n is 0;
$R_4$ is selected from
(a) hydrogen,
(b) $C_{1-6}$ alkyl,
(c) $C_{1-6}$ alkyloxy $C_{2-3}$ alkyl; or
(d) cyclopropyl,
$R_5$ is selected from
(a) hydrogen,
(b) $C_{1-6}$ alkyl,
(c) $C_{1-6}$ alkyloxy $C_{2-3}$ alkyl,
(d)

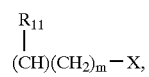

wherein m is 0, 1, 2, 3 or 4,
such that when m is 1, 2, 3 or 4,
X is (1)

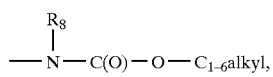

(2) —O—C(O)—$C_{1-6}$alkyl,
(3) —O—$R_8$, wherein $R_8$ and $R_{11}$ are defined immediately below, or O—$R_8$ and $R_{11}$ may be joined together to form a saturated ring of 5–7 atoms containing a single heteroatom which is oxygen, and the rest of the atoms are carbon
(4)

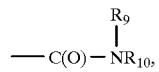

wherein $R_8$, $R_9$ and $R_{10}$, $R_{11}$ are each independently hydrogen, $C_{1-6}$alkyl, phenyl or benzyl, or wherein $R_9$ and $R_{10}$ are joined together with the nitrogen to which they are attached to form a saturated monocyclic ring of 5 to 7 atoms containing one or two heteroatoms selected from
(a) morpholinyl,
(b) thiomorpholinyl,
(c) piperadinyl,
(d) pyrrolidinyl,
said ring optionally substituted with $C_{1-3}$ alkyl or $R_8$ and $R_4$ are joined together to form a piperazinyl or homopiperazinyl ring, said ring optionally substituted with $C_{1-3}$ alkyl,
(5)

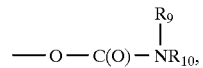

(6)

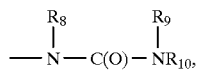

(7)

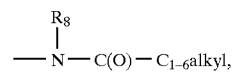

(8) —OH,
(9) $C_{1-3}$ alkyloxy-$C_{1-3}$ alkyloxy,
(10) —C(O)OH, —C(O)$OR_8$, or C(O)$C_{1-6}$ alkyl
(11) —S—$C_{1-6}$alkyl,
(12) —S(O)—$C_{1-6}$alkyl, or
(13) —S(O)$_2$—$C_{1-6}$alkyl;
and when m is 0,
X is —C(O)OH—C(O)$OR_8$, C(O)$C_{1-6}$ alkyl or

(e) C(O)—Y, wherein Y is
(1) hydrogen, (2) $C_{1-6}$alkyl,
(3)

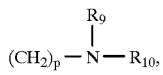

wherein p is 0, 1 or 2,
(4) pyridylmethyl,
(5) imidazolyl methyl,
(f) mono or di substituted benzyl or mono substituted pyridylmethyl, wherein the substitutent is
(1) hydrogen,
(2) halo,
(3) $C_{1-6}$ alkyl, or
(4) $C_{1-6}$ alkylcarbonylamino;

$R_6$ is selected from hydrogen, $C_{1-4}$ alkyl, and $C_{1-3}$ alkoxy $C_{1-3}$alkyl; or wherein $R_4$ and $R_5$ are joined together to form a mono or di substituted ring of 5, 6, or 7 atoms selected from
(1) piperidinyl,
(2) piperazinyl,
(3) morpholinyl,
(4) thiomorpholinyl,
(5) pyrrolidinyl,
(6) pyrryl, and
(7) imidazolyl,
wherein the substituents are each selected from the group consisting of hydrogen, hydroxy, hydroxymethyl, $C_{1-3}$ alkyl, $C_{1-3}$ alkyloxy, $C_{1-3}$ alkyloxymethyl, $C_{1-6}$ alkylcarbonyl; or $R_4$ and $R_6$ are joined together to form an unsubstituted monocyclic ring of 5, 6, or 7 atoms including the atoms to which they are attached, said ring optionally having a second hetero atom selected from O or N or S, and said ring being either saturated or unsaturated.

2. A compound according to claim 1 wherein
R is $C_{1-6}$ alkyl;
$R^1$ is $C_{1-6}$ alkyl or $C_{1-6}$ alkoxy-$C_{1-6}$ alkyl;
M is
(1) $C_{1-6}$ alkyl,
(2) hydroxy $C_{1-6}$ alkyl,
(3) halo $C_{1-6}$ alkyl,
(4) $C_{2-6}$ alkenyl, or
(5) $C_{1-6}$ alkoxy-$C_{1-6}$ alkyl;
$R^2$ and $R^3$ are each independently
(1) hydrogen,
(2) $C_{1-6}$ alkyl,
(3) halo,
(4) carboxy,
(5) $C_{1-6}$ alkoxy,
(6) phenyl,
(7) $C_{1-6}$ alkylcarbonyl,
(8) di-($C_{1-6}$alkyl)amino, or $R^2$ and $R^3$ are joined together to form the group methylenedioxy or $R^2$ and $R^3$ together with the carbon atoms to which they are attached form a furan ring;
$R_7$ is
(a) hydrogen,
(b) halo,
(c) $C_{1-3}$alkyl,
(d) hydroxy, or
(e) $C_{1-3}$alkoxy; and
n is 0;
$R_4$ is selected from
(a) hydrogen,
(b) $C_{1-6}$ alkyl,
(c) CI-6 alkyloxy $C_{2-3}$ alkyl; or
(d) cyclopropyl,
$R_5$ is selected from
(a) hydrogen,
(b) $C_{1-6}$ alkyl,
(c) $C_{1-6}$ alkyloxy $C_{2-3}$ alkyl,
(d) (CH)(CH$_2$)$_m$—X, wherein m is 0, 1, 2, 3 or 4,
such that when m is 1, 2, 3 or 4,
X is
(1) —N(R$_8$)C(O) —O—C$_{1-6}$alkyl,
(2) —O—C(O)—C$_{1-6}$alkyl,
(3) —O—R$_8$, wherein R$_8$ and R$_{11}$ are defined immediately below, or O—R$_8$ and R$_{11}$ may be joined together to form a saturated ring of 5–7 atoms containing a single heteroatom which is oxygen, and the rest of the atoms are carbon,
(4) —C(O)—N(R$_9$)R$_{10}$, wherein R$_8$, R$_9$ and R$_{10}$, R$_{11}$ are each independently hydrogen, C$_{1-6}$alkyl, phenyl or benzyl, or wherein R$_9$ and R$_{10}$ are joined together with the nitrogen to which they are attached to form a saturated monocyclic ring of 5 to 7 atoms containing one or two heteroatoms selected from
(a) morpholinyl,
(b) thiomorpholinyl,
(c) piperidinyl
(d) pyrrolidinyl
said ring optionally substituted with C$_{1-3}$ alkyl,
(5) —O—C(O)—N(R$_9$)(R$_{10}$)
(6) —N(R$_8$)—C(O)—N(R$_9$)(R$_{10}$),
(7) —N(R$_8$)—C(O)—C$_{1-6}$alkyl,
(8) —OH,
(9) C$_{1-3}$ alkyloxy-C$_{1-3}$ alkyloxy,
(10) —C(O)OH, C(O)R$_8$, or C(O) C$_{1-6}$ alkyl
(11) —S—C$_{1-6}$alkyl,
(12) —S(O)—C$_{1-6}$alkyl, or
(13) —S(O)$_2$—C$_{1-6}$alkyl; and
when m is 0,
X is —C(O)OH; C(O) OR$_8$, —C(O)C$_{1-6}$ alkyl or —C(O) N(R$_9$)(R$_{10}$);
(e) C(O)—Y, wherein Y is
(1) hydrogen,
(2) C$_{1-6}$alkyl,
(3) (CH$_2$)$_p$—N(R$_9$)(R$_{10}$), wherein p is 0, 1 or 2,
(4) pyridylmethyl,
(5) imidazolyl methyl,
(f) mono or di substituted benzyl or mono substituted pyridylmethyl, wherein the substitutent is
(1) hydrogen,
(2) halo,
(3) C$_{1-6}$ alkyl, or
(4) C$_{1-6}$ alkylcarbonylamino;
R$_6$ is selected from hydrogen, C$_{1-4}$ alkyl, and C$_{1-3}$alkoxy C$_{1-3}$alkyl; or wherein R$_4$ and R$_5$ are joined together to form a mono or di substituted ring of 5, 6, or 7 atoms selected from
(1) piperidinyl,
(2) piperazinyl,
(3) morpholinyl,
(4) thiomorpholinyl,
(5) pyrroylidinyl,
(6) pyrryl, and
(7) imidazolyl,
wherein the substituents are each selected from the group consisting of hydrogen, hydroxy, hydroxymethyl, $C_{1-3}$ alkyl, $C_{1-3}$ alkyloxy, $C_{1-3}$ alkyloxymethyl, $C_{1-6}$ alkylcarbonyl.

3. A compound according to claim 1 selected from the group consisting of:

(a) (4S)-3,3-Diethyl-1-[(R)-α-n-propyl-(4-methyl)benzylaminocarbonyl]-4-[(4-((4-dimethylaminocarbonyl)piperazin-1-yl)methyl)-phenoxy]azetidin-2-one;

(b) (4S)-3,3-Diethyl-1-[(R)-α-n-propyl-(3,4-methylenedioxy)benzylaminocarbonyl]-4-[(4-((4-dimethylaminocarbonyl)piperazin-1-yl)methyl)-phenoxy]azetidin-2-one;

(c) (4S)-3,3-Diethyl-1-[(R)-α-n-propyl-(4-methyl)benzylaminocarbonyl]-4-[(4-(2-methoxyethyl)ethylaminomethyl)phenoxy]azetidin-2-one;

(d) (4S)-3,3-Diethyl-1-[(R)-α-n-propyl-(4-methyl)benzylaminocarbonyl]-4-[(4-((2-thioethyl)ethyl)methylaminomethyl)phenoxy]azetidin-2-one, S-oxide;

(e) (4S)-3,3-Diethyl-1-[(R)-α-n-propyl-(4-methyl)benzylaminocarbonyl]-4-[(4-((2-thioethyl)ethyl)methylaminomethyl)phenoxy]azetidin-2-one, S-dioxide;

(f) (4S)-3,3-Diethyl-1-[(R)-α-n-propyl-(4-methyl)benzylaminocarbonyl]-4-[(R,S)-4-((1-(2-methoxyethyl)methylaminoethyl)phenoxy]azetidin-2-one;

(g) (4S)-3,3-Diethyl-4-{(S)-4-[1-((2-methoxyethyl)methylamino)ethyl]phenoxy}-1-[(R)-α-n-propyl-(4-methyl)benzylaminocarbonyl]azetidin-2-one;

(h) (4S)-3,3-Diethyl-4-{(R)-4-[1-((2-methoxyethyl)methylamino)ethyl]phenoxy}-1-[(R)-α-n-propyl-(4-methyl)-benzylaminocarbonyl]azetidin-2-one; and (i) 3,3-Diethyl-1-[(R)-α-(n-propyl)-4-(methyl)benzylarminocarbonyl]-4-[4-(1-(R,S)-((2-(dimethylaminocarbonyloxy)ethyl)methylamino)ethyl)phenoxy]azetidin-2-one.

4. A compound according to claim 1 wherein

R is $C_{1-3}$ alkyl;

$R_1$ is $C_{1-3}$ alkyl;

M is
(a) $C_{1-6}$ alkyl, or
(b) $C_{2-6}$ alkenyl;

$R^2$ is
(a) hydrogen
(b) $C_{1-6}$ alkyl, or $C_{1-6}$ alkoxy, and $R^3$ is hydrogen, or $R^2$ and $R^3$ are joined together to form the group methylenedioxy or $R^2$ and $R^3$ together with the carbon atoms to which they are attached form a furan ring;

$R_4$ is selected from
(a) hydrogen,
(b) $C_{1-3}$ alkyl, and
(c) $C_{1-3}$ alkoxy $C_{2-3}$ alkyl;

$R_5$ is selected from
(a) hydrogen,
(b) $C_{1-6}$ alkyl,
(c) $C_{1-6}$ alkyloxy $C_{2-3}$ alkyl,
(d) $CH_2$—$(CH_2)_m$—X, wherein m is 0, 1 or 2, such that when m is 1 or 2, X is
(1) —O—C(O)—$C_{1-6}$alkyl,
(2) —O—$R_8$, (3)
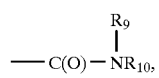
—C(O)—$NR_{10}$, (4)
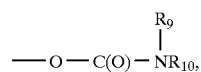
—O—C(O)—$NR_{10}$, wherein $R_8$, $R_9$ and $R_{10}$ are each independently hydrogen or $C_{1-6}$alkyl, (5)
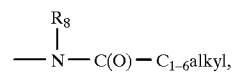
—N—C(O)—$C_{1-6}$alkyl, (6) —$C_{1-3}$alkyloxyethyl,
(7) —S—$C_{1-6}$alkyl,
(8) —S(O)—$C_{1-6}$alkyl, or
(9) —S(O)$_2$—$C_{1-6}$alkyl;

(10)
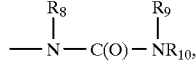
—N—C(O)—$NR_{10}$, and when m is 0,

X is —C(O)OH or

—C(O)$NR_9$
  |
  $R_{10}$;

(e) mono substituted benzyl or mono substituted pyridylmethyl, wherein the substitutent is
(1) hydrogen,
(2) halo,
(3) $C_{1-6}$ alkyl, or
(4) $C_{1-6}$ alkylcarbonylamino;

n is 0, and $R_6$ is selected from hydrogen, $C_{1-4}$ alkyl, and $C_{1-3}$ alkoxy $C_{1-3}$alkyl; or $R_4$ and $R_5$ or $R_9$ and $R_{10}$ are joined together with the nitrogen to which they are attached to form a mono or disubstituted ring selected from
(a) piperidinyl,
(b) pyrrolidinyl, and
(c) morpholinyl; or $R_4$ and $R_6$ are joined together to form a monocyclic ring of 5 to 6 atoms including the atoms to which they are attached, said ring optionally having a second hetero atom selected from O or N.

5. A compound according to claim 1 wherein $R_6$ is selected from hydrogen, $C_{1-4}$ alkyl, and $C_{1-3}$ alkoxy $C_{1-3}$alkyl;

R is $C_{1-6}$ alkyl;

$R_1$ is $C_{1-6}$ alkyl or $C_{1-6}$ alkoxy-$C_{1-6}$ alkyl;

M is
(1) $C_{1-6}$ alkyl,
(2) hydroxy $C_{1-6}$ alkyl, (3) halo $C_{1-6}$ alkyl,
(4) $C_{2-6}$ alkenyl, or
(5) $C_{1-6}$ alkoxy-$C_{1-6}$ alkyl;

$R^2$ and $R^3$ are each independently
(1) hydrogen,
(2) $C_{1-6}$ alkyl,
(3) halo,
(4) carboxy,
(5) $C_{1-6}$ alkoxy,
(6) phenyl,
(7) $C_{1-6}$ alkylcarbonyl,
(8) di-($C_{1-6}$alkyl)amino, or $R^2$ and $R^3$ are joined together to form the group methylenedioxy or $R^2$ and $R^3$ together with the carbon atoms to which they are attached form a furan ring;

$R_7$ is
(a) hydrogen,
(b) halo,
(c) $C_{1-3}$alkyl,
(d) hydroxy, or
(e) $C_{1-3}$alkoxy; and n is 0;

$R_4$ is selected from
(a) hydrogen,
(b) $C_{1-6}$ alkyl,
(c) $C_{1-6}$ alkyloxy $C_{2-3}$ alkyl; or
(d) cyclopropyl, $R_5$ is selected from
(a) hydrogen,
(b) $C_{1-6}$ alkyl,
(c) $C_{1-6}$ alkyloxy $C_{2-3}$ alkyl,
(d) $(CH_2)(CH_2)_m$—X, wherein m is 0, 1, 2, 3 or 4, such that when m is 1, 2, 3 or 4, X is
(1)

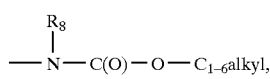

(2) —O—C(O)—$C_{1-6}$alkyl,
(3) —O—$R_8$, wherein $R_8$ and $R_{11}$ are defined immediately below,
(4)

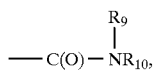

wherein $R_8$, $R_9$ and $R_{10}$, $R_{11}$ are each independently hydrogen, $C_{1-6}$alkyl, phenyl or benzyl, or wherein $R_9$ and $R_{10}$ are joined together with the nitrogen to which they are attached to form a saturated monocyclic ring of 5 to 7 atoms containing one or two heteroatoms selected from
(a) morpholinyl,
(b) thiomorpholinyl,
(c) piperadinyl,
(d) pyrrolidinyl,
said ring optionally substituted with $C_{1-3}$ alkyl, (5)

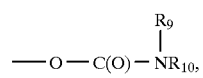

(6)

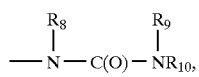

(7)

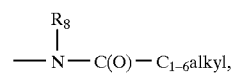

(8) —OH,
(9) $C_{1-3}$ alkykoxy-$C_{1-3}$ alkyloxy,
(10) —C(O)OH, —C(O)OR$_8$, or C(O)$C_{1-6}$ alkyl,
(11) —S—$C_{1-6}$alkyl,
(12) —S(O)—$C_{1-6}$alkyl, or
(13) —S(O)$_2$—$C_{1-6}$alkyl;

and when m is 0,

X is —C(O)OH or —C(O)N($R_{10}$)$R_9$—C(O)O$R_8$, C(O)$C_{1-6}$ alkyl;
(e) C(O)—Y, wherein Y is
(1) hydrogen,
(2) $C_{1-6}$alkyl,
(3)

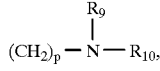

wherein p is 0, 1 or 2,
(4) pyridylmethyl,
(5) imidazolyl methyl,
(f) mono or disubstituted benzyl or mono substituted pyridylmethyl, wherein the substitutent is
(1) hydrogen,
(2) halo,
(3) $C_{1-6}$ alkyl, or
(4) $C_{1-6}$ alkylcarbonylamino;

$R_6$ is selected from hydrogen, $C_{1-4}$ alkyl, and $C_{1-3}$ alkoxy-$C_{1-3}$ alkyl.

6. A compound according to claim 1 wherein
R is $C_{1-6}$ alkyl;
$R^1$ is $C_{1-6}$ alkyl or $C_{1-6}$ alkoxy-$C_{1-6}$ alkyl;
M is
(1) $C_{1-6}$ alkyl,
(2) hydroxy $C_{1-6}$alkyl,
(3) halo $C_{1-6}$ alkyl,
(4) $C_{2-6}$ alkenyl, or
(5) $C_{1-6}$alkyloxy-$C_{1-6}$alkyl;

$R^2$ and $R^3$ are each independently
(1) hydrogen,
(2) $C_{1-6}$ alkyl,
(3) halo,
(4) carboxy,
(5) $C_{1-6}$ alkoxy,
(6) phenyl,
(7) $C_{1-6}$ alkylcarbonyl,
(8) di-($C_{1-6}$alkyl)amino, or $R^2$ and $R^3$ are joined together to form the group methylenedioxy or $R^2$ and $R^3$ together with the carbon atoms to which they are attached form a furan ring;

$R_7$ is
(a) hydrogen,
(b) halo,
(c) $C_{1-3}$alkyl,
(d) hydroxy, or
(e) $C_{1-3}$alkoxy; and n is 0;

$R_4$ is selected from
(a) hydrogen,
(b) $C_{1-6}$ alkyl,
(c) $C_{1-6}$ alkyloxy $C_{2-3}$ alkyl; or
(d) cyclopropyl, $R_5$ is selected from
(a) hydrogen,
(b) $C_{1-6}$ alkyl,
(c) $C_{1-6}$ alkyloxy $C_{2-3}$ alkyl,
(d)

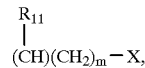
(CH)(CH$_2$)$_m$—X, wherein m is 0, 1, 2, 3 or 4, such that when m is 1, 2, 3 or 4, X is (1)

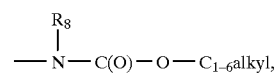
—N—C(O)—O—C$_{1-6}$alkyl, (2) —O—C(O)—C$_{1-6}$alkyl,
(3) —O—R$_8$, wherein R$_8$ and R$_{11}$ are defined immediately below, or O—R$_8$ and R$_{11}$ may be joined together to form a saturated ring of 5–7 atoms containing a single heteroatom which is oxygen, and the rest of the atoms are carbon,
(4)

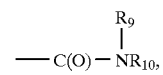
—C(O)—NR$_{10}$, wherein R$_8$, R$_9$ and R$_{10}$, R$_{11}$ are each independently hydrogen, C$_{1-6}$alkyl, phenyl or benzyl, or wherein R$_9$ and R$_{10}$ are joined together with the nitrogen to which they are attached to form a saturated monocyclic ring of 5 to 7 atoms containing one or two heteroatoms selected from
(a) morpholinyl,
(b) thiomorpholinyl,
(c) piperadinyl,
(d) pyrrolidinyl,
said ring optionallly substituted with C$_{1-3}$ aLkyl,
(5)

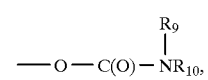
—O—C(O)—NR$_{10}$, (6)

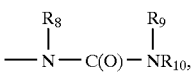
—N—C(O)—NR$_{10}$, (7)

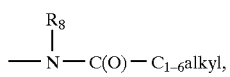
—N—C(O)—C$_{1-6}$alkyl, (8) —OH,
(9) C$_{1-3}$ alkoxy -C$_{1-3}$ alkoxy,
(10) —C(O)OH, —C(O) OR$_8$, or —C(O) C$_{1-6}$ alkyl,
(11) —S—C$_{1-6}$alkyl,
(12) —S(O)—C$_{1-6}$alkyl, or
(13) —S(O)$_2$—C$_{1-6}$alkyl;

and when m is 0,

X is —C(O)OH—C(O)OR$_8$, —C(O)—C$_{1-6}$ alkyl or

—C(O)NR$_9$
R$_{10}$;

(e) C(O)—Y, wherein Y is
(1) hydrogen,
(2) C$_{1-6}$alkyl,
(3)

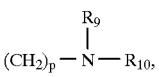
(CH$_2$)$_p$—N—R$_{10}$, wherein p is 0, 1 or 2,
(4) pyridylmethyl,
(5) imidazolyl methyl,
(f) mono or di substituted benzyl or mono substituted pyridylmethyl, wherein the substitutent is
(1) hydrogen,
(2) halo,
(3) C$_{1-6}$ alkyl, or
(4) C$_{1-6}$ alkylcarbonylamino;

$R_6$ is selected from hydrogen, C$_{1-4}$ alkyl, and C$_{1-3}$ alkoxy C$_{1-3}$alkyl; or wherein R$_4$ and R$_5$ are joined together to form a mono or di substituted ring of 5, 6, or 7 atoms selected from
(1) piperidinyl,
(2) piperazinyl,
(3) morpholinyl,
(4) thiomorpholinyl,
(5) pyrrolidinyl,
(6) pyrryl, and
(7) imidazolyl, wherein the substituents are each selected from the group consisting of hydrogen, hydroxy, hydroxymethyl, C$_{1-3}$ alkyl, C$_{1-3}$ alkyloxy, C$_{1-3}$ alkyloxymethyl, C$_{1-6}$ alkylcarbonyl;

R$_4$ and R$_6$ are joined together to form a monocyclic saturated ring of 5, 6, or 7 atoms including the atoms to which they are attached, said ring optionally having a second hetero atom selected from O or N or S.

7. A compound according to claim 4 wherein
R is methyl or ethyl;
R$_1$ is methyl or ethyl;

M is
(a) $C_{1-4}$ alkyl, or
(b) $C_{2-3}$ alkenyl;

$R^2$ is
(a) hydrogen,
(b) $C_{1-3}$ alkyl, or $C_{1-3}$ alkoxy, and $R^3$ is hydrogen, or $R^2$ and $R^3$ are joined together to form the group methylenedioxy or $R_2$ and $R_3$ together with the carbon atom to which they are attached form a furan ring;

$R_4$ is selected from
(a) hydrogen,
(b) $C_{1-3}$ alkyl, and
(c) $C_{1-3}$ alkoxy $C_{2-3}$ alkyl;

$R_5$ is selected from
(a) hydrogen,
(b) $C_{1-3}$ alkyl,
(c) $C_{1-3}$ alkyloxy $C_{2-3}$ alkyl,
(d) $CH_2$—$(CH_2)_m$—X, wherein m is 1;

X is
(1)

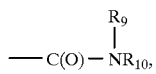
—C(O)—NR$_{10}$, wherein $R_8$, $R_9$ and $R_{10}$ are each independently hydrogen or C1–6alkyl, (2)

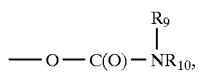
—O—C(O)—NR$_{10}$, (3)

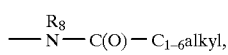
—N—C(O)—$C_{1-6}$alkyl, (4)

—N—C(O)N—R$_{10}$ (e) mono substituted benzyl or mono substituted pyridylmethyl, wherein the substitutent is
(1) hydrogen,
(2) halo,
(3) $C_{1-3}$ alkyl, or
(4) $C_{1-3}$ alkylcarbonylamino;

n is 0, $R_6$ is selected from hydrogen, methyl and methoxymethyl; or $R_4$ and $R_5$ or $R_9$ and $R_{10}$ are joined together with the nitrogen to which they are attached to form a mono or disubstituted ring selected from
(a) piperidinyl,
(b) pyrrolidinyl, and
(c) morpholinyl; or $R_4$ and $R_6$ are joined together to form a pyrrolidinyl ring; or $R_4$ and $R_8$ are joined together to form a piperazinyl ring.

8. A compound according to claim 5
wherein

R is $C_{1-3}$ alkyl;

$R_1$ is $C_{1-3}$ alkyl;

M is
(a) $C_{1-6}$ alkyl, or
(b) $C_{2-6}$ alkenyl;

$R^2$ is
(a) hydrogen
(b) $C_{1-6}$ alkyl, or $C_{1-6}$ alkoxy, and $R^3$ is hydrogen, or $R^2$ and $R^3$ are joined together to form the group methylenedioxy or $R^2$ and $R^3$ together with the carbon atoms to which they are attached form a furan ring;

$R_4$ is selected from
(a) hydrogen,
(b) $C_{1-3}$ alkyl, and
(c) $C_{1-3}$ alkoxy $C_{2-3}$ alkyl;

$R_5$ is selected from
(a) hydrogen,
(b) $C_{1-6}$ alkyl,
(c) $C_{1-6}$ alkyloxy $C_{2-3}$ alkyl,
(d) —$CH_2$—$(CH_2)_m$—X, wherein m is 0, 1 or 2, such that when m is 1 or 2, X is
(1) —O—C(O)—$C_{1-6}$alkyl,
(2) —O—$R_8$,
(3)

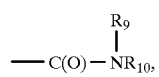
—C(O)—NR$_{10}$, wherein $R_8$, $R_9$ and $R_{10}$ are each independently hydrogen or $C_{1-6}$alkyl, (4)

—O—C(O)—NR$_{10}$, (5)

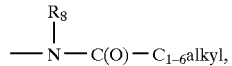
—N—C(O)—$C_{1-6}$alkyl, (6) —OH,
(7) —S—$C_{1-6}$alkyl,
(8) —S(O)—$C_{1-6}$alkyl, or
(9) —S(O)$_2$—$C_{1-6}$alkyl;
(10)

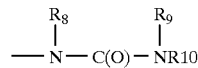
—N—C(O)—NR10 and when m is 0,

X is —C(O)OH or

(e) mono substituted benzyl or mono substituted pyridylmethyl, wherein the substitutent is
(1) hydrogen,
(2) halo,
(3) $C_{1-6}$ alkyl, or
(4) $C_{1-6}$ alkylcarbonylamino;

n is 0, and $R_6$ is selected from hydrogen, $C_{1-4}$ alkyl, and $C_{1-3}$ alkoxy $C_{1-3}$alkyl.

9. A compound according to claim 8 wherein

R is methyl or ethyl;

$R_1$ is methyl or ethyl;

M is
(a) $C_{1-4}$ alkyl, or
(b) $C_{2-3}$ alkenyl;

$R^2$ is
(a) hydrogen,
(b) $C_{1-3}$ alkyl, or $C_{1-3}$ alkoxy, and $R^3$ is hydrogen, or $R^2$ and $R^3$ are joined together to form the group methylenedioxy or $R_2$ and $R_3$ together with the carbon atom to which they are attached form a furan ring;

$R_4$ is selected from
(a) hydrogen,
(b) $C_{1-3}$ alkyl, and
(c) $C_{1-3}$ alkoxy $C_{2-3}$ alkyl;

$R_5$ is selected from
(a) hydrogen,
(b) $C_{1-3}$ alkyl,
(c) $C_{1-3}$ alkyloxy $C_{2-3}$ alkyl,
(d) CH2-(CH2)m-X, wherein m is 1;

X is
(1)

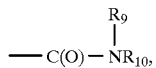

wherein $R_8$, $R_9$ and $R_{10}$ are each independently hydrogen or $C_{1-6}$alkyl, (2)

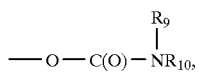

(3)

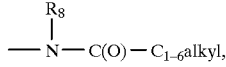

(4)

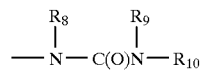

(e) mono or substituted benzyl or mono substituted pyridylmethyl, wherein the substitutent is
(1) hydrogen,
(2) halo,
(3) $C_{1-3}$ alkyl, or
(4) $C_{1-3}$ alkylcarbonylamino;

n is 0, $R_6$ is selected from hydrogen, methyl or methoxymethyl.

10. A compound according to claim 2 wherein

R is $C_{1-3}$ alkyl;

$R_1$ is $C_{1-3}$ alkyl;

M is
(a) $C_{1-6}$ alkyl, or
(b) $C_{2-6}$ alkenyl;

$R^2$ is
(a) hydrogen
(b) $C_{1-6}$ alkyl, or $C_{1-6}$ alkoxy, and $R^3$ is hydrogen, or $R^2$ and $R^3$ are joined together to form the group methylenedioxy or $R^2$ and $R^3$ together with the carbon atoms to which they are attached form a furan ring;

$R_4$ is selected from
(a) hydrogen,
(b) $C_{1-3}$ alkyl, and
(c) $C_{1-3}$ alkoxy $C_{2-3}$ alkyl;

$R_5$ is selected from
(a) hydrogen,
(b) $C_{1-6}$ alkyl,
(c) $C_{1-6}$ alkyloxy $C_{2-3}$ alkyl,
(d) —CH$_2$—(CH$_2$)$_m$—X, wherein m is 0, 1 or 2, such that when m is 1 or 2, X is
(1) —O—C(O)—$C_{1-6}$alkyl,
(2) —O—$R_8$,
(3)

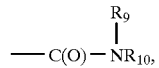

wherein $R_8$, $R_9$ and $R_{10}$ are each independently hydrogen or $C_{1-6}$alkyl, (4)

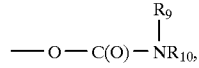

(5)

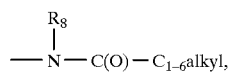

(6) —$C_{1-3}$ alkyloxyethyl,
(7) —S—$C_{1-6}$alkyl,
(8) —S(O)—$C_{1-6}$alkyl, or (9) —S(O)$_2$—C$_{1-6}$alkyl;
(10)

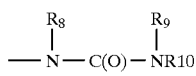

and when m is 0,

X is —C(O)OH or

(e) mono substituted benzyl or mono substituted pyridylmethyl, wherein the substituent is
 (1) hydrogen,
 (2) halo,
 (3) C$_{1-6}$ alkyl, or
 (4) C$_{1-6}$ alkylcarbonylamino;

n is 0, and

R$_4$ and R$_5$ or R$_9$ and R$_{10}$ are joined together with the nitrogen to which they are attached to form a mono or di substituted ring selected from
 (a) piperidinyl,
 (b) pyrrolidinyl, and
 (c) morpholinyl.

11. A compound according to claim 10 wherein

R is methyl or ethyl;

R$_1$ is methyl or ethyl;

M is
 (a) C$_{1-4}$ alkyl, or
 (b) C$_{2-3}$ alkenyl;

R$^2$ is
 (a) hydrogen,
 (b) C$_{1-3}$ alkyl, or C$_{1-3}$ alkoxy, and

R$^3$ is hydrogen, or

R$^2$ and R$^3$ are joined together to form the group methylenedioxy or R$_2$ and R$_3$ together with the carbon atom to which they are attached form a furan ring;

R$_4$ is selected from
 (a) hydrogen,
 (b) C$_{1-3}$ alkyl, and
 (c) C$_{1-3}$ alkoxy C$_{2-3}$ alkyl;

R$_5$ is selected from
 (a) hydrogen,
 (b) C$_{1-3}$ alkyl,
 (c) C$_{1-3}$ alkyloxy C$_{2-3}$ alkyl,
 (d) CH$_2$—(CH$_2$)$_m$—X, wherein m is 1;

X is
 (1)

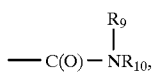

wherein R$_8$, R$_9$ and R$_{10}$ are each independently hydrogen or C$_{1-6}$alkyl, (2)

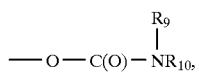

(3)

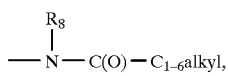

(4)

(e) mono substituted benzyl or mono substituted pyridylmethyl, wherein the substitutent is
 (1) hydrogen,
 (2) halo,
 (3) C$_{1-3}$ alkyl, or
 (4) C$_{1-3}$ alkylcarbonylamino;

n is 0,

R$_6$ is selected from hydrogen, methyl and methoxymethyl; or R$_4$ and R$_5$ or R$_9$ and R$_{10}$ are joined together with the nitrogen to which they are attached to form a mono or di substituted ring selected from
 (a) piperidinyl,
 (b) pyrrolidinyl, and
 (c) morpholinyl.

12. A compound according to claim 6 wherein

R is C$_{1-3}$ alkyl;

R$_1$ is C$_{1-3}$ alkyl;

M is
 (a) C$_{1-6}$ alkyl, or
 (b) C$_{2-6}$ alkenyl;

R$^2$ is
 (a) hydrogen
 (b) C$_{1-6}$ alkyl, or C$_{1-6}$ alkoxy, and R$^3$ is hydrogen, or R$^2$ and R$^3$ are joined together to form the group methylenedioxy or R$^2$ and R$^3$ together with the carbon atoms to which they are attached form a furan ring;

R$_4$ is selected from
 (a) hydrogen,
 (b) C$_{1-3}$ alkyl, and
 (c) C$_{1-3}$ alkoxy C$_{2-3}$ alkyl;

R$_5$ is selected from
 (a) hydrogen,
 (b) C$_{1-6}$ alkyl,
 (c) C$_{1-6}$ alkyloxy C$_{2-3}$ alkyl,
 (d) CH$_2$—(CH$_2$)$_m$—X, wherein m is 1, 2, such that when m is 1 or 2, X is
 (1) —O—C(O)—C$_{1-6}$alkyl,
 (2) —O—R$_8$, (3)

$$-C(O)-NR_{10},\ \overset{R_9}{|}$$

wherein $R_8$, $R_9$ and $R_{10}$ are each independently hydrogen or $C_{1-6}$alkyl, (4)

$$-O-C(O)-NR_{10},\ \overset{R_9}{|}$$

(5)

$$-\overset{R_8}{\underset{|}{N}}-C(O)-C_{1-6}\text{alkyl},$$

(6) —OH,
(7) —S—$C_{1-6}$alkyl,
(8) —S(O)—$C_{1-6}$alkyl, or
(9) —S(O)$_2$—$C_{1-6}$alkyl, (1)

$$-\overset{R_8}{\underset{|}{N}}-C(O)N\overset{R_9}{\underset{|}{R_{10}}}$$

and when m is 0,
X is —C(O)OH or $$-C(O)N\overset{R_9}{\underset{|}{R_{10}}};$$

(e) mono substituted benzyl or mono substituted pyridylmethyl, wherein the substitutent is
(1) hydrogen,
(2) halo,
(3) $C_{1-6}$ alkyl, or
(4) $C_{1-6}$ alkylcarbonylamino;

n is 0, $R_6$ is selected from hydrogen, $C_{1-4}$ alkyl, and $C_{1-3}$ alkoxy $C_{1-3}$alkyl; or $R_4$ and $R_6$ are joined together to form a saturated monocyclic ring of 5 to 6 atoms including the atoms to which they are attached, said ring optionally having a second hetero atom selected from O or N.

13. A compound according to claim 12 wherein

R is methyl or ethyl;
$R_1$ is methyl or ethyl;
M is
(a) $C_{1-4}$ alkyl, or
(b) $C_{2-3}$ alkenyl;
$R^2$ is
(a) hydrogen,
(b) $C_{1-3}$ alkyl, or $C_{1-3}$ alkoxy, and
$R^3$ is hydrogen, or
$R^2$ and $R^3$ are joined together to form the group methylenedioxy or $R_2$ and $R_3$ together with the carbon atom to which they are attached form a furan ring;
$R_4$ is selected from
(a) hydrogen,
(b) $C_{1-3}$ alkyl, and
(c) $C_{1-3}$ alkoxy $C_{2-3}$ alkyl;
$R_5$ is selected from
(a) hydrogen,
(b) $C_{1-3}$ alkyl,
(c) $C_{1-3}$ alkyloxy $C_{2-3}$ alkyl,
(d) CH$_2$—(CH$_2$)$_m$—X, wherein m is 1;
X is
(1)

$$-C(O)-NR_{10},\ \overset{R_9}{|}$$

wherein $R_8$, $R_9$ and $R_{10}$ are each independently hydrogen or $C_{1-6}$alkyl, (2)

$$-O-C(O)-NR_{10},\ \overset{R_9}{|}$$

(3)

$$-\overset{R_8}{\underset{|}{N}}-C(O)-C_{1-6}\text{alkyl},$$

(4)

$$-\overset{R_8}{\underset{|}{N}}-C(O)\overset{R_9}{\underset{|}{N}}-R10$$

(e) mono substituted benzyl or mono substituted pyridylmethyl, wherein the substitutent is
(1) hydrogen,
(2) halo,
(3) $C_{1-3}$ alkyl, or
(4) $C_{1-3}$ alkylcarbonylamino;

n is 0, $R_6$ is selected from hydrogen, methyl, and methoxymethyl; or $R_4$ and $R_6$ are joined together to form a saturated mono cyclic ring of 5 to 6 atoms including the atoms to which they are attached, said ring optionally having a second hetero atom selected from O or N.

14. A compound according to claim 1 of the following Formula:

or a pharmaceutically acceptable salt thereof wherein

| R4 | R5 | R6 |
|---|---|---|
| Me | Bn | H |
| —CH₂CH₂OCH₂CH₂— | | H |
| Me | Me | H |
| —CH₂CH₂N(i-Pr)CH₂CH₂— | | H |
| —CH₂CH₂N(Ac)CH₂CH₂— | | H |
| —CH₂CH₂N(Bz)CH₂CH₂— | | H |
| Me | CH₂CH₂CO₂H—TFA | H |
| Me | CH₂CH₂OH | H |
| —CH₂CHMeNCHMeCH₂— | | H |
| —CHMeCH₂CH₂CHMe- | | H |
| Me | CH₂CH₂NMe₂ | H |
| Me | CH₂CH₂N(Me)Bn | H |
| —CHCHNCH— | | H |
| Me | CH₂CH₂OCONMe₂ | H |
| Me | CH₂CH₂CONMe₂ | H |
| —CH₂CH₂N(CO₂Me)CH₂CH₂— | | H |
| Me | CH₂CH₂OMe | H |
| —CH₂CH₂N(CONMe₂)CH₂CH₂— | | H |
| Me | CH₂CH₂OCONHMe | H |
| —CHCHNCMe— | | H |
| —CH₂CH₂N(CONEt₂)CH₂CH₂— | | H |
| Me | CH₂CH₂N(Me)CONMe₂ | H |
| Me | i-Pr | H |
| i-Pr | CH₂CH₂OMe | H |
| Me | CH₂CH₂N(Me)Ac | H |
| Et | CH₂CH₂OMe | H |
| Me | CH₂CH₂N(Me)COOMe | H |
| —CHMeCH₂CH₂CH₂CHMe- | | H |
| Me | CH₂CH₂OEt | H |
| Me | CH₂CH₂OCOCMe₃ | H |
| Me | CH₂CH₂OCOCHMe₂ | H |
| Me | CH₂CH₂OPh | H |
| Me | CH₂CH₂OCONEt₂ | H |
| —CHCHNCEt— | | H |
| —CH₂CMeNCH₂CHMe— | | H |
| Me | CH₂CH₂OCONH(i-Pr) | H |
| Me | CH₂CH₂OCON(CH₂CH₂OCH₂CH₂) | H |
| Me | CH₂CH₂OCON(Me)n-Bu | H |
| Me | CH₂CON(n-Pr)₂ | H |
| Me | CH₂CH₂SEt | H |
| CH₂CH₂OMe | CH₂CH₂OMe | H |
| Me | CH₂CH(CH₂CH₂CH₂CH₂O) | H |
| Me | CH₂CH₂SMe | H |
| Et | CH₂CH₂NHAc | H |
| Me | CH₂CH(CH₂CH₂CH₂O) | H |
| Me | CH₂CH₂OCONMe₂ | Me |
| Et | CH₂CH₂OMe | Me |
| Me | CH₂CH₂OMe | Me |
| —CH₂CH₂SCH₂— | | H |
| —CH₂CH₂SCH₂CH₂— | | H |
| —CH₂CH₂CH₂CH(S—CH₂OH) | | H |
| —CH₂CH₂CH₂CH(S—CH₂OMe)— | | H |
| —CH₂CH₂CH(OH)CH₂— | | H |
| —CH₂CH₂CH(OH)CH₂CH₂— | | H |
| Me | Me CH₂OMe | H |
| Me | CH(Me)CH₂OMe | H |
| Et | CH₂CH₂OCONMe₂ | H |
| Me | CH₂CH₂SOEt | H |
| Me | CH₂CH₂SO₂Et | H |
| Me | CH₂CH₂CH₂OMe | H |
| Me | CH₂Ci₂CH₂OCONMe₂ | H |
| Me | CH₂CH₂OCH₂CH₂OMe | H |
| Et | CH₂CH₂OCH₂CH₂OMe | H |
| Et | CH(Me)CH₂OMe | H |
| —CH₂CH₂N(COCHMe₂)CH₂CH₂— | | H |
| Et | Et | CH₂OMe |
| n-Pr | n-Pr | CH₂OMe |
| —CH₂CH₂CH₂CH₂— | | CH₂OMe |
| Me | n-Pr | CH₂OMe |
| —CH₂CH₂OCH₂CH₂— | | Me |
| Me | CH₂CH₂OMe | Et |
| —CH₂CH₂CH(OMe)CH₂— | | H |
| —CH₂CH₂CH₂CH(S—CH₂OMe)— | | Me |
| Me | CH(Me)CH₂OMe | Me |
| Me | CH₂CH₂OCH₂CH₂OMe | Me |
| Me | Et | CH₂OMe |
| —CH₂CH₂CH(OMe)CH₂— | | Me |
| —CH₂CH₂CH₂CH(R—CH₂OH)— | | H |
| Et | CH₂CH₂SMe | H |
| CH₂CH₂OMe | —CH₂CH₂CH₂— | |
| Me | CH₂CH₂OMe | (S)-Me |
| Me | CH₂CH₂OMe | (R)-Me |
| H | Me | (R)-Me |
| H | Me | (S)-Me |
| Me | CH₂CH₂OH | Me |
| H | CH₂CH₂OMe | Me |
| H | CH₂CH₂OH | Me |
| Me | i-Pr | CH₂OMe |
| CH₂CH₂OEt | —CH₂CH₂CH₂— | |
| H | H | H |
| H | Me | H |
| H | Ac | H |
| H | CONH isoPr | H |
| H | CONHMe | H |
| H | CONPr | H |
| H | CONH Bn | H |
| H | COCH₂ NMe2 | H |
| H | COCH₂ CH₂ N Et₂ | H |
| H | COCH₂-3-pyridyl | H |
| H | COCH₂-4-pyridyl | H |
| H | COCH₂-4-imidazolyl | H |
| H | COCH₂ N(Me)Bn | H | wherein Bn is benzyl, Ac is acetyl, and TFA is trifluoroacetate.

15. A compound selected from the group consisting of:
(a) (4S)-3,3-Diethyl-1-[(R)-α-n-propyl-(4-methyl)benzylaminocarbonyl]-4-[(4-(2-(methoxy)eth-1-yl)methylaminomethyl)phenoxy]azetidin-2-one;
(b) (4S)-3,3-Diethyl-1-[(R)-α-n-propyl-(4-methyl)benzylaminocarbonyl]-4-[(4-(2-(ethoxy)eth-1-yl)methylaminomethyl)phenoxy]azetidin-2-one;
(c) 3,3-Diethyl-1-[(R)-α-(n-propyl)-4-(methyl)benzylaminocarbonyl]-4-(S)-[4-{1-(RS)-(N-(n-propyl)-N-(methyl)amino)-2-(methoxy)eth-1-yl}phenoxy]azetidin-2-one;
(d) 3,3-Diethyl-1-[(R)-α-(n-propyl)-4-(methyl)benzylaminocarbonyl]-4-(S)-[4-{1-(RS)-(N,N-dimethylamino)-2-(methoxy)eth-1-yl}phenoxy]azetidin-2-one;
(e) 3,3-Diethyl-1-[(R)-α-(n-propyl)-4-(methyl)benzylaminocarbonyl]-4-(S)-4-[4-{1-(RS)-(N,N-diethylamino)-2-(methoxy)eth-1-yl}phenoxy]azetidin-2-one;
(f) 3,3-Diethyl-1-[(R)-α-(n-propyl)-4-(methyl)benzylaminocarbonyl]-4-(S)-[4-{1-(RS)-(1-pyrrolidino)-2-(methoxy)eth-1-yl}phenoxy]azetidin-2-one;
(g) 3,3-Diethyl-1-[(R)-α-(n-propyl)-4-(methyl)benzylaminocarbonyl]-4-(S)-[4-{1-(RS)-(N-ethyl-N-(methyl)amino)-2-(methoxy)eth-1-yl}phenoxy]azetidin-2-one;
(h) 3,3-Diethyl-1-[(R)-α-(n-propyl)-(3,4-dioxomethylene)benzylaminocarbonyl]-4-(S)-[4-{1-(RS)-(N,N-dimethylamino)-2-(methoxy)eth-1-yl}phenoxy]azetidin-2-one;
(i) 3,3-Diethyl-1-[(R)-α-(n-propyl)-(3,4-dioxomethylene)benzylaminocarbonyl]-4-(S)-[4-{1-(RS)-(N-ethyl-N-(methyl)amino)-2-(methoxy)eth-1-yl}phenoxy]azetidin-2-one; and
(j) 3,3-Diethyl-1-[(R)-α-(n-propyl)-(3,4-dioxomethylene)benzylaminocarbonyl]-4-(S)-[4-{1-(RS)-(N-(n- propyl)-N-(methyl)amino)-2-(methoxy)eth-1-yl}phenoxy]azetidin-2-one.

16. A compound of the following Formula:

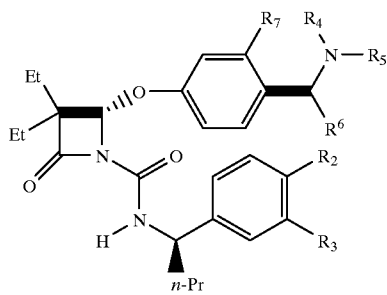

or a pharmaceutically acceptable salt thereof wherein

| R₂ | R₃ | R₄ | R₅ | R₆ | R₇ |
|---|---|---|---|---|---|
| OMe | H | Me | CH₂CH₂OMe | H | H |
| OEt | H | Me | CH₂CH₂OMe | H | H |
| OEt | H | Et | CH₂CH₂OMe | H | H |
| OMe | H | Et | CH₂CH₂OMe | H | H |
| Me | H | Et | CH₂CH₂OMe | H | Cl |
| Me | H | Me | CH(Me)CH₂OMe | H | OMe |
| —OCH₂C— | | Et | CH(Me)CH₂OMe | H | H |
| —OCH₂O— | | Et | CH₂CH₂OMe | H | H |
| Me | H | Et | CH₂CH₂CH₂CH₂OMe | H | OMe |
| Me | H | Et | CH(Me)CH₂OMe | H | OMe |
| Me | H | CH₂ | CH₂OMe CH₂CH₂OMe | H | Cl |
| Me | H | Me | CH₂CH₂OMe | H | Cl |
| Me | H | Me | CH(Me)CH₂OMe | H | Cl |
| Me | H | Me | CH₂CH₂OMe | H | 3,5-Me₂ |
| Me | H | Me | CH₂CH₂OMe | H | Me |
| Me | H | Et | CH₂CH₂OMe | H | Me |
| Me | H | Et | CH(Me)CH₂OMe | H | Me |
| —OCH₂O— | | O— | Et CH₂CH₂OGONMe₂ | H | H |
| —OCH₂O— | | Me | n-Pr   CH₂OMe | H | |
| —OCH₂O— | | Me | Et   CH₂OMe | H | |
| —OCHCH— | | Et | CH(Me)CH₂OMe | H | H |
| —OCHCH— | | Et | CH₂CH₂OMe | H | H |
| —OCH₂O— | | Et | CH₂CH₂OMe | H | H |
| —OCH₂O— | | Me | CH₂CH₂OMe | Me | H |
| —OCH₂O— | | Me | Me | CH₂OMe | H |
| —OCH₂O— | | H | cyclopropyl | H | H |
| —OCH₂O— | | —CH₂CH₂N(CONMe₂)CH₂CH₂— | | H | H |

17. A compound which is
(a) (4S)-3,3-Diethyl-1-[(R)-α-n-propyl-(4-methyl)-benzylamincarbonyl]-4-[((4-((4-dimethylaminocarbonyl)-piperazin-1-yl)methyl)phenoxy]azetidin-2-one;
(b) (4S)-3,3-Diethyl-1-[(R)-α-n-propyl-(3,4-methylenedioxy-benzylaminocarbonyl]-4-[(4-[((4-((4-dimethylaminocarbonyl)-piperazin-1-yl)methyl)phenoxy]-azetidin-2-one;
(c) (4S)-3,3-Diethyl-1-[(R)-α-n-propyl-(4-methyl)-benzyl-aminocarbonyl]-4-[(4-(2-methoxyethyl)ethylaminomethyl)phenoxy]azetidin-2-one;
(d) (4S)-3,3-Diethyl-4-{(S)-4-[1-((2-methoxyethyl)-methylamino)ethyl]phenoxy}-1-[(R)-α-n-propyl-(4-methyl)benzylaminocarbonyl]azetidin-2-one;
(e) (4S)-3,3-diethyl-4-{(R)-4-[1-((2-methoxyethyl)-methylamino)ethyl]phenoxy}-1-((R)-α-n-propyl-(4-methyl)benzylaninocarbonyl]azetidin-2-one;
(f) 3,3-Diethyl-1-[(R)-α-(n-propyl)-4-(methyl)-benzylamino-carbonyl]-4-[4-(1-(R,S)-((2-(dimethyl-aminocarbonyloxy)-ethyl)methylamino)ethyl)phenoxy]azetinin-2-one.

18. A pharmaceutical composition for the inhibition of human leukocyte elastase which comprises a nontoxic therapeutically effective amount of a compound of claim 1 and a pharmaceutically acceptable carrier.

19. A method of treatment for the inhibition of human leukocyte elastase which comprises the administration to a subject in need of such inhibition a nontoxic therapeutically effective amount of a compound of claim 1.

* * * * *